United States Patent
Gindy et al.

(10) Patent No.: US 11,406,706 B2
(45) Date of Patent: *Aug. 9, 2022

(54) LIPID NANOPARTICLE VACCINE ADJUVANTS AND ANTIGEN DELIVERY SYSTEMS

(71) Applicant: Merck Sharp & Dohme Corp., Rahway, NJ (US)

(72) Inventors: Marian Gindy, North Wales, PA (US); Danilo R. Casimiro, Harleysville, PA (US); Andrew Bett, Lansdale, PA (US); Jan H. Ter Meulen, Mercer Island, WA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/031,229

(22) Filed: Sep. 24, 2020

(65) Prior Publication Data

US 2021/0002813 A1    Jan. 7, 2021

Related U.S. Application Data

(63) Continuation of application No. 15/120,594, filed as application No. PCT/US2015/017007 on Feb. 23, 2015, now Pat. No. 9,869,054.

(60) Provisional application No. 61/944,336, filed on Feb. 25, 2014.

(51) Int. Cl.
| | |
|---|---|
| *A61K 39/39* | (2006.01) |
| *A61K 39/12* | (2006.01) |
| *D06F 81/00* | (2006.01) |
| *D06F 81/04* | (2006.01) |
| *D06F 81/08* | (2006.01) |
| *A61K 9/50* | (2006.01) |
| *A61K 31/451* | (2006.01) |
| *A61K 31/80* | (2006.01) |
| *A61K 39/29* | (2006.01) |
| *C12N 7/00* | (2006.01) |
| *A61K 39/00* | (2006.01) |
| *A61P 31/00* | (2006.01) |

(52) U.S. Cl.
CPC ............ *A61K 39/39* (2013.01); *A61K 9/5015* (2013.01); *A61K 9/5031* (2013.01); *A61K 31/451* (2013.01); *A61K 31/80* (2013.01); *A61K 39/12* (2013.01); *A61K 39/292* (2013.01); *C12N 7/00* (2013.01); *D06F 81/00* (2013.01); *D06F 81/04* (2013.01); *D06F 81/08* (2013.01); *A61K 2039/545* (2013.01); *A61K 2039/55505* (2013.01); *A61K 2039/55511* (2013.01); *A61K 2039/55555* (2013.01); *A61K 2039/55561* (2013.01); *A61K 2039/55572* (2013.01); *A61K 2039/55577* (2013.01); *A61P 31/00* (2018.01); *C12N 2730/10134* (2013.01); *C12N 2730/10171* (2013.01); *C12N 2770/24134* (2013.01); *C12N 2770/24171* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,208,036 A | 5/1993 | Eppstein et al. |
| 5,264,618 A | 11/1993 | Felgner et al. |
| 5,278,302 A | 1/1994 | Caruthers et al. |
| 5,279,833 A | 1/1994 | Rose |
| 5,283,185 A | 2/1994 | Epand et al. |
| 5,666,153 A | 9/1997 | Copeland |
| 5,885,613 A | 3/1999 | Holland et al. |
| 6,113,918 A | 9/2000 | Johnson et al. |
| 6,130,082 A | 10/2000 | Majarian et al. |
| 6,207,646 B1 | 3/2001 | Krieg et al. |
| 6,303,347 B1 | 10/2001 | Johnson et al. |
| 6,329,381 B1 | 12/2001 | Kurimoto et al. |
| 6,585,980 B1 | 7/2003 | Chan et al. |
| 6,696,076 B2 | 2/2004 | Tomai et al. |
| 6,764,840 B2 | 7/2004 | Johnson et al. |
| 6,890,557 B2 | 5/2005 | Huang et al. |
| 7,192,725 B2 | 3/2007 | Chan et al. |

(Continued)

FOREIGN PATENT DOCUMENTS

| | | |
|---|---|---|
| WO | 9526204 A1 | 10/1995 |
| WO | 9850399 A1 | 11/1998 |

(Continued)

OTHER PUBLICATIONS

U.S. Appl. No. 15/120,954, filed Aug. 23, 2016.

(Continued)

*Primary Examiner* — Robert A Wax
*Assistant Examiner* — Randeep Singh
(74) *Attorney, Agent, or Firm* — Nichole M. Valeyko; Alysia Finnegan

(57) ABSTRACT

The instant invention provides for novel lipid nanoparticle (LNP) formulations, containing cationic lipids, for use as vaccine adjuvants and/or as antigen delivery systems. It is an object of the instant invention to provide LNP formulations that demonstrate enhancements in humoral and/or cellular immunogenicity of vaccine antigens, particularly subunit vaccine antigens, when utilized alone or in combination with immunostimulatory agents (e.g. small molecule or oligonucleotide TLR agonists). The instant invention further identifies physical and chemical properties of the LNP formulations that can be manipulated to enhance antigen efficiency and adjuvant tolerability in vivo.

18 Claims, 16 Drawing Sheets

(56) References Cited

U.S. PATENT DOCUMENTS

| | | |
|---|---|---|
| 7,223,398 B1 | 5/2007 | Tuck et al. |
| 7,250,403 B2 | 7/2007 | Van Nest et al. |
| 7,566,703 B2 | 7/2009 | Krieg et al. |
| 7,691,405 B2 | 4/2010 | Chen et al. |
| 2003/0077829 A1 | 4/2003 | Maclachlan |
| 2005/0008689 A1 | 1/2005 | Semple et al. |
| 2006/0083780 A1 | 4/2006 | Heyes et al. |
| 2006/0240554 A1 | 10/2006 | Chen et al. |
| 2006/0241076 A1 | 10/2006 | Uhlmann et al. |
| 2008/0020058 A1 | 1/2008 | Chen et al. |
| 2008/0057080 A1 | 3/2008 | Luke et al. |
| 2008/0085870 A1 | 4/2008 | Hermanson et al. |
| 2009/0263407 A1 | 10/2009 | Dande et al. |
| 2009/0285881 A1 | 11/2009 | Dande et al. |
| 2010/0055168 A1 | 3/2010 | Dande et al. |
| 2010/0055169 A1 | 3/2010 | Dande et al. |
| 2010/0063135 A1 | 3/2010 | Dande et al. |
| 2010/0075995 A1 | 3/2010 | Biggadike et al. |
| 2010/0076055 A1 | 3/2010 | Dande et al. |
| 2010/0099738 A1 | 4/2010 | Hansen et al. |
| 2010/0104629 A1 | 4/2010 | Dande et al. |
| 2012/0264810 A1 | 10/2012 | Lin et al. |
| 2012/0276209 A1 | 11/2012 | Cullis et al. |
| 2013/0017239 A1 | 1/2013 | Petit et al. |
| 2013/0150433 A1 | 6/2013 | Bartz et al. |

FOREIGN PATENT DOCUMENTS

| | | |
|---|---|---|
| WO | 0000462 A1 | 6/2000 |
| WO | 0146127 A1 | 6/2001 |
| WO | 03043572 A2 | 5/2003 |
| WO | 03086280 A2 | 10/2003 |
| WO | 2004071459 A2 | 8/2004 |
| WO | 2005026372 A2 | 3/2005 |
| WO | 2005097993 A2 | 10/2005 |
| WO | 2005120152 A2 | 12/2005 |
| WO | 2006012425 A2 | 2/2006 |
| WO | 2006016997 A2 | 2/2006 |
| WO | 2007062107 A2 | 5/2007 |
| WO | 2008033432 A2 | 3/2008 |
| WO | 2009086558 A1 | 7/2009 |
| WO | 2009127060 A1 | 10/2009 |
| WO | 2009128950 A2 | 10/2009 |
| WO | 2009132131 A1 | 10/2009 |
| WO | 2009156405 A1 | 12/2009 |
| WO | 2010/021865 A1 | 2/2010 |
| WO | 2010018132 A1 | 2/2010 |
| WO | 2010042877 A1 | 4/2010 |
| WO | 2010048520 A1 | 4/2010 |
| WO | 2010054384 A1 | 5/2010 |
| WO | 2010054401 A1 | 5/2010 |
| WO | 2010054405 A1 | 5/2010 |
| WO | 2010054406 A1 | 5/2010 |
| WO | 2010105209 A1 | 9/2010 |
| WO | 2010144740 | 12/2010 |
| WO | 2011022460 A1 | 2/2011 |
| WO | 2011076807 A2 | 6/2011 |
| WO | 2012040184 A2 | 3/2012 |
| WO | 2013177419 A2 | 11/2013 |

OTHER PUBLICATIONS

Abrams, Mark T. et al., Evaluation of Efficacy, Biodistribution, and Inflammation for a Potent siRNA Nanoparticle: Effect of Dexamethasone Co-Treatment, Molecular Therapy, 2010, 171-180, 18(1).

Agrawal, S. et al., Synthetic agonists of Toll-like receptors 7, 8 and 9, Biochem. Soc. Trans., 2007, 1461-1467, 35 (Pt6).

Archer, Kristina et al., STING-Dependent Type I IFN Production Inhibits Cell-Mediated Immunity to Listeria monocytogenes, PLOS Pathogens, 2014, 1-14, 10(1).

Badiee, Ali et al., Coencapsulation of CpG Oligodeoxynucleotides with Recombinant Leishmania major Stress-Inducible Protein 1 in Liposome Enhances Immune Response and Protection against Leishmaniasis in Immunized BALB/c Mice, Clinical and Vaccine Immunology, 2008, 668-674, 15(4).

Becker, Pablo D. et al., The HIV-1 matrix protein p17 can be efficiently delivered by intranasal route in mice using the TLR 2/6 agonsti MALP-2 as mucosal adjuvant, Vaccine, 2006, 5269-5276, 24.

Bhardwaj, Nina et al., TLR Agonists: Are They Good Adjuvants?, Cancer J., 2010, 382-391, 16(4).

Chikh, Ghania et al., Synthetic methylated CpG ODNs are potent in vivo adjuvants when delivered in liposomal nanoparticules, International Immunology, 2009, 757-767, 21(7).

Chu, Rose S. et al., CpG Oligodeoxynucleotides Act as Adjuvants that Switch on T Helper 1 (Th1) Immunity, J. Exp. Med., 1997, 1623-1631, 186(10).

Corrales, Leticia et al., Extremely potent immunotherapeutic activity of a STING agonist in the 816 melanoma model in vivo, Journal for ImmunoTherapy of Cancer, 2013, 1, 1.

Davis, Heather L. et al., CpG DNA Is a Potent Enhancer of Specific Immunity in Mice Immunized with Recombinant Hepatitis B Surface Antigen, J. Immunol., 1998, 870-876, 160.

Emerich, Dwaine F. et al., Biocompatibility of Poly (DL-Lactide-co-glycolide) Microspheres Implanted Into the Brain, Cell Transplantation, 1999, 47-58, 8.

Fisette, Philip L. et al., The Lip Lipoprotein from Neisseria gonorrhoeae Stimulates Cytokine Release and NF-KB Activation in Epithelial Cells in a Toll-like Receptor 2-dependent Manner, The Journal of Biological Chemistry, 2003, 46252-46260, 278(47).

Geall, Andrew J. et al., Nonviral delivery of self-amplifying RNA vaccines, Proceedings national Academy of Sciences, 2012, 14604-14609, 109:36.

Goldinger, Simone et al., Nano-particle vaccinatino combined with TLR-7 and -9 ligands triggers memory and effector CD8+ T-cell responses in melanoma patients, Eur J. Immunol., 2012, 3049-3061, 42.

Gray, Peter M. et al., Evidence for cyclic diguanylate as a vaccine adjuvant with novel immunostimulatory activities, Cellular Immunology, 2012, 113-119, 278.

Gursel, Ihsan et al., Sterically Stabilized Cationic Liposomes Improve the Uptake and Immunostimulatory Activity of CpG Oligonucleotides, J. Immunol., 2001, 3324-3328, 167.

Heil,, Species-Specific Recognition of Single-Stranded RNA via Toll-like Receptor 7 and 8, Science, 2004, 1526-1529, 303(5663).

Krieg, Arthur M. et al., CpG motifs in bacterial DNA trigger direct B-cell activation, Nature, 1995, 546-549, 374.

Lahiri, Amit et al., Engagement of TLR signaling as adjuvant: Towards smarter vaccine and beyond, Vaccine, 2008, 677-6783, 26.

Lambert, Stacie L. et al., Molecular and Cellular Response Profiles Induced by the TLR4 Agonist-Based Adjuvant Glycopyranosyl Lipid A, PLOS One, 2012, 1-11, 7(12).

Li, Wai Ming et al., Enhanced immune response to T-independent antigen by using CpG oligodeoxynucleotides encapsulated in liposomes, Vaccine, 2002, 148-157, 20.

Li, Xiao-Dong et al., Pivotal roles of cGAS-cGAMP Signaling in Antivirus Defense and Immune Adjuvant Effects, Science, 2013, 1390-1394, 341.

Lipford, Grayson B. et al., Bacterial DNA as immune cell activator, Trands in Microbiology, 1998, 496-500, 6(12).

Lipford, Grayson B. et al., CpG-containing synthetic oligonucleotides promote B and cytotoxic T cell responses to protein antigen: a new class of vaccine adjuvants, Eur. J. Immunol., 1997, 2340-2344, 27.

Makowska, Zuzanna et al., Sequential induction of type I and II interferons mediates a long-lasting gene induction in the liver in response to a novel toll-like receptor 9 agonist, Journal of Hepatology, 2013, 743-749, 58.

Martins, Susana et al., Lipid-based colloidal carriers for peptide and protein delivery—lipsomoes versus lipid nanoparticles, International Journal of Nanomedicine, 2007, 595-607, 2:4.

Muller, RH, Solid lipid nanoparticles (SLN) for controlled drug delivery—a review of the state of the art, European Journal of Pharmaceutics and Biopharmaceutics, 2000, 161-177, vol. 50.

(56) References Cited

OTHER PUBLICATIONS

Puri, Anu et al., Lipid-Based Nanoparticles as Pharmaceutical Drug Carriers: From Concepts to Clinic, Critical Reviews TM in Therapeutic Drug Carrier Systems, 2009, 523-580, 26(6).

Roman, Mark et al., Immunostimulatory DNA sequences function as T helper-1-promoting adjuvants, Nature Medicine, 1997, 849, 3(8).

Rose, William A. et al., FSL-1, a bacterial-derived toll-like receptor 2/6 agonst, enhances resistance to experimental HSV-2 infection, Virology Journal, 2009, 1-11, 6(195).

Semple, Sean C. et al., Rational design of cationic lipids for siRNA delivery, Nature Biotechnology, 2010, 172-178, 28(2).

Thoryk, Elizabeth et al., Co-Administration of Lipid Nanoparticles and Sub-Unit Vaccine Antigens is Required for increase in Antigen-Specific Immune Responses in Mice, Vaccine, 2016, 47, 4(4).

Wilson, Kaley D. et al., The combination of stabilized plasmid lipid particles and lipid nanoparticle encapsulated CpG contianing oligodeoxynucleotides as a systemic genetic vaccine, The Journal of Gene Medicine, 2009, 14-25, 11.

Zeng, Weiguang et al., Structural requirement for the agonist activity of the TLR2 ligand Pam2Cys, Amino Acids, 2010, 471-480, 39.

LIPID NANOPARTICLE VACCINE ADJUVANTS AND ANTIGEN DELIVERY SYSTEMS

CROSS-REFERENCE TO RELATED APPLICATIONS

This application is a continuation of application Ser. No. 15/120,954, filed Aug. 23, 2016, co-pending herewith, which is a U.S. National Phase application under 35 U.S.C. § 371 of PCT Application PCT/US2015/017007 filed Feb. 23, 2015, which claims priority from and the benefit of US Provisional Application No. U.S. Ser. No. 61/944,336 filed Feb. 25, 2014 and is hereby incorporated by reference in its entirety.

FIELD OF THE INVENTION

The present invention relates to immunological compositions comprising one or more antigens and lipid nanoparticles. The lipid nanoparticles are composed of a combination of cationic lipids with other lipid components such as PEG-lipids and optionally non-cationic lipids. The lipid nanoparticles can be used as vaccine adjuvants and antigen delivery systems. The lipid nanoparticles can also be used in combination with immunostimulatory compounds.

BACKGROUND OF THE INVENTION

Vaccine antigens, especially purified or recombinant subunit vaccines, are often poorly immunogenic and require the use of adjuvants to help stimulate protective immunity. Despite the success of currently approved adjuvants, there remains a need for improved adjuvants and delivery systems that enhance protective antibody responses, especially in populations that respond poorly to current vaccines.

Lipid nanoparticles (LNPs) constitute an alternative to other particulate systems, such as emulsions, liposomes, micelles, microparticles and/or polymeric nanoparticles, for the delivery of active ingredients, such as oligonucleotides and small molecule pharmaceuticals. LNPs and their use for the delivery of oligonucleotides have been previously disclosed. See U.S. Pat. No. 7,691,405, U.S. Patent Application Publication Nos: US 2006/0083780, US 2006/0240554, US 2008/0020058, US 2009/0263407 and US 2009/0285881; and International Patent Application Publication Nos.: WO 2009/086558, WO2009/127060, WO2009/132131, WO2010/042877, WO2010/054384, WO2010/054401, WO2010/054405 and WO2010/054406. See also Semple et al., 2010, *Nat. Biotechnol.* 28:172-176. Lipid-based nanoparticles as pharmaceutical drug carriers have also been disclosed. See Puri et al., 2009, *Crit. Rev. Ther. Drug Carrier Syst.* 26:523-580.

Other cationic lipids are disclosed in U.S. Patent Application Publication Nos. US 2009/0263407, US 2009/0285881, US 2010/0055168, US 2010/0055169, US 2010/0063135, US 2010/0076055, US 2010/0099738 and US 2010/0104629.

Other formulations for delivery of active agents having charged lipids are described in U.S. Pat. No. 6,890,557.

Lipid nanoparticle capsules are described in U.S. Patent Application Publication No. 2013/0017239.

SUMMARY OF THE INVENTION

The present invention is directed to a composition comprising: a) a lipid nanoparticle (LNP) comprising one or more cationic lipids and a poly(ethyleneglycol)-lipid (PEG-lipid); and b) one or more antigens. Such compositions can be used as vaccine adjuvants and/or vaccine antigen delivery agents, including for subunit vaccines.

In one embodiment, the cationic lipid is an ionizable cationic lipid, which may be selected from DLinDMA; DlinKC2DMA; DLin-MC3-DMA; CLinDMA; S-Octyl CLinDMA; (2S)-1-{7-[(3β)-cholest-5-en-3-yloxy]heptyloxy}-3-[(4Z)-dec-4-en-1-yloxy]-N,N-dimethylpropan-2-amine; (2R)-1-{4-[(3β)-cholest-5-en-3-yloxy]butoxy}-3-[(4Z)-dec-4-en-1-yloxy]-N,N-dimethylpropan-2-amine; 1-[(2R)-1-{4-[(3β)-cholest-5-en-3-yloxy]butoxy}-3-(octyloxy)propan-2-yl]guanidine; 1-[(2R)-1-{7-[(3β)-cholest-5-en-3-yloxy]heptyloxy}-N,N-dimethyl-3-[(9Z, 12Z)-octadeca-9,12-dien-1-yloxy]propan-2-amine; 1-[(2R)-1-{4-[(3β)-cholest-5-en-3-yloxy]butoxy}-N,N-dimethyl-3-[(9Z, 12Z)-octadeca-9,12-dien-1-yloxy]propan-2-amine; (2S)-1-({6-[(3β))-cholest-5-en-3-yloxy]hexyl}oxy)-N,N-dimethyl-3-[(9Z)-octadec-9-en-1-yloxy]propan-2-amine; (3β)-3-[6-{[(2S)-3-[(9Z)-octadec-9-en-1-yloxy]-2-(pyrrolidin-1-yl)propyl]oxy}hexyl)oxy] cholest-5-ene; (2R)-1-{4-[(3β)-cholest-5-en-3-yloxy]butoxy}-3-(octyloxy)propan-2-amine; (2R)-1-({8-[(3β)-cholest-5-en-3-yloxy]octyl}oxy)-N,N-dimethyl-3-(pentyloxy)propan-2-amine; (2R)-1-({8-[(3β)-cholest-5-en-3-yloxy]octyl}oxy)-3-(heptyloxy)-N,N-dimethylpropan-2-amine; (2R)-1-({8-[(3β)-cholest-5-en-3-yloxy]octyl}oxy)-N,N-dimethyl-3-[(2Z)-pent-2-en-1-yloxy]propan-2-amine; (2S)-1-butoxy-3-({8-[(3β)-cholest-5-en-3-yloxy]octyl}oxy)-N,N-dimethylpropan-2-amine; (2S-1-({8-[(3β)-cholest-5-en-3-yloxy]octyl}oxy)-3-[2,2,3,3,4,4,5,5,6,6,7,7,8,8,9,9-hexadecafluorononyl)oxy]-N,N-dimethylpropan-2-amine; 2-amino-2-{[(9Z,12Z)-octadeca-9,12-dien-1-yloxy]methyl}propane-1,3-diol; 2-amino-3-({9-[(3β,8ξ,9ξ,14ξ,17ξ,20ξ)-cholest-5-en-3-yloxy]nonyl}oxy)-2-{[(9Z,12Z)-octadeca-9,12-dien-1-yloxy]methyl}propan-1-ol; 2-amino-3-({6-[(3β,8ξ,9ξ,14ξ,17ξ,20ξ)-cholest-5-en-3-yloxy]hexyl}oxy)-2-{[(9Z)-octadec-9-en-1-yloxy]methyl}propan-1-ol; (20Z,23Z)-N,N-dimethylnonacosa-20,23-dien-10-amine; (17Z,20Z)-N,N-dimethylhexacosa-17,20-dien-9-amine; (16Z,19Z)-N,N-dimethylpentacosa-16,19-dien-8-amine; (13Z,16Z)-N,N-dimethyldocosa-13,16-dien-5-amine; (12Z,15Z)-N,N-dimethylhenicosa-12,15-dien-4-amine; (14Z,17Z)-N,N-dimethyltricosa-14,17-dien-6-amine; (15Z,18Z)-N,N-dimethyltetracosa-15,18-dien-7-amine; (18Z,21Z)-N,N-dimethylheptacosa-18,21-dien-10-amine; (15Z,18Z)-N,N-dimethyltetracosa-15,18-dien-5-amine; (14Z,17Z)-N,N-dimethyltricosa-14,17-dien-4-amine; (19Z,22Z)-N,N-dimethyloctacosa-19,22-dien-9-amine; (18Z,21Z)-N,N-dimethylheptacosa-18,21-dien-8-amine; (17Z,20Z)-N,N-dimethylhexacosa-17,20-dien-7-amine; (16Z,19Z)-N,N-dimethylpentacosa-16,19-dien-6-amine; (22Z,25Z)-N,N-dimethylhentriaconta-22,25-dien-10-amine; (21Z,24Z)-N,N-dimethyltriaconta-21,24-dien-9-amine; (18Z)-N,N-dimethylheptacos-18-en-10-amine; (17Z)-N,N-dimethylhexacos-17-en-9-amine; (19Z,22Z)-N,N-dimethyloctacosa-19,22-dien-7-amine; N,N-dimethylheptacosan-10-amine; (20Z,23Z)-N-ethyl-N-methylnonacosa-20,23-dien-10-amine; 1-[(11Z,14Z)-1-nonylicosa-11,14-dien-1-yl]pyrrolidine; (20Z)-N,N-dimethylheptacos-20-en-10-amine; (15Z)-N,N-dimethylheptacos-15-en-10-amine; (14Z)-N,N-dimethylnonacos-14-en-10-amine; (17Z)-N,N-dimethylnonacos-17-en-10-amine; (24Z)-N,N-dimethyltritriacont-24-en-10-amine; (20Z)-N,N-dimethylnonacos-20-en-10-amine; (22Z)-N,N-dimethylhentriacont-22-en-10-amine; (16Z)-N,N-dimethylpentacos-16-en-8-amine; (12Z,15Z)-N,N-dimethyl-2-nonylhenicosa-12,15-dien-1-amine; (13Z,16Z)-N,N-dimethyl-3-nonyldocosa-13, 16-dien-1-amine; N,N-dimethyl-1-[(1S,2R)-2-octylcyclopropyl]heptadecan-8-amine; 1-[(1S,2R)-2-hexylcyclopropyl]-N,N-dimethylnonadecan-10-amine; N,N-dimethyl-1-[(1S,2R)-2-octylcyclopropyl]nonadecan-10-amine; N,N-dimethyl-21-[(1S,2R)-2-octylcyclopropyl]henicosan-10-amine; N,N-dimethyl-1-[(1S,2S)-2-{[(1R,2R)-2-pentylcyclopropyl]methyl}cyclopropyl]nonadecan-10-amine; N,N-dimethyl-1-[(1S,2R)-2-octylcyclopropyl]hexadecan-8-amine; N,N-dimethyl-1-[(1R,2S)-2-undecylcyclopropyl]tetradecan-5-amine; N,N-dimethyl-3-{7-[(1S,2R)-2-octylcyclopropyl]heptyl}dodecan-1-amine; 1-[(1R,2S)-2-heptylcyclopropyl]-N,N-dimethyloctadecan-9-amine; 1-[(1S,2R)-2-decylcyclopropyl]-N,N-dimethylpentadecan-6-amine; N,N-dimethyl-1-[(1S,2R)-2-octylcyclopropyl]pentadecan-8-amine; and (11E,20Z,23Z)-N,N-dimethylnonacosa-11,20,23-trien-10-amine; or any pharmaceutically acceptable salt thereof, or a stereoisomer of any of the recited compounds or salts, or any combination thereof. In one aspect of this embodiment, the ionizable cationic lipid is selected from (2S)-1-({6-[(3β))-cholest-5-en-3-yloxy]hexyl}oxy)-N,N-dimethyl-3-[(9Z)-octadec-9-en-1-yloxy]propan-2-amine; (13Z,16Z)-N,N-dimethyl-3-nonyldocosa-13,16-dien-1-amine; and N,N-dimethyl-1-[(1S,2R)-2-octylcyclopropyl]heptadecan-8-amine; or a pharmaceutically acceptable salt thereof, or a stereoisomer of any of the foregoing, or any combination of the foregoing.

In certain embodiments, the LNP comprises 80-99.9 mole % ionizable cationic lipid and 0.1-20 mole % PEG-lipid. In certain embodiments of the invention, the LNP further comprises one or more non-cationic lipids which can be selected from a phospholipid, a phospholipid derivative, a fatty acid, a sterol, or a combination thereof. The sterol may be cholesterol, stigmasterol or stigmastanol. Natural phospholipids include phosphatidylcholine (PC), phosphatidylethanolamine (PE), and phosphatidylglycerol (PG), phosphatidylserine (PS), phosphatidylinositol (PI), Phosphatidic acid (phosphatidate) (PA), dipalmitoylphosphatidylcholine, monoacyl-phosphatidylcholine (lyso PC), 1-palmitoyl-2-oleoyl-sn-glycero-3-phosphocholine (POPC), N-Acyl-PE, phosphoinositides, and phosphosphingolipids. Phospholipid derivatives include phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), phosphatidylserine (DOPS). Fatty acids include C14:0, palmitic acid (C16:0), stearic acid (C18:0), oleic acid (C18:1), linoleic acid (C18:2), linolenic acid (C18:3), and arachidonic acid (C20:4), C20:0, C22:0 and lethicin. In certain embodiments of the invention, the phospholipid may be phosphatidylserine, 1,2-Distearoyl-sn-glycero-3-phosphocholine (DSPC), 1,2-dipalmitoleoyl-sn-glycero-3-phosphocholine, 1,2-dimyristoyl-sn-glycero-3-phosphocholine (DMPC), dilauroylphosphatidylcholine (DLPC), 1,2-dieicosenoyl-sn-glycero-3-phosphocholine, or 1,2-dioleoyl-sn-glycero-3-phosphocholine (DOPC).

In certain embodiments of the invention, the PEG-lipid is 1,2-Dimyristoyl-sn-glycerol methoxypolyethylene glycol (PEG-DMG), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In certain aspects of this embodiment, the PEG-lipid comprises a polyethylene glycol having an average molecular weight ranging from about 500 daltons to about 10,000 daltons.

In one embodiment of the invention, the LNP comprises 20-99.8 mole % ionizable cationic lipid, 0.1-65 mole % non-cationic lipids, and 0.1-20 mole % PEG-lipid. In one aspect of this embodiment, the non-cationic lipids comprise a mixture of cholesterol and DSPC.

In certain embodiments of the invention, the immunological composition further comprises one or more agonists selected from Toll-like receptors (TLR) agonists and Stimulator of Interferon Genes (STING) agonists. In certain aspects of this embodiment, the LNP comprises 20-99.7 mole % ionizable cationic lipid, 0.1-60.0 mole % non-cationic lipid, 0.1-15 mole % PEG-lipid, and 0.1-50 mole % agonists. The non-cationic lipids may comprise a mixture of cholesterol and DSPC. In one aspect of this embodiment, the agonist is a TLR agonist selected from synthetic immunostimulatory oligonucleotides (IMGs), or synthetic oligodeoxynucleotides (ODNs) containing CpG sequences. In another aspect of this embodiment, the agonist is a TLR agonist selected from Complete Freund's Adjuvant (CFA), monophosphoryl lipid A (MPL A), Glucopyranosyl Lipid Adjuvant (GLA), macrophage-activated lipopeptide-2 (MALP-2), Pam2Cys, Fibroblast Stimulating Lipopeptide-1 (FSL-1), PolyI:C, poly A:U, alkyl Glucosaminide phosphate (AGP), and imidazoquinolines. In one aspect of this embodiment, the agonist is a STING agonist selected from 3'3'-cGAMP, 2'3'-cGAMP, 2'2'-cGAMP, c-di-AMP, c-di-GMP, c-di-IMP, c-di-UMP, DMXAA or acylated conjugates or prodrugs thereof. The agonist may be physically encapsulated in the LNP before or after LNP preparation. The agonist may be adsorbed, covalently coupled, ionically-interacted or formulated onto the surface of the LNP.

In certain embodiments of the invention, the lipid nanoparticle comprises 34-59 mole % ionizable cationic lipid selected from the group consisting of (2S)-1-({6-[(3β))-cholest-5-en-3-yloxy]hexyl}oxy)-N,N-dimethyl-3-[(9Z)-octadec-9-en-1-yloxy]propan-2-amine; (13Z,16Z)-N,N-dimethyl-3-nonyldocosa-13,16-dien-1-amine; and N,N-dimethyl-1-[(1S,2R)-2-octylcyclopropyl]heptadecan-8-amine, 30-48 mole % cholesterol, 10-24% DSPC and 1-2 mole % PEG-DMG.

In certain embodiments of the invention, the lipid nanoparticle further comprises an immunostimulatory agent selected from saponin, squalene, aluminum phosphate and aluminum hydroxide.

In certain embodiments of the invention, at least one of the one or more antigens can be selected from antigens from RSV, Chlamydia, Dengue, CMV, Ebola, Varicella, Herpes viruses, HIV, or Influenza. In certain aspects of these embodiments, the antigens are subunit antigens. The one or more antigens may be physically encapsulated in the LNP before or after LNP preparation. The one or more antigens may be adsorbed, covalently coupled, ionically-interacted, or formulated onto surfaces of the LNP adjuvant.

The immunological compositions of the invention can be in the form of an aerosol, dispersion, solution, or suspension. The immunological compositions can be formulated for intramuscular, oral, sublingual, buccal, parenteral, nasal, subcutaneous, intradermal, or topical administration.

The present invention is also directed to methods of immunizing a subject or treating or preventing various diseases or disorders in the subject by administering to the subject an effective amount of the immunological compositions of the invention.

The present invention is also directed to methods of immunizing a subject or treating or preventing various diseases or disorders in the subject by co-administering to the subject 1) an effective amount of the LNP of the invention and 2) i) an agonist selected from a TLR agonist and a STING agonist; and/or ii) an antigen.

DETAILED DESCRIPTION OF THE INVENTION

Figure 1:
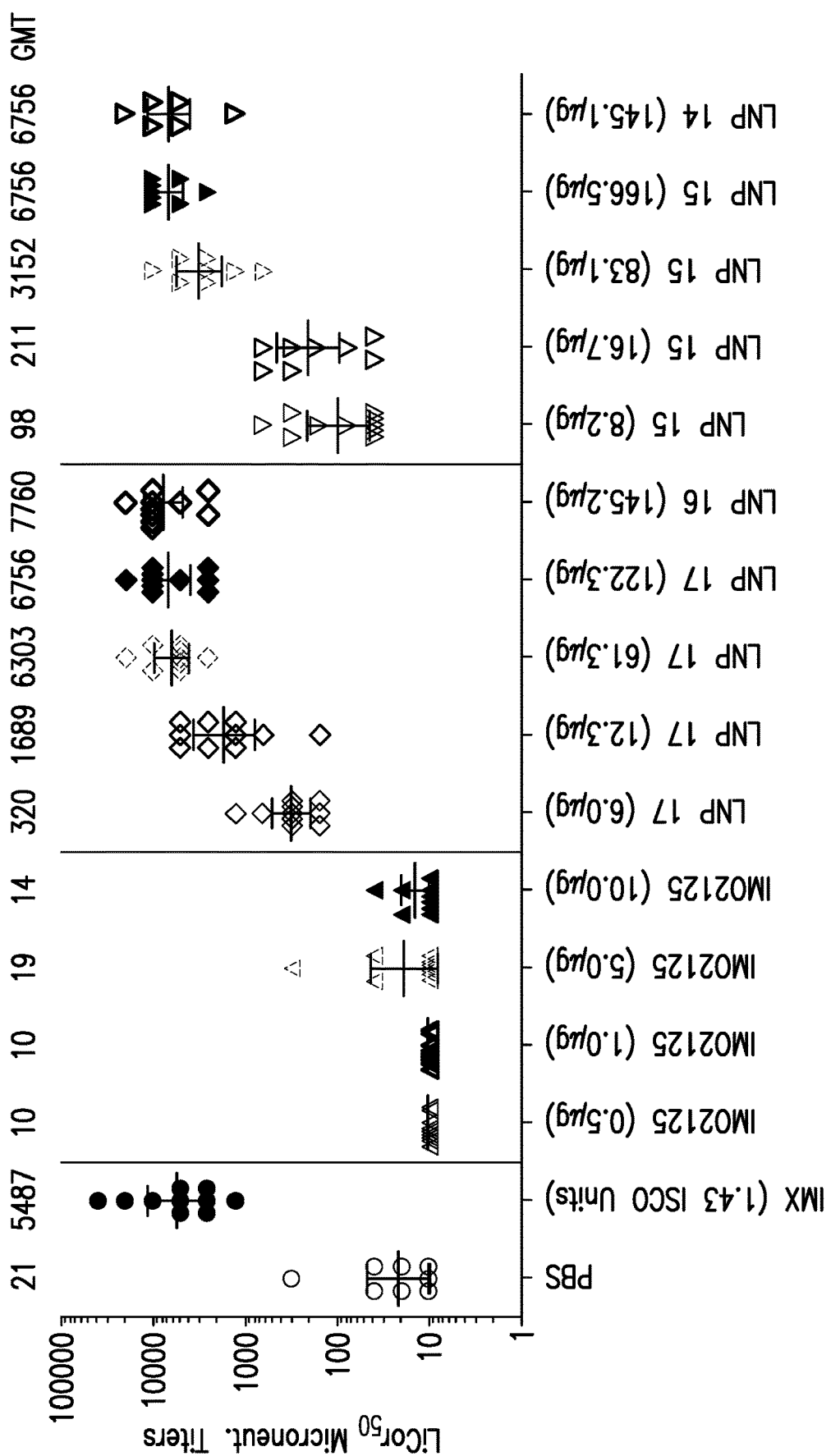
FIG. 1: DENV2 Neutralization Titers Measured 2 Weeks Post Dose 3.

The present invention is directed to immunological compositions comprising one or more antigens and a lipid nanoparticle (LNP) containing cationic lipids or ionizable cationic lipids. Such compositions can be used as vaccine adjuvants or vaccine antigen delivery agents, preferably for subunit vaccines. LNP formulations described herein demonstrate enhancements in humoral and/or cellular immunogenicity of vaccine antigens, for example, subunit vaccine antigens, when utilized alone or in combination with immunostimulatory agents (e.g., small molecule or oligonucleotide TLR agonists or STING agonists). In certain embodiments, the invention provides co-formulation of LNP systems, with or without immunostimulatory agents, with peptide or protein antigens as vaccines.

Without being bound by any theory, an advantage of this co-formulation strategy is that it is believed to enable maintenance of the antigen dose in close proximity to the adjuvant at the administration site, thereby reducing rapid dispersion of active agents, leading to enhanced immune response and potential reduction of systemic adverse effects. The present invention further identifies physical and chemical properties of these LNPs which lead to enhanced antigen efficiency and adjuvant tolerability in vivo.

LNPs, when appropriately designed, were shown to improve the delivery efficiency of antigens, e.g., subunit antigens, to target cells, enable combination and co-delivery of antigens and adjuvants, and facilitate the intracellular delivery of antigens to better potentiate desirable intracellular immune responses. The LNPs were shown to be potent vaccine adjuvants, capable of inducing strong antibody and T cell responses in preclinical rodent models when combined with recombinant protein antigens for a number of tested antigens including Dengue and HBV. As illustrated by the examples, robust adjuvant activity was demonstrated for a synthetic immunostimulatory oligonucleotides (IMO 2125 as described in Agrawal et al., 2007, Biochem Soc Trans. 35(Pt 6): 1461-7) and antigens (HBsAg and DEN-80) in vitro and in vivo. Furthermore, the T cell response had a strong CD8 component, which was superior to that induced by other adjuvants tested, such as aluminum-based adjuvant and monophosphoryl lipid A, and was of a magnitude typically only seen with live virus vaccines.

The LNP adjuvants described herein offer the potential for a number of significant advantages over existing adjuvant technologies. Potential advantages include enabling modulation of the adaptive immune response to produce more effective type of immunity (e.g., Th1/Th2) for specific antigens, yielding improved antibody titers and cell-mediated immunity, broadening responses, reducing antigen dose and/or number of doses, and enabling immunization of patients with weakened immune systems.

As used herein, "about" can refer to a variance of 0, 1, 2, 3, 4, or 5 units or ±0, 1, 5, 10, 15, 20 or 25%.

As used herein, "adjuvant" means an agent that does not constitute a specific antigen, but modifies (Th1/Th2), boosts the strength and longevity of an immune response, and/or broadens the immune response to a concomitantly administered antigen.

As used herein, "alkyl" means a straight chain, cyclic or branched saturated aliphatic hydrocarbon having the specified number of carbon atoms.

As used herein, "alkenyl" means a straight chain, cyclic or branched aliphatic hydrocarbon having the specified number of carbon atoms and one or more double bonds including but not limited to diene, triene and tetraene unsaturated aliphatic hydrocarbons.

Examples of a cyclic "alkyl" or "alkenyl" include:

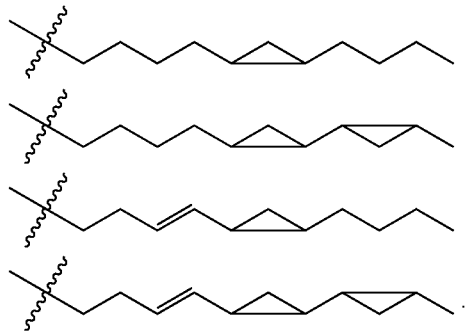

As used herein, "antigen" means any antigen that can generate one or more immune responses. The antigen may be one that generates a humoral and/or CTL immune response. The infectious agent can be a bacterium, virus, fungus, protozoan, or parasite. Antigens may be B cell or T cell antigens.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl.

As used herein, "cationic lipid" refers to any of a number of lipid species which carry a net positive charge at a selective pH, such as physiological pH.

As used herein the term "co-administration" or "co-administering" refers to administration of the LNP adjuvant and an agonist or antigen concurrently, i.e., simultaneously in time, or sequentially, i.e., administration of an LNP adjuvant, followed by administration of the agonist or antigen. That is, after administration of the LNP adjuvant, the agonist or antigen can be administered substantially immediately after the LNP adjuvant or the agonist or antigen can be administered after an effective time period after the LNP adjuvant; the effective time period is the amount of time given for realization of maximum benefit from the administration of the LNP adjuvant. An effective time period can be determined experimentally and can be generally within 1, 2, 3, 5, 10, 15, 20, 25, 30, 45 or 60 minutes.

As used herein, "halogen" means Br, Cl, F and I.

As used herein, "heterocyclyl" or "heterocycle" means a 4- to 10-membered aromatic or nonaromatic heterocycle containing from 1 to 4 heteroatoms selected from the group consisting of O, N and S, and includes bicyclic groups. "Heterocyclyl" therefore includes, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof all of which are optionally substituted with one to three substituents selected from R".

As used herein, "lipid nanoparticle" refers to any lipid composition that can be used to deliver a prophylactic product, preferably vaccine antigens, including, but not limited to, liposomes or vesicles, wherein an aqueous volume is encapsulated by amphipathic lipid bilayers (e.g., single; unilamellar or multiple; multilamellar), or, in other embodiments, wherein the lipids coat an interior comprising a prophylactic product, or lipid aggregates or micelles, wherein the lipid encapsulated therapeutic product is contained within a relatively disordered lipid mixture. Except where noted, the lipid nanoparticle does not need to have antigen incorporated therein and may be used to deliver a prophylactic product when in the same formulation.

As used herein, "polyamine" means compounds having two or more amino groups. Examples include putrescine, cadaverine, spermidine, and spermine.

Unless otherwise specified, mole % refers to a mole percent of total lipids.

Generally, the LNPs of the immunological compositions of the invention are composed of one or more cationic lipids (including ionizable cationic lipids) and one or more poly (ethyleneglycol)-lipids (PEG-lipids). In certain embodiments, the LNPs further comprise one or more non-cationic lipids. The one or more non-cationic lipids can include a phospholipid, phospholipid derivative, a sterol, a fatty acid, or a combination thereof.

Cationic lipids and ionizable cationic lipids suitable for the LNPs are described herein. Ionizable cationic lipids are characterized by the weak basicity of their lipid head groups, which affects the surface charge of the lipid in a pH-dependent manner, rendering them positively charged at acidic pH but close to charge-neutral at physiologic pH. Cationic lipids are characterized by monovalent or multivalent cationic charge on their headgroups, which renders them positively charged at neutral pH. In certain embodiments, the cationic and ionizable lipid is capable of complexing with hydrophilic bioactive molecules to produce a hydrophobic complex that partitions into the organic phase of a two-phase aqueous/organic system. It is contemplated that both monovalent and polyvalent cationic lipids may be utilized to form hydrophobic complexes with bioactive molecules.

Preferred cationic and ionizable cationic lipids for use in forming the LNPs include, but are not limited to, N,N-dioleyl-N,N-dimethylammonium chloride ("DODAC"); N-(2,3dioleyloxy)propyl)-N,N,Ntrimethylammonium chloride ("DOTMA"); N,Ndistearyl N,N-dimethylammonium bromide ('DDAB"); N-(2,3dioleoyloxy)propyl)-N,N,N-trimethylanintonium chloride ("DODAP"); 1,2 bis (oleoyloxy)-3-(trimethylammonio) propane (DOTAP); 3-(N-(N,N-dimethylaminoethane)-carbam-oyl)cholesterol ('DC-Chol"); diheptadecylamidoglycylspermidine ("DHGS") and N-(1,2-dimyristyloxyprop-3-yl)-N,N-dimethyl-N-hydoxyethyl ammonium bromide ("DMRIE"). Additionally, a number of commercial preparations of cationic lipids, as well as other components, are available which can be used in the present invention. These include, for example, LIPOFECTIN® (commercially available cationic lipid nanoparticles comprising DOTMA and 1,2dioleoyl-sn-3-phosphoethanolamine ("DOPE"), from GIBCOBRL, Grand Island, N.Y., USA); and LIPOFECTAMINE® (commercially available cationic lipid nanoparticles comprising N-(1-(2,3dioleyloxy)propyl)N-(2-(sperminecarboxamido)ethyl)-N,N-dimethylammonium trifluoroacetate ("DOSPA') and ("DOPE"), from (GIBCOBRL). The following lipids are cationic and have a positive charge at below physiological pH: DODAP, DODMA, DMDMA, 1,2-DiLinoleyloxy-N,N-dimethylaminopropane (DLinDMA), 4-(2,2-diocta-9,12-dienyl-[1,3]dioxolan-4-ylmethyl)-dimethylamine, DLinKDMA (WO 2009/132131 A1), DLin-K-C2-DMA (WO2010/042877), DLin-M-C3-DMA (WO2010/146740 and/or WO2010/105209), DLin-MC3-DMA (heptatriaconta-6,9,28,31-tetraen-19-yl 4-(dimethylamino)butanoate; Jayaraman et al., 2012, Angew. Chem. Int. Ed. Engl. 51:8529-8533), 2-{4-[(3β)-cholest-5-en-3-yloxy]butoxy}-N,N-dimethyl-3-[(9Z,12Z)-octadeca-9,12-dienlyloxyl]propan-1-amine) (CLinDMA), and the like. Other cationic lipids suitable for use in the invention include, e.g., the cationic lipids described in U.S. Pat. Nos. 5,208,036, 5,264,618, 5,279,833 and 5,283,185, and U.S. Patent Application Publication Nos. 2008/0085870 and 2008/0057080. Other cationic lipids suitable for use in the invention include, e.g., Lipids E0001-

E0118 or E0119-E0180 as disclosed in Table 6 (pages 112-139) of International Patent Application Publication No. WO2011/076807 (which also discloses methods of making, and methods of using these cationic lipids).

In certain aspects of this embodiment of the invention, the LNPs comprise one or more of the following ionizable cationic lipids: DLinDMA, DlinKC2DMA DLin-MC3-DMA, CLinDMA, or S-Octyl CLinDMA (See International Patent Application Publication No. WO2010/021865).

In certain aspects of this embodiment of the invention, LNPs comprise one or more ionizable cationic lipids described in International Patent Application Publication No. WO2011/022460 A1, or any pharmaceutically acceptable salt thereof, or a stereoisomer of any of the compounds or salts therein.

In International Patent Application Publication No. WO2011/022460 A1, the cationic lipids are illustrated by the Formula A1:

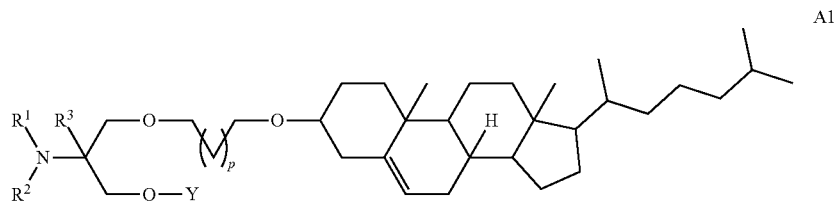

A1 wherein:

p is 1 to 8;

$R^1$ and $R^2$ are independently selected from H, $(C_1-C_{10})$ alkyl, heterocyclyl, and a polyamine, wherein said heterocyclyl and polyamine are optionally substituted with one to three substituents selected from $R^4$, or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle optionally substituted with one to three substituents selected from $R^4$;

$R^3$ is selected from H and $(C_1-C_6)$alkyl, said alkyl optionally substituted with one to three substituents selected from $R^4$;

$R^4$ is independently selected from halogen, $OR^5$, $SR^5$, CN, $CO_2R^5$ and $CON(R^5)_2$;

$R^5$ is independently selected from H, $(C_1-C_{10})$alkyl and aryl; and

Y is a $(C_4-C_{22})$alkyl, $(C_4-C_{22})$perfluoroalkyl, or a $(C_4-C_{22})$alkenyl;

or any pharmaceutically acceptable salt thereof, or a stereoisomer of any of the compounds or salts.

Exemplary ionizable cationic lipids include compounds 4-11 and 13-20 described in International Patent Application Publication No. WO2011/022460 A1, as shown in Table 1 (preceded by "1-"), or any pharmaceutically acceptable salt thereof, or a stereoisomer of any of the compounds or salts.

TABLE 1

Ionizable Cationic Lipids

| Cpd | Structure | Name |
|---|---|---|
| 1-4 | 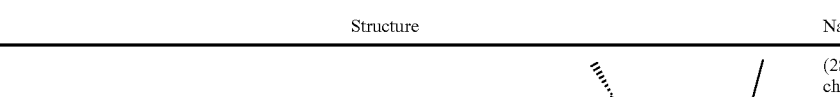 | (2S)-1-{7-[(3β)-cholest-5-en-3-yloxy]heptyloxy}-3-[(4Z)-dec-4-en-1-yloxy]-N,N-dimethyl-propan-2-amine |

TABLE 1-continued

Ionizable Cationic Lipids

| Cpd | Structure | Name |
|---|---|---|
| 1-5 | 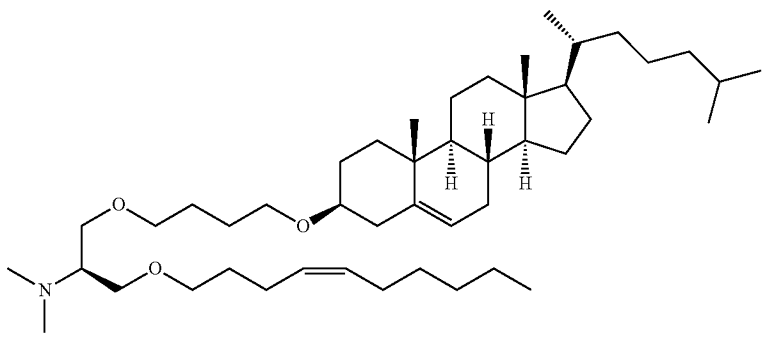 | (2R)-1-{4-[(3β)-cholest-5-en-3-yloxy]butoxy}-3-[(4Z)-dec-4-en-1-yloxy]-N,N-dimethyl-propan-2-amine |
| 1-6 | 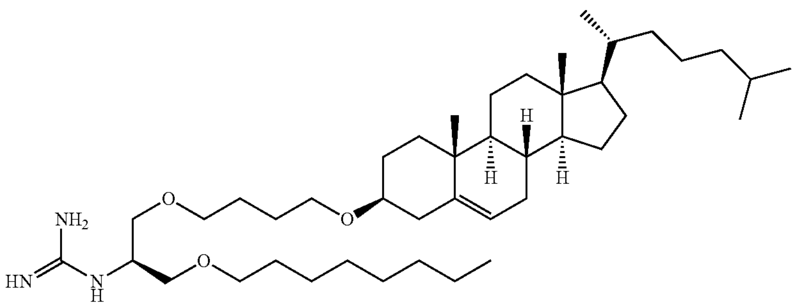 | 1-[(2R)-1-{4-[(3β)-cholest-5-en-3-yloxy]butoxy}-3-(octyloxy)propan-2-yl]guanidine |
| 1-7 | 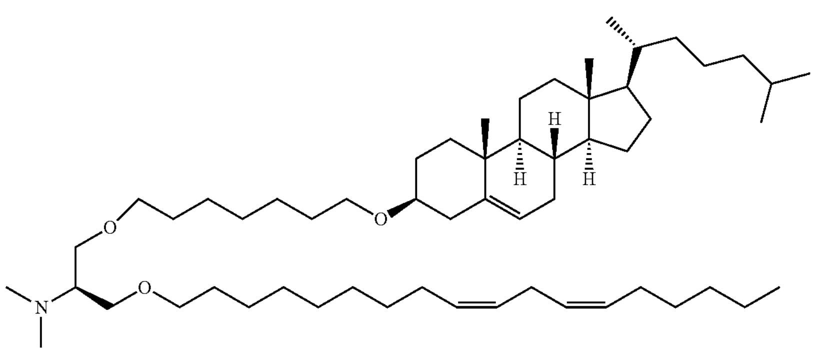 | 1-[(2R)-1-{7-[(3β)-cholest-5-en-3-yloxy]heptyloxy}-N,N-dimethyl-3-[(9Z,12Z)-octadeca-9,12-dien-1-yloxy]propan-2-amine |
| 1-8 | 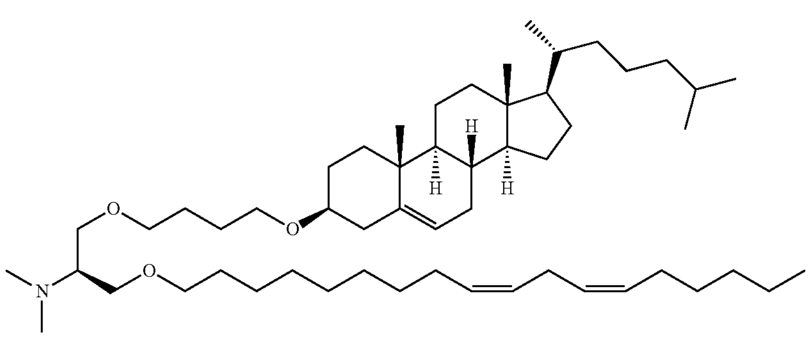 | 1-[(2R)-1-{4-[(3β)-cholest-5-en-3-yloxy]butoxy}-N,N-dimethyl-3-[(9Z,12Z)-octadeca-9,12-dien-1-yloxy]propan-2-amine |

TABLE 1-continued

Ionizable Cationic Lipids

| Cpd | Structure | Name |
| --- | --- | --- |
| 1-9 | 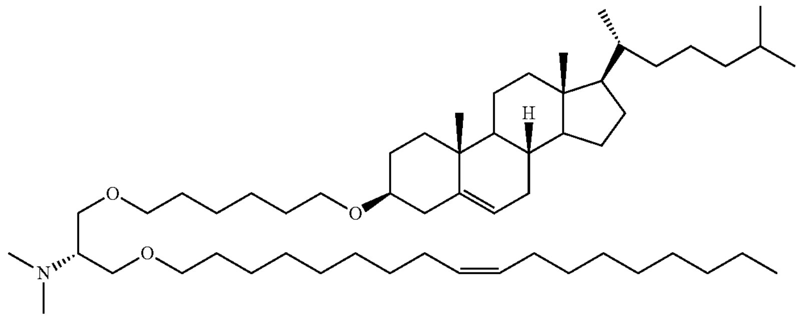 | (2S)-1-({6-[(3β))-cholest-5-en-3-yloxy]hexyl}oxy)-N,N-dimethyl-3-[(9Z)-octadec-9-en-1-yloxy]propan-2-amine |
| 1-10 | 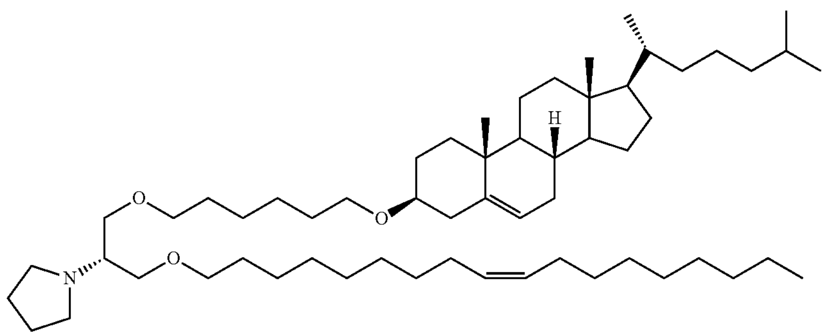 | (3β)-3-[6-{[(2S)-3-[(9Z)-octadec-9-en-1-yloxyl]-2-(pyrrolidin-1-yl)propyl]oxy}hexyl)oxy]cholest-5-ene |
| 1-11 | 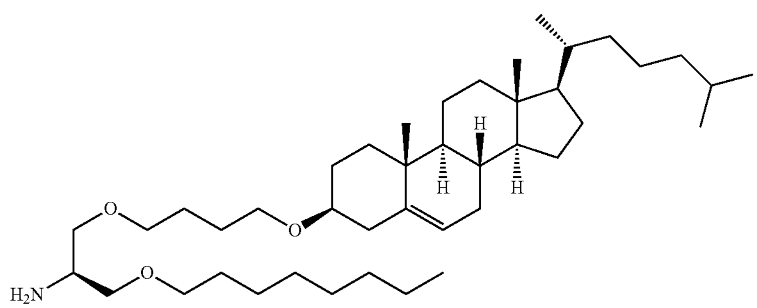 | (2R)-1-{4-[(3β)-cholest-5-en-3-yloxy]butoxy}-3-(octyloxy)propan-2-amine |
| 1-13 | 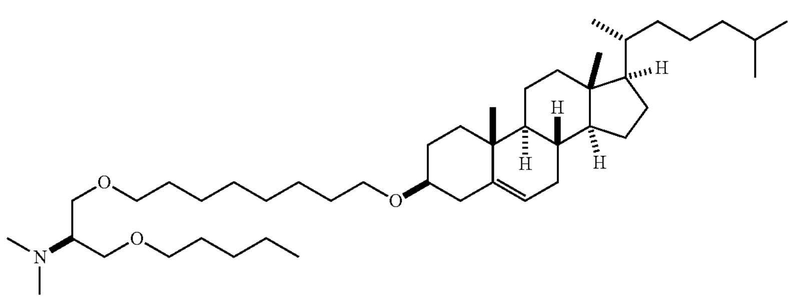 | (2R)-1-({8-[(3β)-cholest-5-en-3-yloxy]octyl}oxy)-N,N-dimethyl-3-(pentyloxy)propan-2-amine |
| 1-14 | 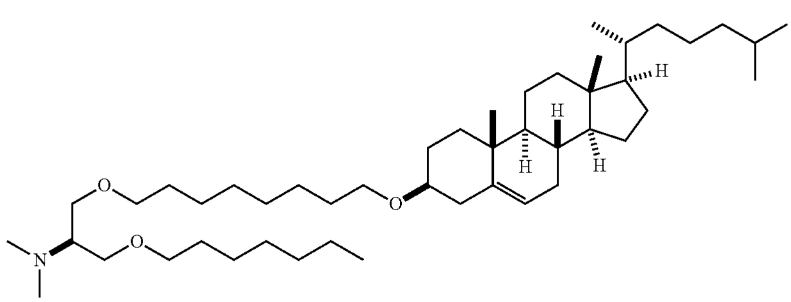 | (2R)-1-({8-[(3β)-cholest-5-en-3-yloxy]octyl}oxy)-3-(heptyloxy)N,N-dimethyl-propan-2-amine |

TABLE 1-continued

Ionizable Cationic Lipids

| Cpd | Structure | Name |
|---|---|---|
| 1-15 | 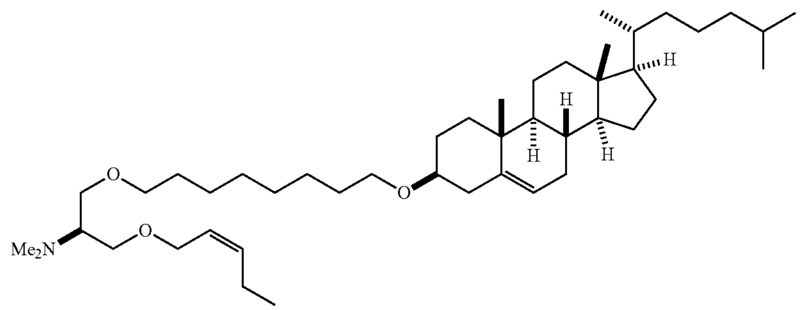 | (2R)-1-({8-[(3β)-cholest-5-en-3-yloxy]octyl}oxy)-N,N-dimethyl-3-[(2Z)-pent-2-en-1-yloxy]propan-2-amine |
| 1-16 | 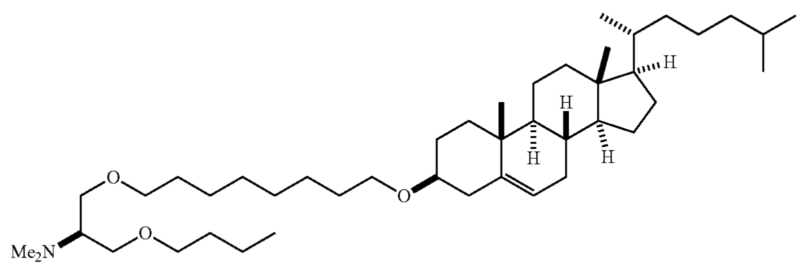 | (2S)-1-butoxy-3-({8-[(3β)-cholest-5-en-3-yloxy]octyl}oxy)-N,N-dimethyl-propan-2-amine |
| 1-17 | 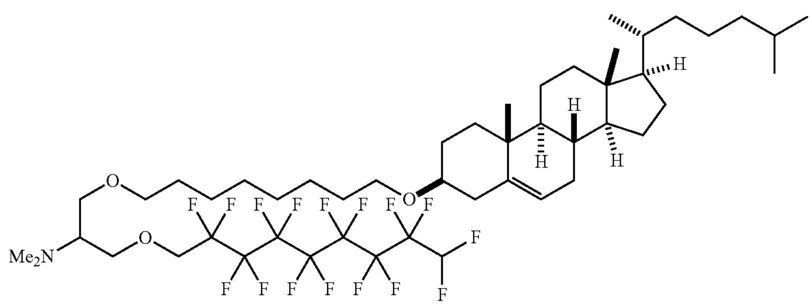 | (2S-1-({8-[(3β)-cholest-5-en-3-yloxy]octyl}oxy)-3-[2,2,3,3,4,4,5,5,6,6,7,7,8,8,9,9-hexadecafluoro-nonyl)oxy]-N,N-dimethyl-propan-2-amine |
| 1-18 | 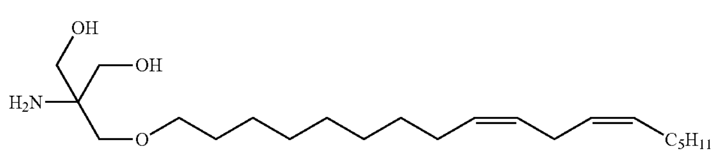 | 2-amino-2-{[(9Z,12Z)-octadeca-9,12-dien-1-yloxy]methyl}propane-1,3-diol |
| 1-19 | 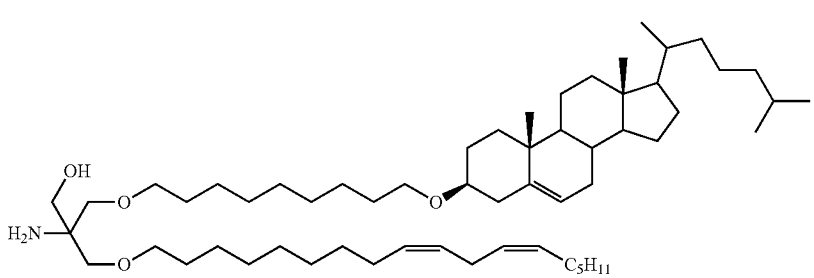 | 2-amino-3-({9-[(3β,8ξ,9ξ,14ξ,17ξ,20ξ)-cholest-5-en-3-yloxy]nonyl}oxy)-2-{[(9Z,12Z)-octadeca-9,12-dien-1-yloxy]methyl}propan-1-ol |

TABLE 1-continued

Ionizable Cationic Lipids

| Cpd | Structure | Name |
|---|---|---|
| 1-20 | 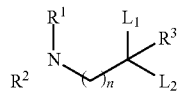 | 2-amino-3-({6-[(3β,8ξ,9ξ,14ξ,17ξ,20ξ)-cholest-5-en-3-yloxy]hexyl}oxy)-2-{[(9Z)-octadec-9-en-1-yloxy]methyl}propan-1-ol |

In one embodiment, the ionizable cationic lipid is compound 9 described in International Patent Application Publication No. WO2011/022460 A1 (designated herein as compound 1-9), or a pharmaceutically acceptable salt thereof, or a stereoisomer of the compound or its salts.

In certain aspects of this embodiment of the invention, LNPs comprise one or more low molecular weight ionizable cationic lipids described in International Patent Application Publication No. WO2012/040184, or any pharmaceutically acceptable salt thereof, or a stereoisomer of any of the compounds or salts.

In International Patent Application Publication No. WO2012/040184 A1, the cationic lipids are illustrated by the Formula A2:

$$\underset{R^2}{\overset{R^1}{N}}\underset{)_n}{\overset{L_1}{\diagdown}}\overset{R^3}{\underset{L_2}{\diagup}} \quad A2$$

wherein:

$R^1$ and $R^2$ are independently selected from H, $(C_1-C_6)$ alkyl, heterocyclyl, and polyamine, wherein said alkyl, heterocyclyl and polyamine are optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R';

$R^3$ is independently selected from H and $(C_1-C_6)$alkyl, said alkyl optionally substituted with one to three substituents selected from R';

R' is independently selected from halogen, R", OR", SR", CN, $CO_2R$" or $CON(R")_2$;

R" is independently selected from H and $(C_1-C_6)$alkyl, wherein said alkyl is optionally substituted with halogen and OH;

n is 0, 1, 2, 3, 4 or 5;

$L_1$ is selected from $C_4-C_{24}$ alkyl and $C_4-C_{24}$ alkenyl, said alkyl and alkenyl are optionally substituted with one or more substituents selected from R'; and $L_2$ is selected from $C_3-C_9$ alkyl and $C_3-C_9$ alkenyl, said alkyl and alkenyl are optionally substituted with one or more substituents selected from R';

or any pharmaceutically acceptable salt thereof, or a stereoisomer of any of the compounds or salts.

In certain embodiments, the ionizable cationic lipid is a compound having Formula A2, wherein:

$R^1$ and $R^2$ are each methyl;

$R^3$ is H;

n is 0;

$L_1$ is selected from $C_4-C_{24}$ alkyl and $C_4-C_{24}$ alkenyl; and $L_2$ is selected from $C_3-C_9$ alkyl and $C_3-C_9$ alkenyl;

or any pharmaceutically acceptable salt thereof, or a stereoisomer of any of the compounds or salts.

Exemplary ionizable cationic lipids are compounds 1-44 described in International Patent Application Publication No. WO2012/040184, as shown in Table 2 (preceded by "2-", or any pharmaceutically acceptable salt thereof, or a stereoisomer of any of the compounds or salts.

TABLE 2

Additional Ionizable Cationic Lipids

| Cpd. | Structure | Name |
|---|---|---|
| 2-1 | 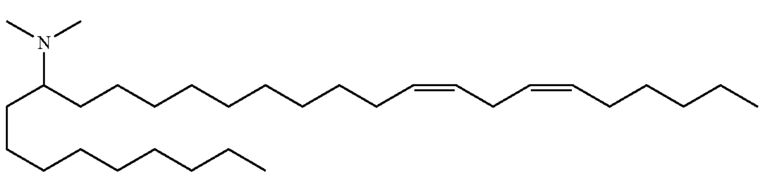 [SMILES: CCCCC/C=C\C/C=C\CCCCCCCCCC(CCCCCCCCC)N(C)C] | (20Z,23Z)-N,N-dimethylnonacosa-20,23-dien-10-amine |

TABLE 2-continued

Additional Ionizable Cationic Lipids

| Cpd. | Structure | Name |
|---|---|---|
| 2-2 | 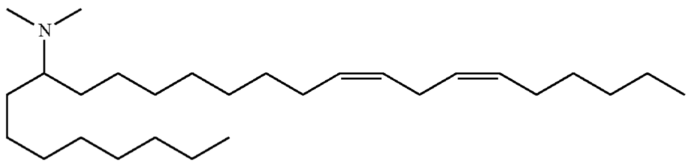 [SMILES: CCCCC/C=C\C/C=C\CCCCCCCC(CCCCCCCC)N(C)C] | (17Z,20Z)-N,N-dimethylhexacosa-17,20-dien-9-amine |
| 2-3 | 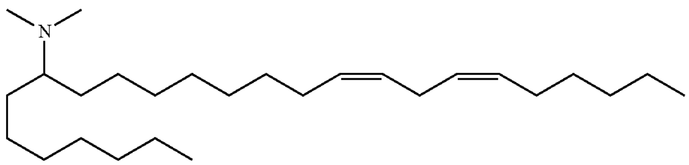 [SMILES: CCCCC/C=C\C/C=C\CCCCCCCC(CCCCCCC)N(C)C] | (16Z,19Z)-N,N-dimethylpentacosa-16,19-dien-8-amine |
| 2-4 | 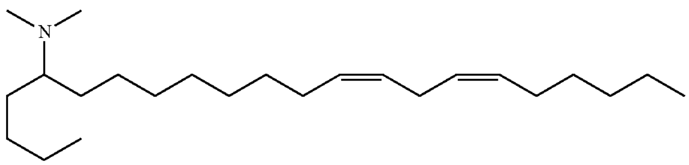 [SMILES: CCCCC/C=C\C/C=C\CCCCCCCC(CCCC)N(C)C] | (13Z,16Z)-N,N-dimethyldocosa-13,16-dien-5-amine |
| 2-5 | 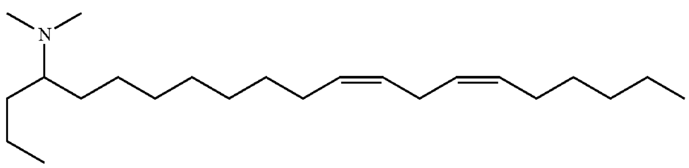 | (12Z,15Z)-N,N-dimethyl-henicosa-12,15-dien-4-amine |
| 2-6 | 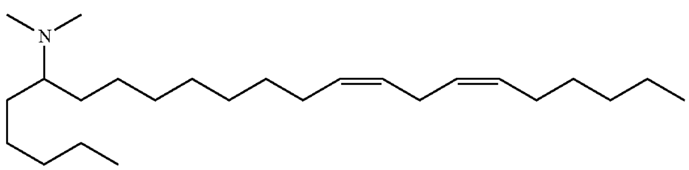 [SMILES: CCCCC/C=C\C/C=C\CCCCCCCC(CCCCC)N(C)C] | (14Z,17Z)-N,N-dimethyltricosa-14,17-dien-6-amine |
| 2-7 | 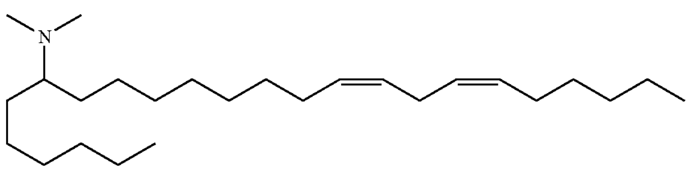 [SMILES: CCCCC/C=C\C/C=C\CCCCCCCC(CCCCCC)N(C)C] | (15Z,18Z)-N,N-dimethyltetracosa-15,18-dien-7-amine |
| 2-8 | 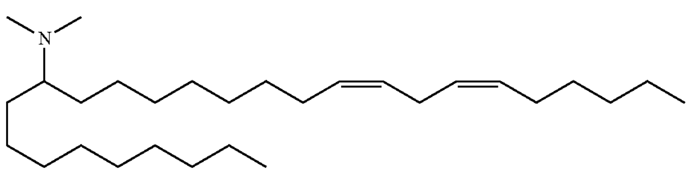 [SMILES: CCCCC/C=C\C/C=C\CCCCCCCC(CCCCCCCCC)N(C)C] | (18Z,21Z)-N,N-dimethylheptacosa-18,21-dien-10-amine |
| 2-9 | 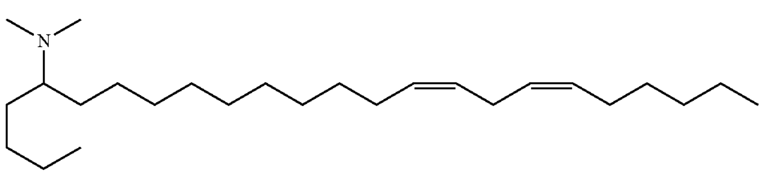 [SMILES: CCCCC/C=C\C/C=C\CCCCCCCCCC(CCCC)N(C)C] | (15Z,18Z)-N,N-dimethyltetracosa-15,18-dien-5-amine |
| 2-10 | 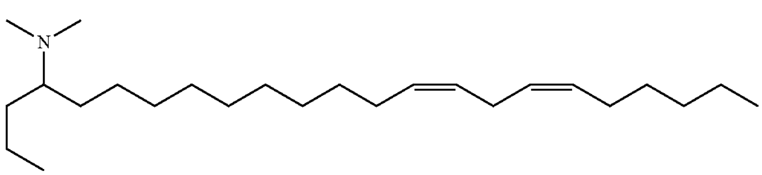 | (14Z,17Z)-N,N-dimethyltricosa-14,17-dien-4-amine |

TABLE 2-continued

Additional Ionizable Cationic Lipids

| Cpd. | Structure | Name |
|---|---|---|
| 2-11 | 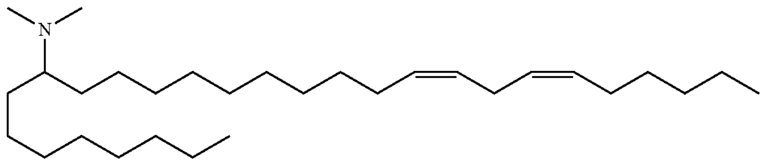 [SMILES: CCCCC/C=C\C/C=C\CCCCCCCCCC(CCCCCCCC)N(C)C] | (19Z,22Z)-N,N-dimethyloctacosa-19,22-dien-9-amine |
| 2-12 | 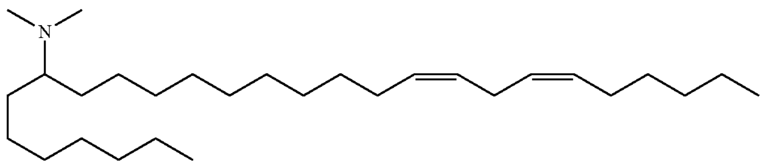 [SMILES: CCCCC/C=C\C/C=C\CCCCCCCCCC(CCCCCCC)N(C)C] | (18Z,21Z)-N,N-dimethylheptacosa-18,21-dien-8-amine |
| 2-13 | 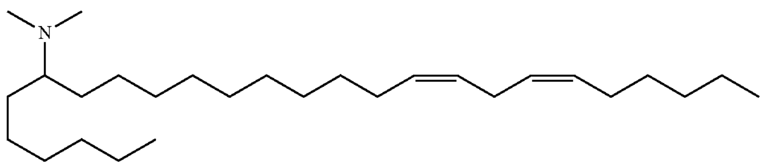 [SMILES: CCCCC/C=C\C/C=C\CCCCCCCCCC(CCCCCC)N(C)C] | (17Z,20Z)-N,N-dimethylhexacosa-17,20-dien-7-amine |
| 2-14 | 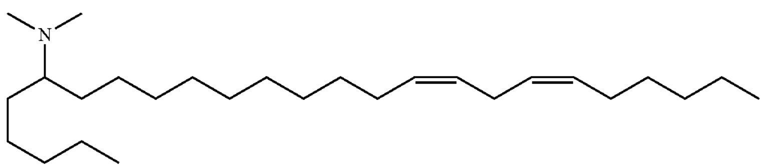 [SMILES: CCCCC/C=C\C/C=C\CCCCCCCCCC(CCCCC)N(C)C] | (16Z,19Z)-N,N-dimethylpentacosa-16,19-dien-6-amine |
| 2-15 | 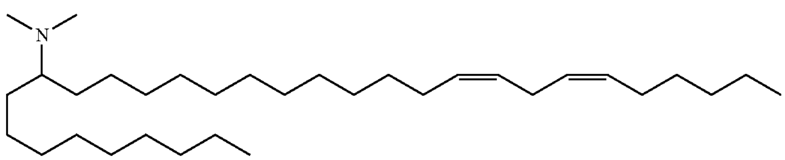 [SMILES: CCCCC/C=C\C/C=C\CCCCCCCCCCCC(CCCCCCCCC)N(C)C] | (22Z,25Z)-N,N-dimethylhentriaconta-22,25-dien-10-amine |
| 2-16 | 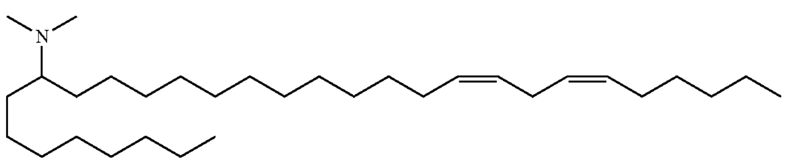 [SMILES: CCCCC/C=C\C/C=C\CCCCCCCCCCCC(CCCCCCCC)N(C)C] | (21Z,24Z)-N,N-dimethyltriaconta-21,24-dien-9-amine |
| 2-17 | 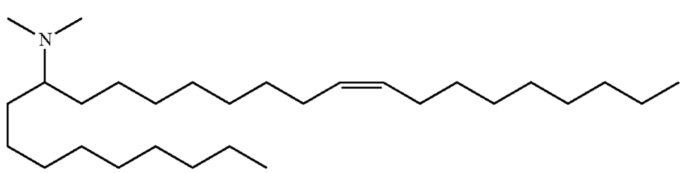 [SMILES: CCCCCCCC/C=C\CCCCCCCC(CCCCCCCCC)N(C)C] | (18Z)-N,N-dimethylheptacos-18-en-10-amine |
| 2-18 | 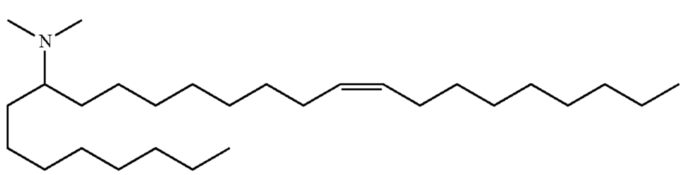 [SMILES: CCCCCCCC/C=C\CCCCCCCC(CCCCCCCC)N(C)C] | (17Z)-N,N-dimethylhexacos-17-en-9-amine |
| 2-19 | 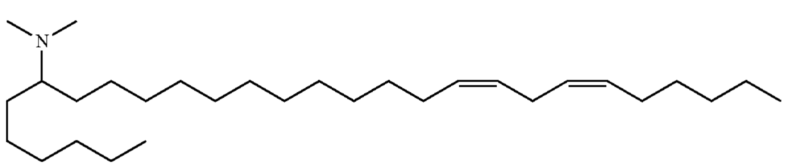 [SMILES: CCCCC/C=C\C/C=C\CCCCCCCCCCCC(CCCCCC)N(C)C] | (19Z,22Z)-N,N-dimethyloctacosa-19,22-dien-7-amine |

TABLE 2-continued

Additional Ionizable Cationic Lipids

| Cpd. | Structure | Name |
|---|---|---|
| 2-20 | 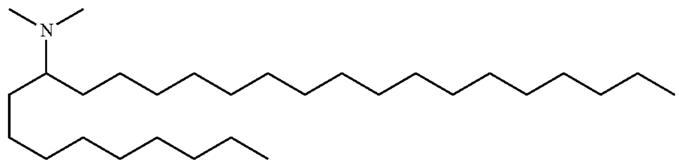 [SMILES: CCCCCCCCCCCCCCCCCC(CCCCCCCCC)N(C)C] | N,N-dimethyl-heptacosan-10-amine |
| 2-21 | 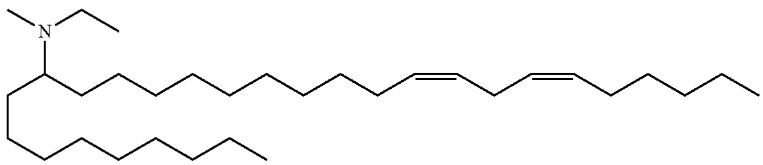 [SMILES: CCCCC/C=C\C/C=C\CCCCCCCCCC(CCCCCCCCC)N(C)CC] | (20Z,23Z)-N-ethyl-N-methyl-nonacosa-20,23-dien-10-amine |
| 2-22 | 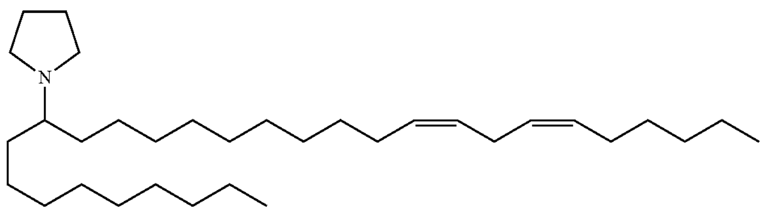 [SMILES: CCCCC/C=C\C/C=C\CCCCCCCCCC(CCCCCCCCC)N1CCCC1] | 1-[(11Z,14Z)-1-nonylicosa-11,14-dien-1-yl]pyrrolidine |
| 2-23 | 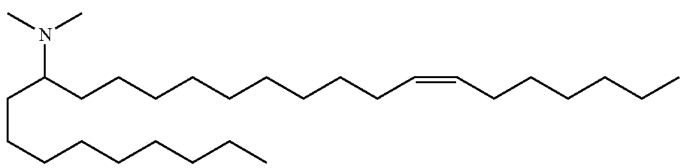 [SMILES: CCCCCC/C=C\CCCCCCCCCC(CCCCCCCCC)N(C)C] | (20Z)-N,N-dimethylheptacos-20-en-10-amine |
| 2-24 | 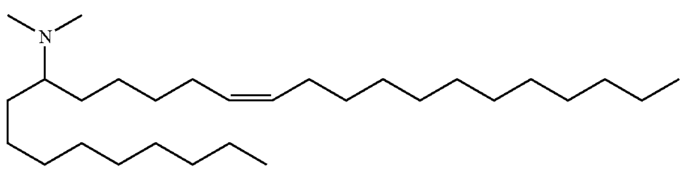 [SMILES: CCCCCCCCCCC/C=C\CCCCC(CCCCCCCCC)N(C)C] | (15Z)-N,N-dimethylheptacos-15-en-10-amine |
| 2-25 | 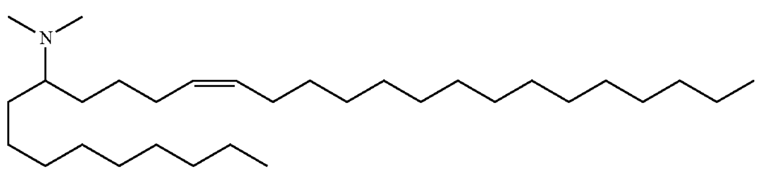 [SMILES: CCCCCCCCCCCCCC/C=C\CCCC(CCCCCCCCC)N(C)C] | (14Z)-N,N-dimethylnonacos-14-en-10-amine |
| 2-26 | 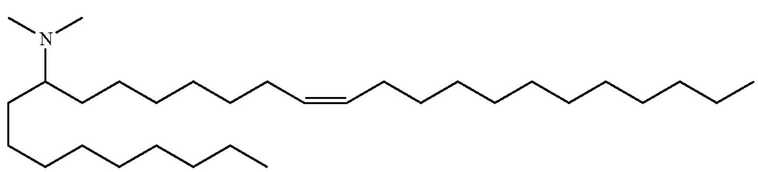 [SMILES: CCCCCCCCCCC/C=C\CCCCCCC(CCCCCCCCC)N(C)C] | (17Z)-N,N-dimethylnonacos-17-en-10-amine |
| 2-27 | 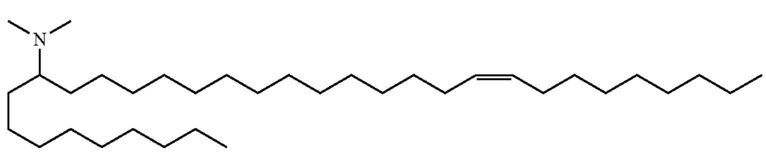 [SMILES: CCCCCCCC/C=C\CCCCCCCCCCCCCC(CCCCCCCCC)N(C)C] | (24Z)-N,N-dimethyltritriacont-24-en-10-amine |
| 2-28 | 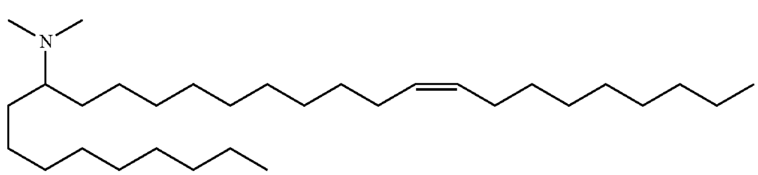 [SMILES: CCCCCCCC/C=C\CCCCCCCCCC(CCCCCCCCC)N(C)C] | (20Z)-N,N-dimethylnonacos-20-en-10-amine |

TABLE 2-continued

Additional Ionizable Cationic Lipids

| Cpd. | Structure | Name |
|---|---|---|
| 2-29 | 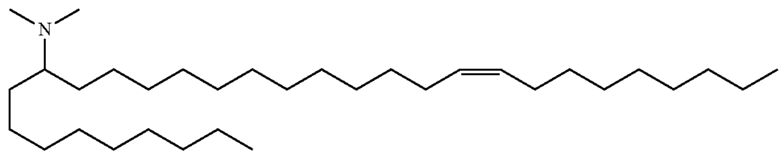 [SMILES: CCCCCCCC/C=C\CCCCCCCCCCCC(CCCCCCCCC)N(C)C] | (22Z)-N,N-dimethylhentriacont-22-en-10-amine |
| 2-30 | 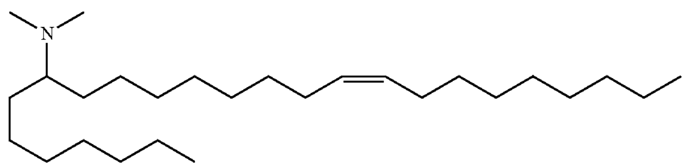 [SMILES: CCCCCCCC/C=C\CCCCCCCC(CCCCCCC)N(C)C] | (16Z)-N,N-dimethylpentacos-16-en-8-amine |
| 2-31 | 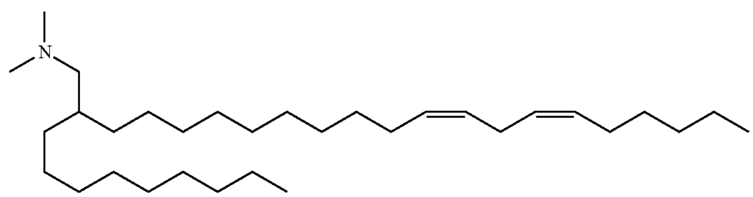 [SMILES: CCCCC/C=C\C/C=C\CCCCCCCCCC(CCCCCCCCC)CN(C)C] | (12Z,15Z)-N,N-dimethyl-2-nonylhenicosa-12,15-dien-1-amine |
| 2-32 | 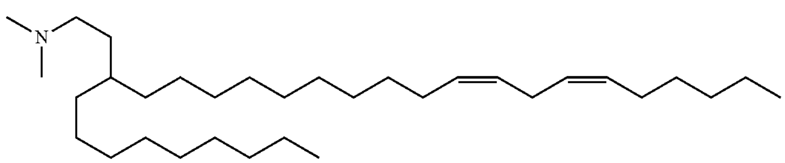 [SMILES: CCCCC/C=C\C/C=C\CCCCCCCCCC(CCCCCCCCC)CCN(C)C] | (13Z,16Z)-N,N-dimethyl-3-nonyldocosa-13,16-dien-1-amine |
| 2-33 | 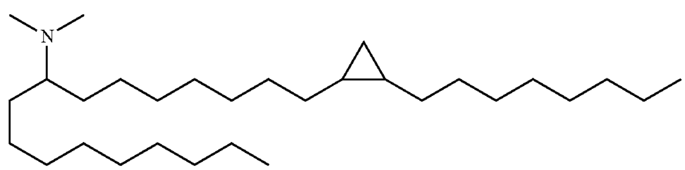 [SMILES: CCCCCCCCCC(CCCCCCCC1CC1CCCCCCCC)N(C)C] | N,N-dimethyl-1-[(1S,2R)-2-octylcyclopropyl]heptadecan-8-amine |
| 2-34 | 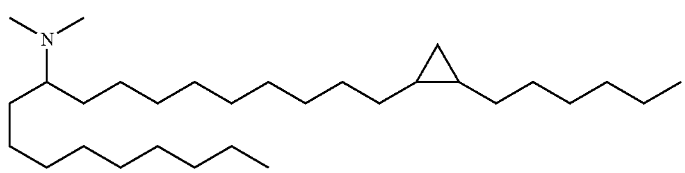 [SMILES: CCCCCCCCCC(CCCCCCCCCC1CC1CCCCCC)N(C)C] | 1-[(1S,2R)-2-hexylcyclopropyl]-N,N-dimethylnonadecan-10-amine |
| 2-35 | 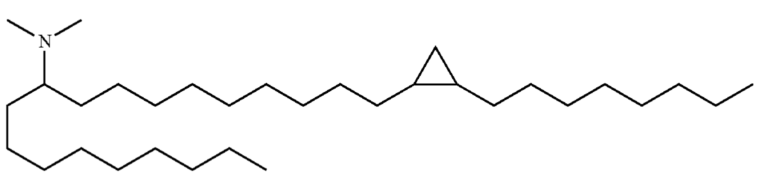 [SMILES: CCCCCCCCCC(CCCCCCCCCC1CC1CCCCCCCC)N(C)C] | N,N-dimethyl-1-[(1S,2R)-2-octylcyclopropyl]nonadecan-10-amine |
| 2-36 | 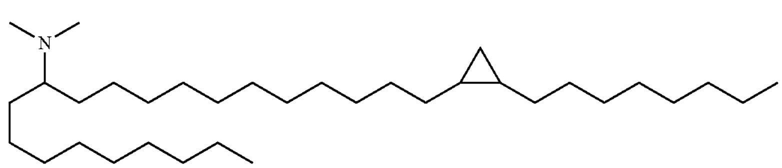 [SMILES: CCCCCCCCCC(CCCCCCCCCCCC1CC1CCCCCCCC)N(C)C] | N,N-dimethyl-21-[(1S,2R)-2-octylcyclopropyl]henicosan-10-amine |

TABLE 2-continued

Additional Ionizable Cationic Lipids

| Cpd. | Structure | Name |
|---|---|---|
| 2-37 | 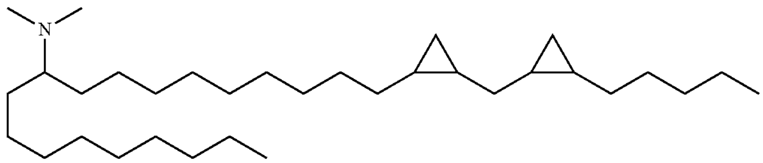 [SMILES: CCCCCCCCCC(CCCCCCCCCC1CC1CC1CC1CCCCC)N(C)C] | N,N-dimethyl-1-[(1S,2S)-2-{[(1R,2R)-2-pentylcyclopropyl]methyl}cyclopropyl]nonadecan-10-amine |
| 2-38 | 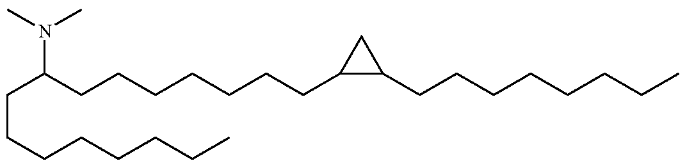 [SMILES: CCCCCCCCC1CC1CCCCCCCC(CCCCCCCC)N(C)C] | N,N-dimethyl-1-[(1S,2R)-2-octylcyclopropyl]hexadecan-8-amine |
| 2-39 | 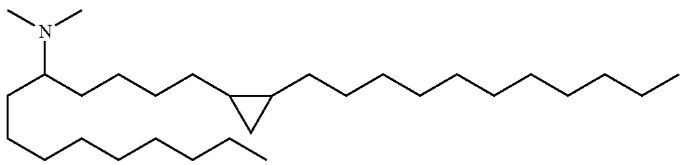 [SMILES: CCCCCCCCCCCC1CC1CCCCC(CCCCCCCCC)N(C)C] | N,N-dimethyl-1-[(1R,2S)-2-undecylcyclopropyl]tetradecan-5-amine |
| 2-40 | 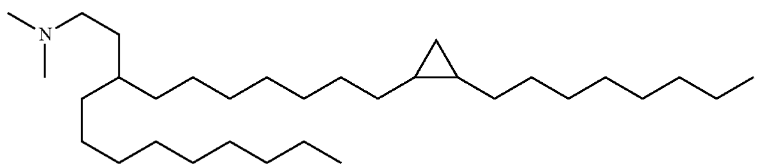 [SMILES: CCCCCCCCCC(CCCCCCCC1CC1CCCCCCCC)CCN(C)C] | N,N-dimethyl-3-{7-[(1S,2R)-2-octylcyclopropyl]heptyl}dodecan-1-amine |
| 2-41 | 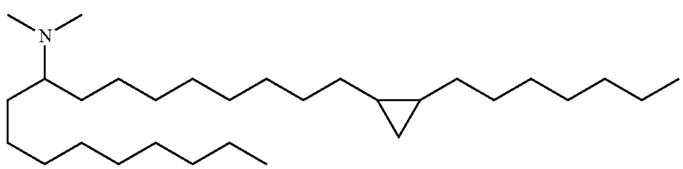 [SMILES: CCCCCCCCCC(CCCCCCCCC1CC1CCCCCCC)N(C)C] | 1-[(1R,2S)-2-heptylcyclopropyl]-N,N-dimethyloctadecan-9-amine |
| 2-42 | 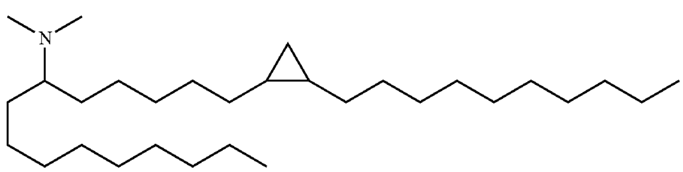 [SMILES: CCCCCCCCCCC1CC1CCCCCC(CCCCCCCCC)N(C)C] | 1-[(1S,2R)-2-decylcyclopropyl]-N,N-dimethylpentadecan-6-amine |
| 2-43 | 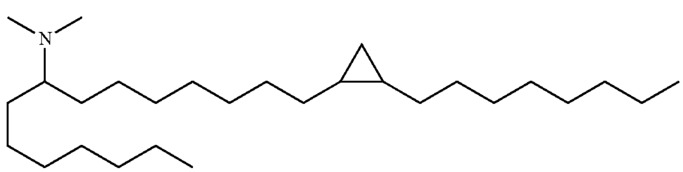 [SMILES: CCCCCCCCC1CC1CCCCCCCC(CCCCCCC)N(C)C] | N,N-dimethyl-1-[(1S,2R)-2-octylcyclopropyl]pentadecan-8-amine |
| 2-44 | 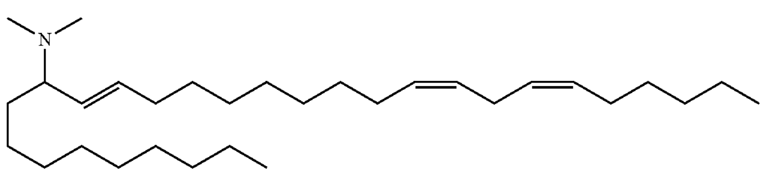 [SMILES: CCCCC/C=C\C/C=C\CCCCCCC/C=C/C(CCCCCCCCC)N(C)C] | (11E,20Z,23Z)-N,N-dimethylnonacosa-11,20,23-trien-10-amine |

In certain embodiments, the ionizable cationic lipids are compounds 32 and 33 described in International Patent Application Publication No. WO2012/040184 (designated herein as compounds 2-32 and 2-33, respectively), or a pharmaceutically acceptable salt thereof, or a stereoisomer of any of the compounds or its salts.

The LNPs may also comprise any combination of two or more of the cationic lipids described herein.

In certain aspects, the cationic lipid typically comprises from about 0.1 to about 99.9 mole % of the total lipid present in said particle. In certain aspects, the cationic lipid can comprise from about 80 to about 99.9% mole %. In other aspects, the cationic lipid comprises from about 2% to about 70%, from about 5% to about 50%, from about 10% to about 45%, from about 20% to about 99.8%, from about 30% to about 70%, from about 34% to about 59%, from about 20% to about 40%, or from about 30% to about 40% (mole %) of the total lipid present in said particle.

The LNPs described herein can further comprise a non-cationic lipid, which can be any of a variety of neutral uncharged, zwitterionic or anionic lipids capable of producing a stable complex. They are preferably neutral, although they can be negatively charged. Examples of noncationic lipids useful in the present invention include phospholipid-related materials, such as natural phospholipids, synthetic phospholipid derivatives, fatty acids, sterols, and combinations thereof. Natural phospholipids include phosphatidylcholine (PC), phosphatidylethanolamine (PE), and phosphatidylglycerol (PG), phosphatidylserine (PS), phosphatidylinositol (PI), Phosphatidic acid (phosphatidate) (PA), dipalmitoylphosphatidylcholine, monoacyl-phosphatidylcholine (lyso PC), 1-palmitoyl-2-oleoyl-sn-glycero-3-phosphocholine (POPC), N-Acyl-PE, phosphoinositides, and phosphosphingolipids. Phospholipid derivatives include phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), and phosphatidylserine (DOPS). Fatty acids include C14:0, palmitic acid (C16:0), stearic acid (C18:0), oleic acid (C18:1), linoleic acid (C18:2), linolenic acid (C18:3), and arachidonic acid (C20:4), C20:0, C22:0 and lethicin.

In certain embodiments of the invention the non-cationic lipid is selected from lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylet-hanolamine (POPE) and dioleoyl-phosphatidylethanolamine 4-(N-maleimidomethyl)-cyclohexane-1-carboxylate (DOPE-mal). Noncationic lipids also include sterols such as cholesterol, stigmasterol or stigmastanol. Cholesterol is known in the art. See U.S. Patent Application Publication Nos: U.S. 2006/0240554 and U.S. 2008/0020058. In certain embodiments, the LNP comprise a combination of a phospholipid and a sterol.

Where present, the non-cationic lipid typically comprises from about 0.1% to about 65%, about 2% to about 65%, about 10% to about 65%, or about 25% to about 65% expressed as mole percent of the total lipid present in the LNP. The LNPs described herein further include a polyethyleneglycol (PEG) lipid conjugate ("PEG-lipid") which may aid as a bilayer stabilizing component. The lipid component of the PEG lipid may be any non-cationic lipid described above including natural phospholipids, synthetic phospholipid derivatives, fatty acids, sterols, and combinations thereof. In certain embodiments of the invention, the PEG-lipids include, PEG coupled to dialkyloxypropyls (PEG-DAA) as described in, e.g., International Patent Application Publication No. WO 05/026372, PEG coupled to diacylglycerol (PEG-DAG) as described in, e.g., U.S. Patent Publication Nos. 20030077829 and 2005008689; PEG coupled to phosphatidylethanolamine (PE) (PEG-PE), or PEG conjugated to 1,2-Di-O-hexadecyl-sn-glyceride (PEG-DSG), or any mixture thereof (see, e.g., U.S. Pat. No. 5,885,613).

In one embodiment, the PEG-DAG conjugate is a dilaurylglycerol (C12)-PEG conjugate, a PEG dimyristylglycerol (C14)conjugate, a PEG-dipalmitoylglycerol (C16) conjugate, a PEG-dilaurylglycamide (C12) conjugate, a PEG-dimyristylglycamide (C14) conjugate, a PEG-dipalmitoylglycamide (C16) conjugate, or a PEG-disterylglycamide (C18). Those of skill in the art will readily appreciate that other diacylglycerols can be used in the PEG-DAG conjugates.

In certain embodiments, PEG-lipids include, but are not limited to, PEG-dimyristolglycerol (PEG-DMG), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), and PEG-1,2-dimyristyloxlpropyl-3-amine (PEG-c-DMA).

In certain embodiments, the PEG-lipid is PEG coupled to dimyristoylglycerol (PEG-DMG), e.g., as described in Abrams et al., 2010, Molecular Therapy 18(1):171, and U.S. Patent Application Publication Nos. US 2006/0240554 and US 2008/0020058.

In certain embodiments, the PEG-lipid, such as a PEG-DAG, PEG-cholesterol, PEG-DMB, comprises a polyethylene glycol having an average molecular weight ranging of about 500 daltons to about 10,000 daltons, of about 750 daltons to about 5,000 daltons, of about 1,000 daltons to about 5,000 daltons, of about 1,500 daltons to about 3,000 daltons or of about 2,000 daltons. In certain embodiments, the PEG-lipid comprises PEG400, PEG1500, PEG2000 or PEG5000.

The acyl groups in any of the lipids described above are preferably acyl groups derived from fatty acids having about C10 to about C24 carbon chains. In one embodiment, the acyl group is lauroyl, myristoyl, palmitoyl, stearoyl or oleoyl.

The PEG-lipid conjugate typically comprises from about 0.1% to about 15%, from about 0.5% to about 20%, from about 1.5% to about 18%, from about 4% to about 15%, from about 5% to about 12%, from about 1% to about 4%, or about 2% expressed as a mole % of the total lipid present in said particle.

In certain embodiments of the invention, the LNPs comprise one or more cationic lipids, cholesterol and 1,2-Dimyristoyl-sn-glycerol methoxypolyethylene glycol (PEG-DMG).

In certain embodiments the invention, the LNPs comprise one or more cationic lipids, cholesterol, 1,2-Distearoyl-sn-glycero-3-phosphocholine (DSPC), and 1,2-Dimyristoyl-sn-glycerol methoxypolyethylene glycol (PEG-DMG).

In certain embodiments of the invention, the LNPs comprise lipid compounds assembled within the following molar ratios:

Cationic Lipid (20-99.8 mole %)
Non-cationic lipid (0.1-65 mole %) and
PEG-DMG (0.1-20 mole %).

In certain embodiments of the invention, the LNPs comprise lipid compounds assembled within the following molar ratios:

Cationic Lipid (30-70 mole %)
Non-cationic lipid (25-65 mole %) and
PEG-DMG (1-5 mole %).

In certain aspects of this embodiment, the non-cationic lipid is cholesterol. Exemplary LNPs may include cationic lipid/cholesterol/PEG-DMG at about the following molar ratios: 68/29/4; 60/38/2; 51/45/4; and 51/43.5/5.5.

In certain aspects of this embodiment, the non-cationic lipid is cholesterol and DSPC. Exemplary LNPs may include cationic lipid/cholesterol/DSPC/PEG-DMG at about the following molar ratios: 59/30/10/1; 58/30/10/2; 43/41/15/1; 42/41/15/2; 40/48/10/2; 39/41/19/1; 38/41/19/2; 34/41/24/1; and 33/41/24/2.

In certain embodiments of the invention, the LNPs may further comprise one or more agonists for Toll-like receptors (TLR) or Stimulator of Interferon Genes (STING). See, e.g., Lahiri et al., 2008, Vaccine 26:6777-83; Archer et al., 2014, PLoS Pathol 10:e1003861; Corrales et al., 2013, J Immunotherapy Cancer 1 (Suppl 1):O15; Gray et al., 2012, Cellular Immunology 278:113-119; Li et al., 2013, Science 341:1390-1394. Immunogenic compositions of the invention may comprise a TLR agonist selected from TLR1, TLR2, TLR3, TLR4, TLR5, TLR6, TLR7, TLR8 or TLR9 agonist or a combination thereof. Immunogenic compositions of the invention may comprise a STING agonist selected from 3'3'-cGAMP, 2'3'-cGAMP, 2'2'-cGAMP, c-di-AMP, c-di-GMP, c-di-IMP, c-di-UMP, DMXAA, acylated conjugates thereof, prodrugs thereof, or any combination thereof.

In one embodiment, a TLR agonist is used that is capable of causing a signaling response through TLR1. The TLR agonist capable of causing a signaling response through TLR1 can be selected from: Tri-acylated lipopeptides (LPs); phenol-soluble modulin; *Mycobacterium tuberculosis* LP; 5-(2,3-bis(palmitoyloxy)-(2-RS)-propyl)-N-palmitoyl-(R)-Cys-(S)-Ser-(S)-Lys(4)-OH, trihydrochloride (Pam3Cys) LP which mimics the acetylated amino terminus of a bacterial lipoprotein and OspA LP from *Borrelia burgdorfei*.

In one embodiment, the TLR agonist is a TLR2 agonist. The TLR agonist capable of causing a signaling response through TLR2 can be selected from one or more of a lipoprotein, a peptidoglycan, a bacterial lipopeptide from *M. tuberculosis, B. burgdorferi T pallidum*; peptidoglycans from species including *Staphylococcus aureus*; lipoteichoic acids, mannuronic acids, *Neisseria* porins, bacterial fimbriae, *Yersina* virulence factors, CMV virions, measles haemagglutinin, and zymosan from yeast. In one aspect of this embodiment, the TLR2 agonist is the synthetic lipopeptide Pam2Cys or Pam3Cys-Lip. See, e.g., Zeng et al., 2010, Amino Acids 39:471-80 and Fisette et al., 2003, J Biol Chem 278:46252.

In one embodiment, a TLR agonist is used that is capable of causing a signalling response through TLR3. The TLR agonist capable of causing a signaling response through TLR3 can be selected from immuno stimulatory RNA molecules, such as but not limited to double stranded RNA (dsRNA), polyinosinic-polycytidylic acid (Poly IC) or poly Lpoly C12U (available as AMPLIGEN®, and/or those disclosed in Heil et al., 2004, Science 303(5663):1526-1529; International Patent Application Publication Nos. WO 2008033432 A2, WO 2007062107 A2, WO 2005097993 A2 and WO 2003086280 A2; U.S. Patent Application Publication No. US 2006241076.

In an embodiment the toll-like receptor agonist is a TLR4 agonist, such as an agonist such as a lipid A derivative particularly monophosphoryl lipid A (MPL A) or 3 Deacylated monophoshoryl lipid A (3D-MPL). 3D-MPL is available under the trademark MPL® by GlaxoSmithKline Biologicals North America and primarily promotes CD4+ T cell responses with an IFN-g (Th1) phenotype. Chemically it is a mixture of 3-deacylated monophosphoryl lipid A with 3, 4, 5 or 6 acylated chains. Synthetic derivatives of lipid A are known and thought to be TLR4 agonists including, but not limited to: OM174 (2-deoxy-6-O-[2-deoxy-2-[(R)-3-dodecanoyloxytetra-decanoylamino]-4-O-phosphono-β;-D-glucopyranosyl]-2-[(R)-3-hydroxytetrade canoylamino]-α-D-glucopyranosyldihydrogenphosphate) (International Patent Application Publication No. WO 95/14026); OM 294 DP (3S, 9R)-3-[(R)-dodecanoyloxytetradecanoylamino]-4-oxo-5-aza-9(R)-[(R)-3-hydroxytetra decanoylamino]decan-1,10-diol, 1,10-bis(dihydrogenophosphate) (International Patent Publication Nos. WO 99/64301 and WO 00/0462); OM 197 MP-Ac DP (3S,9R)-3-[(R)-dodecanoyloxytetradecanoylamino]-4-oxo-5-aza-9-[(R)-3-hydroxytetradec anoylamino]decan-1,10-diol, 1-dihydrogenophosphate 10-(6-aminohexanoate) (International Patent Application Publication No. WO 01/46127).

Other TLR4 ligands which may be used are alkyl Glucosaminide phosphates (AGPs) such as those disclosed in International Patent Application No. WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants. In a particular embodiment of the invention the adjuvant is a TLR4 agonist which is an AGP. In a particular embodiment, the TLR4 agonist is CRX524 or CRX527. CRX527 and CRX524 have been described previously. See U.S. Pat. No. 6,113,918; and International Patent Application Nos. WO 2006/012425 and WO 2006/016997). In a particular embodiment, the TLR4 agonist is Glucopyranosyl Lipid Adjuvant (GLA). See, e.g., Lambert et al., 2012, PLoS One 7:e51618.

Other suitable TLR4 ligands, capable of causing a signaling response through TLR4 are, for example, lipopolysaccharide (LPS) from gram-negative bacteria and its derivatives, or fragments thereof, in particular a non-toxic derivative of LPS (such as 3D-MPL). Other suitable TLR4 agonists are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, muramyl dipeptide (MDP), F protein of respiratory syncytial virus, VSV-G, or HMGB-1.

In one embodiment, a TLR agonist is used that is capable of causing a signalling response through TLR5. The TLR agonist capable of causing a signaling response through TLR5 can be a bacterial flagellin or a variant thereof. The flagellin can include a polypeptide selected from the group consisting of *H. pylori, S. typhimurium, V. cholera, S. marcesens, S. flexneri, T. pallidum, L. pneumophilia, B. burgdorferei; C. difficile, R. meliloti, A. tumefaciens; R. lupine; B. clarridgeiae, P. mirabilis, B. subtilus, L. moncytogenes, P. aeruginosa* and *E. coli*. In a particular embodiment, the flagellin is selected from the group consisting of *S. typhimurium* flagellin B (Genbank Accession number AF045151), a fragment of *S. typhimurium* flagellin B, *E. coli* FliC. (Genbank Accession number AB028476); fragment of *E. coli* FliC; *S. typhimurium* flagellin FliC (ATCC14028) and a fragment of *S. typhimurium* flagellin FliC. In a particular embodiment, said TLR5 agonist is a truncated flagellin or flagellin derivative as described in International Patent Application No. WO2009/156405 and U.S. Pat. Nos. 6,130,082, 6,585,980, and 7,192,725. In one aspect of this embodiment, said TLR5 agonist is selected from the group consisting of: $FliC_{\Delta 174-400}$; $FliC_{\Delta 161-405}$ and $FliC_{\Delta 138-405}$. In a further embodiment, said TLR5 agonist is a flagellin as described in International Patent Application No. WO2009/128950.

In one embodiment, a TLR agonist is used that is capable of causing a signaling response through TLR6. The TLR agonist capable of causing a signaling response through TLR6 can be a mycobacterial lipoprotein, di-acylated LP, and phenol-soluble modulin. Further TLR6 agonists are described in International Patent Application No. WO2003043572.

In one embodiment, a TLR agonist is used that is capable of causing a signaling response through TLR7. The TLR agonist capable of causing a signaling response through TLR7 can be a single stranded RNA (ssRNA), loxoribine, a guanosine analogue at positions N7 and C8, an imidazoquinoline compound, or derivative thereof, or an adenine derivative such as those disclosed in U.S. Pat. No. 6,329,381, U.S. Patent Application Publication No. 2010/0075995, or International Patent Application Publication No. WO 2010/018132. In one embodiment, the TLR agonist is imiquimod. Further TLR7 agonists are described in International Patent Application No. WO02085905.

In one embodiment, a TLR agonist is used that is capable of causing a signaling response through TLR8. The TLR agonist capable of causing a signaling response through TLR8 can be a single stranded RNA (ssRNA), an imidazoquinoline molecule with anti-viral activity, for example resiquimod (R848; InvivoGen); resiquimod is also capable of recognition by TLR7. Other TLR8 agonists which may be used include those described in International Patent Application No. WO2004071459.

In one embodiment, the composition of the invention comprises a TLR7/8 agonist such as an imidazoquinoline molecule, such as R848, in particular an imidazoquinoline covalently linked to a phosphor- or phosphonolipid group, and those compounds disclosed in U.S. Pat. No. 6,696,076, including, but not limited to, imidazoquinoline amines, imidazopyridine amines, 6,7-fused cycloalkylimidazopyridine amines, and 1,2-bridged imidazoquinoline amines. In one aspect of this embodiment, the TLR7/8 agonist is imiquimod or resiquimod (also known as R848). In a particular embodiment, compositions of the invention may comprise CRX642. See, e.g., International Patent Application Publication No. WO2010/048520.

In one embodiment, immunostimulatory oligonucleotides or any other Toll-like receptor (TLR) 9 agonist may also be used. The preferred oligonucleotides for use in immunogenic compositions of the present invention are CpG containing oligonucleotides, preferably containing two or more dinucleotide CpG motifs separated by at least three, more preferably at least six or more nucleotides. A CpG motif is a Cytosine nucleotide followed by a Guanine nucleotide. The CpG oligonucleotides are typically deoxynucleotides. In one embodiment, the internucleotide in the oligonucleotide is phosphorodithioate, or more preferably a phosphorothioate bond, although phosphodiester and other internucleotide bonds are also contemplated. Also included are oligonucleotides with mixed internucleotide linkages. See Krieg et al., 1995, Nature 374:546-549; Chu et al., 1997, J. Exp. Med. 186:1623-1631; Lipford et al., 1997, Eur. J. Immunol. 27:2340-2344; Roman et al., 1997, Nat. Med. 3:849-854; Davis et al., 1998, J. Immunol. 160:870-876; Lipford et al., 1998, Trends Microbiol. 6:496-500; and U.S. Pat. Nos. 6,207,646; 7,223,398; 7,250,403; or 7,566,703. Methods for producing phosphorothioate oligonucleotides or phosphorodithioate are described in U.S. Pat. Nos. 5,666,153, 5,278,302 and International Patent Application Publication No. WO95/26204.

In one embodiment of the invention, the TLR agonist is a TLR2/TLR6 agonist such as macrophage-activated lipopeptide-2 (MALP-2) or Fibroblast Stimulating Lipopeptide-1 (FSL-1). See, e.g., Becker et al., 2006, Vaccine 24:5269-76, and Rose et al., 2009, Virol J. 6:195, respectively.

In certain embodiments of the invention, the TLR agonists are natural or synthetic small molecules including, but not limited to, Complete Freund's Adjuvant (CFA), monophosphoryl lipid A (MPL A), Glucopyranosyl Lipid Adjuvant (GLA), macrophage-activated lipopeptide-2 (MALP-2), Pam2Cys, Fibroblast Stimulating Lipopeptide-1 (FSL-1), PolyI:C, poly A:U, alkyl Glucosaminide phosphate (AGP), imidazoquinoines, etc. See, e.g., Gnjatic et al., 2010, Cancer J. 16:382-391.

In certain embodiments of the invention, the invention formulation features LNP compositions formulated or complexed with TLR agonist compounds, and assembled within the following molar ratios:
Cationic Lipid (20-99.7 mole %)
Non-cationic lipid (0.1-65 mole %)
PEG-DMG (0.1-15 mole %)
TLR agonists (0.1-50 mole %).

In other embodiments of the invention, the TLR agonist is provided at a wt/wt % of agonist to total lipids in a range of 1% to 20% or 4% to 15%.

In certain embodiments of the invention, the one or more TLR agonist is physically encapsulated in the LNP before or after LNP preparation.

In certain embodiments of the invention, one or more TLR agonist is adsorbed, covalently coupled, ionically-interacted or formulated onto surfaces of the LNP. See, e.g., Li et al., 2002, Vaccine 20:148-157; Wilson et al., 2009, J. Gene Med. 11:14-25; Goldinger et al., 2012, Eur. J. Immunol. 42:3049-3061; Gursel et al., 2001, J. Immunol. 167: 3324-3328; and Chikh et al., 2009, Int. Immunol. 7:757-767.

Immunogenic compositions of the invention may comprise an immunostimulatory agent including natural or synthetic inflammatory cytokine receptor activators, for example, a saponin, such as Quil A and its derivatives, or squalene. Quil A is a saponin preparation isolated from the South American tree *Quilaja Saponaria* Molina and was first described as having adjuvant activity by Dalsgaard et al. in 1974 ("Saponin adjuvants", Archiv. fuer die gesamte Virusforschung, Vol. 44, Springer Verlag, Berlin, p 243-254). Purified fragments of Quil A have been isolated by HPLC which retain adjuvant activity without the toxicity associated with Quil A, for example QS7 and QS21 (also known as QA7 and QA21). QS-21 is a natural saponin derived from the bark of *Quillaja saponaria* Molina which induces CD8+ cytotoxic T cells (CTLs), Th1 cells and a predominant IgG2a antibody response. In certain embodiments, the immunostimulatory agent is an aluminum adjuvant, for example, aluminum phosphate or aluminum hydroxide. In another embodiment, an LNP composition of the instant invention further comprises a cryoprotectant. In another embodiment, the cryoprotectant is sucrose, trehalose, raffinose, stachyose, verbascose, mannitol, glucose, lactose, maltose, maltotrioseheptaose, dextran, hydroxyethyl starch, insulin, sorbitol, glycerol, arginine, histidine, lysine, proline, dimethylsulfoxide or any combination thereof. In another embodiment, the cryoprotectant is sucrose. In another embodiment, the cryoprotectant is trehalose. In another embodiment, the cryoprotectant is a combination of sucrose and trehalose.

Preparation of LNPs

LNPs can be formed, for example, by a rapid precipitation process which entails micro-mixing the lipid components dissolved in ethanol with an aqueous solution using a confined volume mixing apparatus such as a confined volume T-mixer, a multi-inlet vortex mixer (MIVM), or a microfluidics mixer device as described below. The lipid solution contains one or more cationic lipids, one or more noncationic lipids (e.g., DSPC), PEG-DMG, and optionally cholesterol, at specific molar ratios in ethanol. The aqueous solution consists of a sodium citrate or sodium acetate buffered salt solution with pH in the range of 2-6, preferably 3.5-5.5. The two solutions are heated to a temperature in the range of 25° C.-45° C., preferably 30° C.-40° C., and then mixed in a confined volume mixer thereby instantly forming the LNP. When a confined volume T-mixer is used, the T-mixer has an internal diameter (ID) range from 0.25 to 1.0 mm. The alcohol and aqueous solutions are delivered to the inlet of the T-mixer using programmable syringe pumps, and with a total flow rate from 10-600 mL/minute. The alcohol and aqueous solutions are combined in the confined-volume mixer with a ratio in the range of 1:1 to 1:3 vol:vol, but targeting 1:1.1 to 1:2.3. The combination of ethanol volume fraction, reagent solution flow rates and t-mixer tubing ID utilized at this mixing stage has the effect of controlling the particle size of the LNPs between 30 and 300 nm. The resulting LNP suspension is twice diluted into higher pH buffers in the range of 6-8 in a sequential, multi-stage in-line mixing process. For the first dilution, the LNP suspension is mixed with a buffered solution at a higher pH (pH 6-7.5) with a mixing ratio in the range of 1:1 to 1:3 vol:vol, but targeting 1:2 vol:vol. This buffered solution is at a temperature in the range of 15-40° C., targeting 30-40° C. The resulting LNP suspension is further mixed with a buffered solution at a higher pH, e.g., 6-8 and with a mixing ratio in the range of 1:1 to 1:3 vol:vol, but targeting 1:2 vol:vol. This later buffered solution is at a temperature in the range of 15-40° C., targeting 16-25° C. The mixed LNPs are held from 30 minutes to 2 hours prior to an anion exchange filtration step. The temperature during incubation period is in the range of 15-40° C., targeting 30-40° C. After incubation, the LNP suspension is filtered through a 0.8 µm filter containing an anion exchange separation step. This process uses tubing IDs ranging from 1 mm ID to 5 mm ID and a flow rate from 10 to 2000 mL/minute. The LNPs are concentrated and diafiltered via an ultrafiltration process where the alcohol is removed and the buffer is exchanged for the final buffer solution such as phosphate buffered saline or a buffer system suitable for cryopreservation (for example containing sucrose, trehalose or combinations thereof). The ultrafiltration process uses a tangential flow filtration format (TFF). This process uses a membrane nominal molecular weight cutoff range from 30-500 KD, targeting 100 KD. The membrane format can be hollow fiber or flat sheet cassette. The TFF processes with the proper molecular weight cutoff retains the LNP in the retentate and the filtrate or permeate contains the alcohol and final buffer wastes. The TFF process is a multiple step process with an initial concentration to a lipid concentration of 20-30 mg/mL. Following concentration, the LNP suspension is diafiltered against the final buffer (for example, phosphate buffered saline (PBS) with pH 7-8, 10 mM Tris, 140 mM NaCl with pH 7-8, or 10 mM Tris, 70 mM NaCl, 5 wt % sucrose, with pH 7-8) for 5-20 volumes to remove the alcohol and perform buffer exchange. The material is then concentrated an additional 1-3 fold via ultrafiltration. The final steps of the LNP manufacturing process are to sterile filter the concentrated LNP solution into a suitable container under aseptic conditions. Sterile filtration is accomplished by passing the LNP solution through a pre-filter (Acropak 500 PES 0.45/0.8 µm capsule) and a bioburden reduction filter (Acropak 500 PES 0.2/0.8 µm capsule). Following filtration, the vialed LNP product is stored under suitable storage conditions (2° C.-8° C., or −20° C. if frozen formulation).

For compositions containing TLR9 agonist, immumomodulatory oligonucleotides such as IMO2125 (see, e.g., Makowska et al., 2013, J Hepatol. 58:743-9) can be added to the aqueous solution to obtain the specified final wt/wt percentage. For compositions containing TLR4 agonist, TLR4 agonists such as GLA can be included with the other lipids in ethanol to obtain the specified final wt/wt percentage.

In some embodiments, the LNPs of the compositions provided herein have a mean geometric diameter that is less than 500 nm. In some embodiments, the LNPs have mean geometric diameter that is greater than 50 nm but less than 500 nm. In some embodiments, the mean geometric diameter of a population of LNPs is about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, the mean geometric diameter is between 100-400 nm, 100-300 nm, 100-250 nm, or 100-200 nm. In some embodiments, the mean geometric diameter is between 60-400 nm, 60-350 nm, 60-300 nm, 60-250 nm, or 60-200 nm. In some embodiments, the mean geometric diameter is between 75-250 nm. In some embodiments, 30%, 40%, 50%, 60%, 70%, 80%, 90%, or more of the LNPs of a population of LNPs have a diameter that is less than 500 nM. In some embodiments, 10%, 20%, 30%, 40%, 50%, 60%, 70%, 80%, 90%, or more of the LNPs of a population of LNPs have a diameter that is greater than 50 nm but less than 500 nm. In some embodiments, 10%, 20%, 30%, 40%, 50%, 60%, 70%, 80%, 90%, or more of the LNPs of a population of LNPs have a diameter of about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, 10%, 20%, 30%, 40%, 50%, 60%, 70%, 80%, 90%, or more of the LNPs of a population of LNPs have a diameter that is between 100-400 nm, 100-300 nm, 100-250 nm, or 100-200 nm. In some embodiments, 10%, 20%, 30%, 40%, 50%, 60%, 70%, 80%, 90%, or more of the LNPs of a population of LNPs have a diameter that is between 60-400 nm, 60-350 nm, 60-300 nm, 60-250 nm, or 60-200 nm.

In a particular embodiment, the size of the LNPs ranges between about 1 and 1000 nm, preferably between about 10 and 500 nm, and more preferably between about 100 to 200 nm.

Antigens

The disclosed compositions and methods are applicable to a wide variety of antigens. In certain embodiments, the antigen is a protein (including recombinant proteins), polypeptide, or peptide (including synthetic peptides). In certain embodiments, the antigen is a lipid or a carbohydrate (polysaccharide). In certain embodiments, the antigen is a protein extract, cell (including tumor cell), or tissue. The compositions provided herein can contain one or more antigens (e.g., at least two, three, four, five, or six antigens).

In specific embodiments, antigens can be selected from the group consisting of the following: (a) polypeptides suitable to induce an immune response against cancer cells; (b) polypeptides suitable to induce an immune response against infectious diseases; (c) polypeptides suitable to induce an immune response against allergens; and (d) polypeptides suitable to induce an immune response in farm animals or pets.

In certain embodiments, the compositions of the invention can be used in combination with an immunoregulatory therapy to target either activating receptors or inhibitory receptors. See, e.g., Mellman et al., 2013, Nature 480:480-489. The immunoregulatory therapy can be, for example, a T cell engaging agent selected from agonistic antibodies which bind to human OX40, to GITR, to CD27, or to 4-IBB, and T-cell bispecific antibodies (e.g. T cell-engaging BiTE™ antibodies CD3-CD19, CD3-EpCam, CD3-EGFR), IL-2 (Proleukin), Interferon (IFN) alpha, antagonizing antibodies which bind to human CTLA-4 (e.g. ipilimumab), to PD-1, to PD-L1, to TIM-3, to BTLA, to VISTA, to LAG-3, or to CD25.

Exemplary antigens include those from a pathogen (e.g. virus, bacterium, parasite, fungus) and tumors (especially tumor-associated antigens or "tumor markers"). Other exemplary antigens include autoantigens.

In some embodiments, the antigen or antigenic determinant is one that is useful for the prevention of infectious disease. Such treatment will be useful to treat a wide variety of infectious diseases affecting a wide range of hosts, preferably human, but including cow, sheep, pig, dog, cat, and other mammalian species and non-mammalian species. Thus, antigens or antigenic determinants selected for the compositions will be well known to those in the medical art.

Examples of antigens or antigenic determinants include the following: the RSV F or G antigens, Chlamydia antigens such as the Major outer membrane protein (mOMP), the Dengue type 1 to 4 envelope proteins, the HIV antigens gp140 and gp160; the influenza antigens hemagglutinin, M2 protein, and neuraminidase; hepatitis B surface antigen or core; and circumsporozoite protein of malaria, or fragments thereof.

Appropriate antigens for use with this LNP technology may be derived from, but not limited to, pathogenic bacterial, fungal, or viral organisms, *Streptococcus* species, *Candida* species, *Brucella* species, *Salmonella* species, *Shigella* species, *Pseudomonas* species, *Bordetella* species, *Clostridium* species, Norwalk virus, *Bacillus anthracis, Mycobacterium tuberculosis*, human immunodeficiency virus (HIV), *Chlamydia* species, human Papillomaviruses, Influenza virus, *Paramyxovirus* species, Herpes virus, Cytomegalovirus, Varicella-Zoster virus, Epstein-Barr virus, Hepatitis viruses, *Plasmodium* species, *Trichomonas* species, Ebola, sexually transmitted disease agents, viral encephalitis agents, protozoan disease agents, fungal disease agents, cancer cells, or mixtures thereof. Other appropriate molecules incorporated in the nanoparticle vaccines may include self-antigens, adhesins, or surface exposed cell signaling receptors or ligands. A variety of diseases and disorders may be treated by such nanoparticle vaccine constructs or assemblies, including: inflammatory diseases, infectious diseases, cancer, genetic disorders, organ transplant rejection, autoimmune diseases and immunological disorders.

Examples of infectious disease include, but are not limited to, viral infectious diseases, such as AIDS, Respiratory Syncytial Virus (RSV), Chickenpox (Varicella), Common cold, Cytomegalovirus Infection, Colorado tick fever, Dengue fever, Ebola hemorrhagic fever, Hand, foot and mouth disease, Hepatitis, Herpes simplex, Herpes zoster, HPV, Influenza (Flu), Lassa fever, Measles, Marburg hemorrhagic fever, Infectious mononucleosis, Mumps, Norovirus, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease and Yellow fever; bacterial infectious diseases, such as Anthrax, Bacterial Meningitis, Botulism, Brucellosis, Campylobacteriosis, Cat Scratch Disease, Cholera, Diphtheria, Epidemic Typhus, Gonorrhea, Impetigo, Legionellosis, Leprosy (Hansen's Disease), Leptospirosis, Listeriosis, Lyme disease, Melioidosis, Rheumatic Fever, MRSA infection, Nocardiosis, Pertussis (Whooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus and Urinary Tract Infections; parasitic infectious diseases, such as African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kalaazar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trichomoniasis and Trypanosomiasis; fungal infectious disease, such as Aspergillosis, Blastomycosis, Candidiasis, Coccidioidomycosis, Cryptococcosis, Histoplasmosis, Tinea pedis (Athlete's Foot) and Tinea cruris; prion infectious diseases, such as Alpers' disease, Fatal Familial Insomnia, Gerstmann-Straussler-Scheinker syndrome, Kuru and Variant Creutzfeldt-Jakob disease.

Examples of cancers include, but are not limited to breast cancer; biliary tract cancer; bladder cancer; brain cancer including glioblastomas and meduUoblastomas; cervical cancer; choriocarcinoma; colon cancer; endometrial cancer; esophageal cancer; gastric cancer; hematological neoplasms including acute lymphocytic and myelogenous leukemia, e.g., B Cell CLL; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor.

Any antigen associated with any of the diseases or conditions provided herein can be used in the compositions and methods described herein. These include antigens associated with cancer, infections or infectious disease or degenerative or non-autoimmune disease. Antigens associated with HIV, malaria, leishmaniasis, a human filovirus infection, a togavirus infection, a alphavirus infection, an arenavirus infection, a bunyavirus infection, a flavivirus infection, a human papillomavirus infection, a human influenza A virus infection, a hepatitis B infection or a hepatitis C infection are also included.

Examples of cancer antigens include HER 2 (pi 85), CD20, CD33, GD3 ganglioside, GD2 ganglioside, carcinoembryonic antigen (CEA), CD22, milk mucin core protein, TAG-72, Lewis A antigen, ovarian associated antigens such as OV-TL3 and MOvl8, high Mr melanoma antigens recognized by antibody 9.2.27, HMFG-2, SM-3, B72.3, PR5C5, PR4D2, and the like. Further examples include MAGE, MART-1/Melan-A, gp100, Dipeptidyl peptidase IV (DPPIV), adenosine deaminase-binding protein (ADAbp), FAP, cyclophilin b, Colorectal associated antigen (CRC)—C017-1A/GA733, Carcinoembryonic Antigen (CEA) and its immunogenic epitopes CAP-1 and CAP-2, etv6, aml1, prostatic acid phosphatase (PAP), Prostate Specific Antigen (PSA) and its immunogenic epitopes PSA-1, PSA-2, and PSA-3, pro state-specific membrane antigen (PSMA), T-cell receptor/CD3-zeta chain, MAGE-family of tumor antigens (e.g., MAGE-I or MAGE-II families) (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, a-fetoprotein, E-cadherin, a-catenin, β-catenin and γ-catenin, p120ctn, gp100Pmell 17, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, PIA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20 and c-erbB-2.

In another embodiment, antigens associated with infection or infectious disease are associated with any of the infectious agents provided herein. In one embodiment, the infectious agent is a virus of the Adenoviridae, Picornaviridae, Herpesviridae, Hepadnaviridae, Flaviviridae, Retroviridae, Orthomyxoviridae, Paramyxoviridae, Papillomaviridae, Rhabdoviridae, Togaviridae or Paroviridae family. In still another embodiment, the infectious agent is adenovirus, coxsackievirus, hepatitis A virus, poliovirus, Rhinovirus, Herpes simplex virus, Varicella-zoster virus, Epstein-barr virus, Human cytomegalovirus, Human herpesvirus, Hepatitis B virus, Hepatitis C virus, yellow fever virus, dengue virus, West Nile virus, HIV, Influenza virus, Measles virus, Mumps virus, Parainfluenza virus, Respiratory syncytial virus, Human metapneumovirus, Human papillomavirus, Rabies virus, Rubella virus, Human bocarivus or Parvovirus B19. In yet another embodiment, the infectious agent is a bacteria of the *Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema Vibrio* or *Yersinia* genus. In a further embodiment, the infectious agent is *Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitides, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae* or *Yersinia pestis*. In another embodiment, the infectious agent is a fungus of the *Candida, Aspergillus, Cryptococcus, Histoplasma, Pneumocystis* or *Stachybotrys* genus. In still another embodiment, the infectious agent is *C. albicans, Aspergillus fumigatus, Aspergillus flavus, Cryptococcus neoformans, Cryptococcus laurentii, Cryptococcus albidus, Cryptococcus gattii, Histoplasma capsulatum, Pneumocystis jirovecii* or *Stachybotrys chartarum*.

In yet another embodiment, the antigen associated with infection or infectious disease is one that comprises VI, VII, E1A, E3-19K, 52K, VP1, surface antigen, 3A protein, capsid protein, nucleocapsid, surface projection, transmembrane proteins, UL6, UL18, UL35, UL38, UL19, early antigen, capsid antigen, Pp65, gB, p52, latent nuclear antigen-1, NS3, envelope protein, envelope protein E2 domain, gp120, p24, lipopeptides Gag (17-35), Gag (253-284), Nef (66-97), Nef (116-145), Pol (325-355), neuraminidase, nucleocapsid protein, matrix protein, phosphoprotein, fusion protein, hemagglutinin, hemagglutinin-neuraminidase, glycoprotein, E6, E7, envelope lipoprotein or non-structural protein (NS). In another embodiment, the antigen comprises pertussis toxin (PT), filamentous hemagglutinin (FHA), pertactin (PRN), fimbriae (FIM 2/3), VlsE; DbpA, OspA, Hia, PrpA, MltA, L7/L12, D15, 0187, VirJ, Mdh, AfuA, L7/L12, out membrane protein, LPS, antigen type A, antigen type B, antigen type C, antigen type D, antigen type E, FliC, FliD, Cwp84, alpha-toxin, theta-toxin, fructose 1,6-biphosphate-aldolase (FBA), glyceraldehydes-3-phosphate dehydrogenase (GPD), pyruvate:ferredoxin oxidoreductase (PFOR), elongation factor-G (EF-G), hypothetical protein (HP), T toxin, Toxoid antigen, capsular polysaccharide, Protein D, Mip, nucleoprotein (NP), RD1, PE35, PPE68, EsxA, EsxB, RD9, EsxV, Hsp70, lipopolysaccharide, surface antigen, Sp1, Sp2, Sp3, Glycerophosphodiester Phosphodiesterase, outer membrane protein, chaperone-usher protein, capsular protein (Fl) or V protein. In yet another embodiment, the antigen is one that comprises capsular glycoprotein, Yps3P, Hsp60, Major surface protein, MsgC1, MsgC3, MsgC8, MsgC9 or SchS34.

In certain embodiments of the invention, one or more antigens are physically encapsulated in the LNP during or after LNP preparation. Antigens physically encapsulated in the LNP can be prepared via confined-volume ethanol desolvation method as described, or via alternative techniques known in the art, including, but not limited to thin-film hydration, emulsion diffusion, or homogenization.

In certain embodiments of the invention, one or more of the antigens is adsorbed, covalently coupled, ionically-interacted, or formulated onto surfaces of the LNP adjuvant.

In an alternative embodiment, the LNP adjuvant may be co-administered with one or more antigens and/or one or more agonists.

The compositions and methods described herein can be used to induce, enhance, suppress, modulate, direct, or redirect an immune response. The compositions and methods described herein can be used in the diagnosis, prophylaxis and/or treatment of conditions such as cancers, infectious diseases, non-autoimmune diseases, HIV, malaria, hepatitis B or any of the other disorders and/or conditions provided herein.

The compositions of the invention can be administered to cells by a variety of methods known to those of skill in the art. In one embodiment, delivery systems of the invention include, for example, aqueous and nonaqueous gels, multiple emulsions, microemulsions, aqueous and nonaqueous solutions, aerosols, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a transdermal enhancer.

In one embodiment, delivery systems of the invention include patches, suppositories, and gels, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

In one embodiment, the invention features a composition comprising one or more formulated antigens in an acceptable carrier, such as a stabilizer, buffer, and the like. The compositions of the invention can be administered and introduced to a subject by any standard means, with or without stabilizers, buffers, and the like, to form a composition. The compositions of the present invention can also be formulated and used as gels, sprays, oils and other suitable compositions for topical, dermal, or transdermal administration as is known in the art.

An immunological composition or formulation refers to a composition or formulation in a form suitable for administration, e.g., systemic or local administration, into a cell or subject, including for example a human. Suitable forms, in part, depend upon the use or the route of entry, for example oral, transdermal, or by injection. Such forms should not prevent the composition or formulation from reaching a target cell. For example, pharmacological compositions injected into the blood stream should be soluble. Other factors are known in the art, and include considerations such as toxicity and forms that prevent the composition or formulation from exerting its effect.

In one embodiment, compositions of the invention are administered to a subject by systemic administration in a pharmaceutically acceptable composition or formulation. By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular.

By "pharmaceutically acceptable formulation" or "pharmaceutically acceptable composition" is meant, a composition or formulation suitable for administration in the physical location most suitable for their desired activity. Non-limiting examples of agents suitable for formulation with the formulated molecular compositions of the instant invention include: P-glycoprotein inhibitors (such as Pluronic P85); biodegradable polymers, such as poly (DL-lactide-coglycolide) microspheres for sustained release delivery (Emerich et al, 1999, *Cell Transplant*, 8, 47-58); and loaded nanoparticles, such as those made of polybutylcyanoacrylate.

The present invention also includes compositions prepared for storage or administration that include a pharmaceutically effective amount of the desired lipid nanoparticles in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the formulated composition.

The formulated compositions of the invention can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a formulated composition of the invention and a pharmaceutically acceptable carrier. One or more formulated molecular compositions of the invention can be present in association with one or more non-toxic pharmaceutically acceptable carriers and/or diluents and/or adjuvants, and if desired other active ingredients. The pharmaceutical compositions containing formulated compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the lipid nanoparticles in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the lipid nanoparticles are mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the lipid nanoparticles in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the lipid nanoparticles in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the lipid nanoparticles in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono-or diglycerides. In addition, fatty acids such as oleic acid find use in the preparation of injectables.

The compositions of the invention can also be administered in the form of suppositories, e.g., for rectal administration of the drug. These compositions can be prepared by mixing the lipid nanoparticles with a suitable non-irritating excipient that is solid at ordinary temperatures but liquid at the rectal temperature and will therefore melt in the rectum to release the drug. Such materials include cocoa butter and polyethylene glycols.

Formulated compositions of the invention can be administered parenterally in a sterile medium. The lipid nanoparticles, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of lipid nanoparticles that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the antigen employed, the age, body weight, general health, sex, diet, time of administration, route of administration, and rate of excretion, and the severity of the particular disease undergoing prophylaxis/therapy.

For administration to non-human animals, the composition can also be added to water. It can be convenient to formulate the animal feed and drinking water compositions so that the animal takes in a therapeutically appropriate quantity of the composition along with its diet. It can also be convenient to present the composition as a premix for addition to the feed or drinking water.

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

EXAMPLES

Example 1: Preparation of Basic LNP Compositions

The lipid nanoparticle (LNP) compositions of Table 3, with the specified molar concentrations of cationic lipid 9 from International Patent Application Publication No. WO2011/022460 (compound 1-9) or cationic lipid 32 or 33 from International Patent Application Publication No. WO2012/040184 (compound 2-32 or compound 2-33, respectively), cholesterol, PEG-DMG, and optionally DSPC, were prepared as described in detail below.

TABLE 3

Lipid Composition of Basic LNP Compositions

| LNP Identifier | Lipid Components | Lipid Composition (molar ratio) |
| --- | --- | --- |
| 1 | Cationic Lipid/Cholesterol/DSPC/PEG-DMG | 40/48/10/2 |
| 2 | Cationic Lipid/Cholesterol/DSPC/PEG-DMG | 58/30/10/2 |
| 3 | Cationic Lipid/Cholesterol/DSPC/PEG-DMG | 59/30/10/1 |
| 4 | Cationic Lipid/Cholesterol/DSPC/PEG-DMG | 42/41/15/2 |
| 5 | Cationic Lipid/Cholesterol/DSPC/PEG-DMG | 38/41/19/2 |
| 6 | Cationic Lipid/Cholesterol/DSPC/PEG-DMG | 33/41/24/2 |
| 7 | Cationic Lipid/Cholesterol/DSPC/PEG-DMG | 43/41/15/1 |
| 8 | Cationic Lipid/Cholesterol/DSPC/PEG-DMG | 39/41/19/1 |
| 9 | Cationic Lipid/Cholesterol/DSPC/PEG-DMG | 34/41/24/1 |
| 10 | Cationic Lipid/Cholesterol/PEG-DMG | 51/45/4 |
| 11 | Cationic Lipid/Cholesterol/PEG-DMG | 51/43.5/5.5 |
| 12 | Cationic Lipid/Cholesterol/PEG-DMG | 60/38/2 |
| 13 | Cationic Lipid/Cholesterol/PEG-DMG | 68/29/4 |

The LNPs were formed by a rapid precipitation process which entailed micro-mixing lipids dissolved in ethanol with an aqueous solution using a confined volume mixing apparatus (T-mixer with inner diameter (ID) of 0.5 mm). The lipid solution contained cationic lipid, cholesterol, PEG-DMG, and phospholipid (DSPC) at the specified molar ratios in ethanol. The aqueous solution consisted of a sodium citrate buffered salt solution [20 mM] with pH in the range of 5-5.5. The two solutions were heated to a temperature in the range of 35° C.-40° C., and then mixed in a confined volume mixer (T-mixer with ID of 0.5 mm) instantly forming the LNP. The alcohol and aqueous solutions were delivered to the inlet of the T-mixer using programmable syringe pumps, and with a total flow rate from 100-150 mL/minute. The alcohol and aqueous solutions were combined in the confined-volume mixer with a ratio in the range of 11:1.5 to 2.1:3.8 to produce 40-55 vol:vol % alcohol in the mixed solution. The combination of ethanol volume fraction, reagent solution flow rates and t-mixer tubing ID utilized at this mixing stage had the effect of controlling the particle size of the LNPs between 30 and 300 nm. The resulting LNP suspension was twice diluted into higher pH buffers [pH range 6-8] in a sequential, multi-stage in-line mixing process. For the first dilution, the LNP suspension was mixed with a 20 mM sodium citrate, 300 mM sodium chloride buffered solution with pH 6 with a mixing ratio of 1:1 vol:vol. This buffered solution was at a temperature in the range of 35-40° C. The resulting LNP suspension was further mixed with a buffered solution (phosphate buffered saline (PBS), pH of 7.5) and with a mixing ratio of 1:1 vol:vol. This later buffered solution was at a temperature in the range 16-25° C. The mixed LNPs were held from 30 minutes prior to an anion exchange filtration step. The temperature during incubation period was in the range of 30-40° C. After incubation, the LNPs were concentrated and diafiltered via an ultrafiltration process where the alcohol was removed and the buffer was exchanged for the final buffer solution. The ultrafiltration process used a tangential flow filtration format (TFF). This process used a polyethersulfone (PES) membrane with a nominal molecular weight cutoff of 100 KD. The membrane format was hollow fiber or flat sheet cassette. Ultrafiltration with a 100 kDa PES membrane was first used to concentrate the LNP solution 8-fold by volume, targeting a total lipids concentration of 20-30 mg/mL. Ethanol removal was effected by subsequent diafiltration using 10 mM Tris, 140 mM sodium chloride, pH 7-7.5 (5-10 diavolumes). A final buffer exchange into a buffer solution comprising 10 mM Tris, 70 mM NaCl and 5 wt % sucrose was performed. The LNP solution was then sterile filtered into sterile vials under aseptic conditions via Pall 0.45 µm PES, and a Pall 0.2 PES µm syringe filters. The LNP solution was stored under refrigeration (2-8° C.) or as a frozen image (−20° C.).

Analytical Procedure

Particle Size and Polydispersity

LNPs were diluted to a final volume of 3 ml with 1× phosphate buffered saline (PBS). The particle size and polydispersity of the samples was measured by a dynamic light scattering method using ZetaPALS instrument (Brookhaven Instruments Corporation, Holtsville, N.Y.). The scattered intensity was measured with He—Ne laser at 25° C. with a scattering angle of 90°.

Zeta Potential Measurement

LNPs were diluted to a final volume of 2 ml with 1 mM Tris buffer (pH 7.4). Electrophoretic mobility of samples was determined using ZetaPALS instrument (Brookhaven Instruments Corporation, Holtsville, N.Y.) with a disposable Zeta cell DTS 1060C (Malvern Instruments Ltd, Worcestershire, UK) and He—Ne laser as a light source. The Smoluchowski limit (Z. Phys. Chem., 93 (1918), p. 129) was assumed in the calculation of zeta potentials.

Lipids Analysis

Individual lipid concentrations were determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc, Chelmsford, Mass.). Individual lipids in RDVs were analyzed using an Agilent Zorbax SB-C18 (50×4.6 mm, 1.8 µm particle size) column with CAD at 60° C. The mobile phase was composed of A: 0.1% trifluoroacetic acid (TFA) in $H_2O$ and B: 0.1% TFA in isopropyl alcohol (IPA). The gradient changed from 60% mobile phase A and 40% mobile phase B from time 0 to 40% mobile phase A and 60% mobile phase B at 1.00 min; 40% mobile phase A and 60% mobile phase B from 1.00 to 5.00 min; 40% mobile phase A and 60% mobile phase B from 5.00 min to 25% mobile phase A and 75% mobile phase B at 10.00 min; 25% mobile phase A and 75% mobile phase B from 10.00 min to 5% mobile phase A and 95% mobile phase B at 15.00 min; and 5% mobile phase A and 95% mobile phase B from 15.00 to 60% mobile phase A and 40% mobile phase B at 20.00 min with a flow rate of 1 ml/minute. The individual lipid concentration was determined by comparing to the standard curve with all the lipid components in the RDVs with a quadratic curve fit. The molar percentage of each lipid was calculated based on its molecular weight.

Analytic analysis confirmed the correct molar ratios.

Example 2: Preparation of LNP Formulations Containing TLR Agonists

Lipid nanoparticles (LNP) formulations encapsulating immunostimulatory oligonucleotides (also referred to as immune modulatory oligonucleotides (IMO)) or Glucopyranosyl Lipid A (GLA), were prepared as described in Example 1 with the following modifications. The LNPs were formed by micro-mixing lipids dissolved in ethanol with an aqueous solution containing the IMO2125 (TLR9 agonist) or GLA (TLR4 agonist), using a confined volume mixing apparatus. The aqueous solution consisted of a sodium citrate solution [20 mM sodium citrate] with pH in the range of 5-5.5. For compositions containing TLR9 agonist, IMO2125 was added to the aqueous solution to obtain the specified final wt/wt percentage. For compositions containing TLR4 agonist, GLA was included with the other lipids in ethanol to obtain the specified final wt/wt percentage.

TABLE 4

Compositions of LNP Formulations containing TLR agonists

| LNP Identifier | Lipid Components | Lipid Composition (mole/mole) | TLR Agonist Component | Agonist Composition (wt/wt % agonist/total lipids) |
|---|---|---|---|---|
| 14 | 1-9/Cholesterol/DSPC/PEG-DMG | 58/30/10/2 | not applicable | 0/100 |
| 15 | 1-9/Cholesterol/DSPC/PEG-DMG | 58/30/10/2 | TLR9 agonist IMO2125 | 6.5/93.5 |
| 16 | 2-32/Cholesterol/DSPC/PEG-DMG | 58/30/10/2 | not applicable | 0/100 |
| 17 | 2-32/Cholesterol/DSPC/PEG-DMG | 58/30/10/2 | TLR9 agonist IMO2125 | 9/91 |
| 18 | 1-9/Cholesterol/DSPC/PEG-DMG | 59/30/10/1 | not applicable | 0/100 |
| 19 | 2-32/Cholesterol/DSPC/PEG-DMG | 59/30/10/1 | not applicable | 0/100 |
| 20 | 2-32/Cholesterol/DSPC/PEG-DMG | 58/30/10/2 | TLR 4 agonist Glucopyranosyl Lipid A (GLA) | 4.5/95.5 |
| 21 | 2-32/Cholesterol/DSPC/PEG-DMG | 58/30/10/2 | TLR 4 agonist Glucopyranosyl Lipid A (GLA) | 9.2/90.8 |
| 23 | 2-32/Cholesterol/DSPC/PEG-DMG | 58/30/10/2 | TLR 4 agonist Glucopyranosyl Lipid A (GLA) | 13.2/86.8 |
| 24 | 2-33/Cholesterol/DSPC/PEG-DMG | 58/30/10/2 | not applicable | 0/100 |

Analytical Procedure

IMO Concentration

The IMO concentrations were determined by Strong Anion-Exchange High-Performance Liquid Chromatography (SAX-HPLC) using Waters 2695 Alliance system (Water Corporation, Milford Mass.) with a 2996 PDA detector. The LNPs were treated with 0.5% Triton X-100 to free total IMO and analyzed by SAX separation using a Dionex BioLC DNAPac PA 200 (4×250 mm) column with UV detection at 254 nm. Mobile phase was composed of A: 25 mM $NaClO_4$, 10 mM Tris, 20% EtOH, pH 7.0 and B: 250 mM $NaClO_4$, 10 mM Tris, 20% EtOH, pH 7.0 with a linear gradient from 0-15 min and a flow rate of 1 ml/minute. The IMO amount was determined by comparing to the IMO standard curve.

Glucopyranosyl Lipid A (GLA) Analysis

Reverse phase chromatography was used to characterize and quantify GLA in lipid nanoparticles, using an Acquity Ultra Performance Liquid Chromatography (UPLC) (Waters, Milford, Mass.). Samples were injected onto a Luna C18, 5 μm, 150×4.60 mm column (Phenomenex, Torrance, Calif.) at a temperature of 30° C. with a mobile phase flow rate of 1.0 mL/min and a 30 minute gradient that consisted of 0.2% trifluoroacetic acid (TFA) in 95:5 methanol:water and 0.2% TFA in 100% isopropanol. The chromatogram signal was detected using a charged aerosol detector (CAD) (Dionex, Sunnyville, Calif.). A five-point quadratic standard GLA curve was used to quantify the concentration of GLA in each sample. Lipid components of the lipid nanoparticle were quantified using a different reverse phase method in a separate experiment. The samples were injected onto a RRHD SB-C18, 1.8 μm, 2.1×50 mm reverse phase column (Agilent Technologies, Santa Clara, Calif.) at a temperature of 80° C. A flow rate of 1.2 mL/min was used with a 3.6 minute gradient that consisted of 0.1% TFA in water and 0.1% TFA in methanol. This signal was also detected using a CAD. The lipid components were then quantified using a five-point quadratic standard curve.

Encapsulation Rate

Fluorescence reagent SYBR Gold was employed for IMO quantitation to monitor the encapsulation of oligonucleotide in RDVs. RDVs with or without Triton X-100 were used to determine the free IMO and total IMO amount. The assay was performed using a SpectraMax M5e microplate spectrophotometer from Molecular Devices (Sunnyvale, Calif.). Samples were excited at 485 nm and fluorescence emission was measured at 530 nm. The IMO amount is determined by comparing to an IMO standard curve. Encapsulation rate= (1-free IMO/total IMO)×100%.

Example 3: Particle Size Optimization

LNPs were prepared as described in Example 1. The alcohol and aqueous solutions were combined in the confined-volume mixer with a ratio in the range of 11:1.5 to 2.1:3.8 to produce 40-55 vol:vol % alcohol in the mixed solution. The combination of ethanol volume fraction, reagent solution flow rates and t-mixer tubing ID utilized at this mixing stage had the effect of controlling the particle size of the LNPs between 30 and 300 nm.

TABLE 5

Particle Size Optimization of LNP Formulations

| LNP Identifier | Lipid Components | Lipid Composition (mole/mole) | TLR Agonist Component | LNP Diameter (nm) | Particle Size Distribution Index (PDI) |
|---|---|---|---|---|---|
| 25 | 2-32/Cholesterol/DSPC/PEG-DMG | 58/30/10/2 | not applicable | 60 | 0.23 |

TABLE 5-continued

Particle Size Optimization of LNP Formulations

| LNP Identifier | Lipid Components | Lipid Composition (mole/mole) | TLR Agonist Component | LNP Diameter (nm) | Particle Size Distribution Index (PDI) |
|---|---|---|---|---|---|
| 16 | 2-32/Cholesterol/DSPC/PEG-DMG | 58/30/10/2 | not applicable | 89 | 0.12 |
| 26 | 2-32/Cholesterol/DSPC/PEG-DMG | 58/30/10/2 | not applicable | 156 | 0.18 |
| 27 | 2-32/Cholesterol/DSPC/PEG-DMG | 58/30/10/2 | not applicable | 239 | 0.14 |

Example 4: Testing Lipid Nanoparticles Contain TLR9 Agonist IMO2125 as Adjuvants with a Recombinant Subunit Dengue 2 Envelope Vaccine in Balb/c Mice The objective of this mouse immunogenicity study was to evaluate the ability of Lipid NanoParticles (LNPs) formulated to contain TLR9 agonist IMO2125, to adjuvant a recombinant Dengue 2 envelope subunit protein. See Clements et al., 2010, Vaccine 28:2705. The Dengue 2 envelope protein is truncated at the C-terminal end to remove the transmembrane domain and is referred to as DEN2-80E since it represents 80% of the wild type amino acid sequence. For the study a dose titration of the LNP 15 and LNP 17 formulations, were evaluated. The dose was based on the combined dose of LNP components and IMO. For comparison a dose titration of IMO alone was also evaluated at the same dose levels of IMO present in the LNP/IMO formulations. The study also included four additional groups, 1) a no adjuvant control group, 2) a group receiving ISCOMATRIX™ adjuvant (IMX); 3) a group receiving LNP 14 (similar to LNP15 without IMO) and 4) a group receiving LNP 16 (similar to LNP 17 without IMO). The dose of LNP 14 and LNP 16 was based of the combined dose of the LNP components.

The candidate vaccine formulations described above were administered as outlined in Table 6. The DEN2-80E and adjuvants were field mixed to produce the final vaccine formulations just prior to administration. Each vaccine or control formulation was administered to healthy 8-9 week old female Balb/c mice (n=10/group) in 100 µl total volume by intramuscular (IM) inoculation (50 µl per quadricep). Three doses of vaccine were administered at 2 week intervals.

TABLE 6

Schedule and Formulations Used in Balb/c Immunogenicity Study

| Group | Mice per group | Antigen dose | Adjuvant* dose | Route | Schedule (Weeks) |
|---|---|---|---|---|---|
| 1 | 10 | 1 µg DEN2-80E | PBS | IM | 0, 2, 4 |
| 2 | 10 | 1 µg DEN2-80E | IMX (1.43 ISCO units) | IM | 0, 2, 4 |
| 3 | 10 | 1 µg DEN2-80E | IMO2125 (0.5 µg) | IM | 0, 2, 4 |
| 4 | 10 | 1 µg DEN2-80E | IMO2125 (1.0 µg) | IM | 0, 2, 4 |
| 5 | 10 | 1 µg DEN2-80E | IMO2125 (5.0 µg) | IM | 0, 2, 4 |
| 6 | 10 | 1 µg DEN2-80E | IMO2125 (10.0 µg) | IM | 0, 2, 4 |
| 7 | 10 | 1 µg DEN2-80E | LNP 17 (6.0 µg) | IM | 0, 2, 4 |
| 8 | 10 | 1 µg DEN2-80E | LNP 17 (12.3 µg) | IM | 0, 2, 4 |
| 9 | 10 | 1 µg DEN2-80E | LNP 17 (61.3 µg) | IM | 0, 2, 4 |
| 10 | 10 | 1 µg DEN2-80E | LNP 17 (122.3 µg) | IM | 0, 2, 4 |
| 11 | 10 | 1 µg DEN2-80E | LNP 15 (8.2 µg) | IM | 0, 2, 4 |
| 12 | 10 | 1 µg DEN2-80E | LNP 15 (16.7 µg) | IM | 0, 2, 4 |
| 13 | 10 | 1 µg DEN2-80E | LNP 15 (83.1 µg) | IM | 0, 2, 4 |
| 14 | 10 | 1 µg DEN2-80E | LNP 15 (166.5 µg) | IM | 0, 2, 4 |
| 15 | 10 | 1 µg DEN2-80E | LNP 16 (145.2 µg) | IM | 0, 2, 4 |
| 16 | 10 | 1 µg DEN2-80E | LNP 14 (145.1 µg) | IM | 0, 2, 4 |

Dengue virus 2 (DENV2) neutralizing titers were determined 2 weeks after the final vaccine dose using a LiCor based microneutralization assay. The LiCor assay is based on detection of Dengue envelope protein antigen expressed in cells, using near infrared dye-labeled immune reagents similar to the format described in Wang et al., 2011, Vaccine 29:9075-9080. Briefly, Vero cells were seeded in 96-well tissue culture plates. In a separate plate, serum samples were serially diluted 2-fold in duplicate for 8 dilutions beginning at 1:10. Serum was incubated with an equal volume of DEN2 virus diluted to 50 pfu/well and the mixture incubated at 37° C.+5% $CO_2$ for 1 hour. Following neutralization, the entire mixture was added onto the plated Vero cells and incubated for 4 days at 37° C.+5% $CO_2$. At the end of 4 days the culture media was removed and the cells were fixed with 3.7% formaldehyde. The plates were then washed and stained with 50 µl of anti-dengue mAb 4G2 (Henchal et al., 1982, The American Journal of Tropical Medicine and Hygiene 31(4):830-836) followed by a biotinylated horse anti-mouse IgG at 7.5 µg/ml. Finally a cocktail of IRDye® 800CW Streptavidin (1:1000) and DRAQS (1:10,000) was added and incubated for 1 hour in the dark. Plates were washed 3 times between antibody exchanges using 0.1% Tween-20/PBS. Incubation steps were performed for 1 hour at room temperature. Plates were air-dried and scanned with an infrared Odyssey® Sa imaging system (Li-Cor Biosciences). Serum end-point neutralization titers were defined as the reciprocal of the highest serum dilution that reduces the 800 nm/700 nm fluorescence integrated intensity ratio greater than 50% when compared to virus control included on each assay plate.

Neutralization titers measured in individual mice are summarized in FIG. 1. The data demonstrate a dose dependent response for both LNP/IMO formulations with the responses for the LNP 17 formulations trending slightly better than the LNP 15 formulations. Responses at the higher LNP/IMO doses were similar to those seen with ISCOMATRIX™ adjuvant. Groups that received formulations containing IMO alone were weakly immunogenic at all doses tested. It was also observed that the LNP formulations not containing IMO (LNP 14 and LNP16) elicited strong neutralizing responses comparable to the LNP/IMO formulations at the same total lipid dose.

Figure 2:
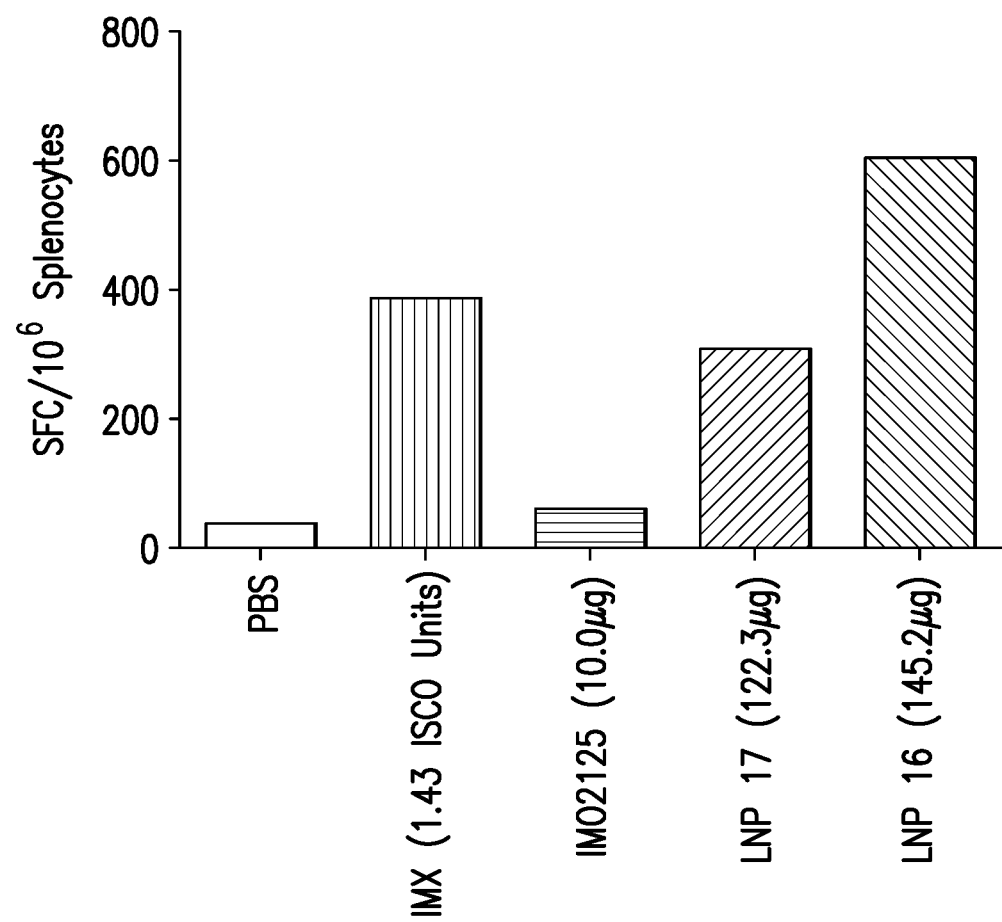
FIG. 2: Total T-cell γ-interferon ELISPOT Responses to DEN2-80E Measured 2 Weeks Post Dose 3. *Responses are not mock subtracted; all mock responses are <50 sfc/1^6 Splenocytes.

The frequencies of DEN2-80E-specific T cells were also determined for select groups by ELISPOT assay with a peptide pool which encompassed the entire DEN2-80E sequence. ELISPOT assays were conducted as described previously. See Casimiro et al., 2002, J. Virol. 76:185. For the assay, spleens were pooled from 5 randomly selected mice per group. The total T-cell γ-interferon ELISPOT responses are presented in FIG. 2. The data demonstrate that both the LNP 17 (with IMO) and LNP 16 (without IMO) formulations elicit strong γ-interferon ELISPOT responses compared to the PBS control and IMO only groups.

Example 5: Testing Lipid Nanoparticles Containing TLR9 Agonist IMO2125 (IMO) as Adjuvants with Hepatitis B Surface Antigen (HBsAg) in Balb/c Mice The objective of this mouse immunogenicity study was to evaluate the ability of LNPs formulated to contain TLR9 agonist IMO2125 (IMO), to adjuvant HBsAg. For the study a dose titration of the LNP 15 and LNP 17 formulations, were evaluated. The dose was based on the combine dosed of LNP components and IMO. For comparison a dose titration of IMO alone was also evaluated at the same dose levels of IMO present in the LNP/IMO formulations. The study also included four additional groups, 1) a no adjuvant control group, 2) a group receiving ISCOMATRIX™ adjuvant (IMX); 3) a group receiving LNP 16 (similar to LNP 17 without IMO) and 4) a group receiving LNP 16 that was mixed with IMO prior to injection.

The candidate vaccine formulations described above were administered as outlined in Table 7. The HBsAg and adjuvants were field mixed to produce the final vaccine formulations just prior to administration. Each vaccine or control formulation was administered to healthy 8-9 week old female Balb/c mice (n=10/group) in 100 µl total volume by intramuscular inoculation (50 µl per quadracept). Two doses of vaccine were administered 2 weeks apart.

TABLE 7

Schedule and Formulations Used in Balb/c Immunogenicity Study

| Group | Mice per group | Antigen dose | Adjuvant* dose | Route | Schedule (Weeks) |
|---|---|---|---|---|---|
| 1 | 10 | 0.2 µg HBsAg | PBS | IM | 0, 2 |
| 2 | 10 | 0.2 µg HBsAg | TMX (1.43 ISCO units) | IM | 0, 2 |
| 3 | 10 | 0.2 µg HBsAg | IMO2125 (0.5 µg) | IM | 0, 2 |
| 4 | 10 | 0.2 µg HBsAg | IMO2125 (1.0 µg) | IM | 0, 2 |
| 5 | 10 | 0.2 µg HBsAg | IMO2125 (5.0 µg) | IM | 0, 2 |
| 6 | 10 | 0.2 µg HBsAg | IMO2125 (10.0 µg) | IM | 0, 2 |
| 7 | 10 | 0.2 µg HBsAg | LNP 17 (6.0 µg) | IM | 0, 2 |
| 8 | 10 | 0.2 µg HBsAg | LNP 17 (12.3 µg) | IM | 0, 2 |
| 9 | 10 | 0.2 µg HBsAg | LNP 17 (61.3 µg) | IM | 0, 2 |
| 10 | 10 | 0.2 µg HBsAg | LNP 17 (122.3 µg) | IM | 0, 2 |
| 11 | 10 | 0.2 µg HBsAg | LNP 15 (8.2 µg) | IM | 0, 2 |
| 12 | 10 | 0.2 µg HBsAg | LNP 15 (16.7 µg) | IM | 0, 2 |
| 13 | 10 | 0.2 µg HBsAg | LNP 15 (83.1 µg) | IM | 0, 2 |
| 14 | 10 | 0.2 µg HBsAg | LNP 15 (166.5 µg) | IM | 0, 2 |
| 15 | 10 | 0.2 µg HBsAg | LNP 16 (145.2 µg) | IM | 0, 2 |
| 16 | 10 | 0.2 µg HBsAg | LNP 16 (145.2 µg) + IMO2125 (10.0 µg) | IM | 0, 2 |

Figure 3:
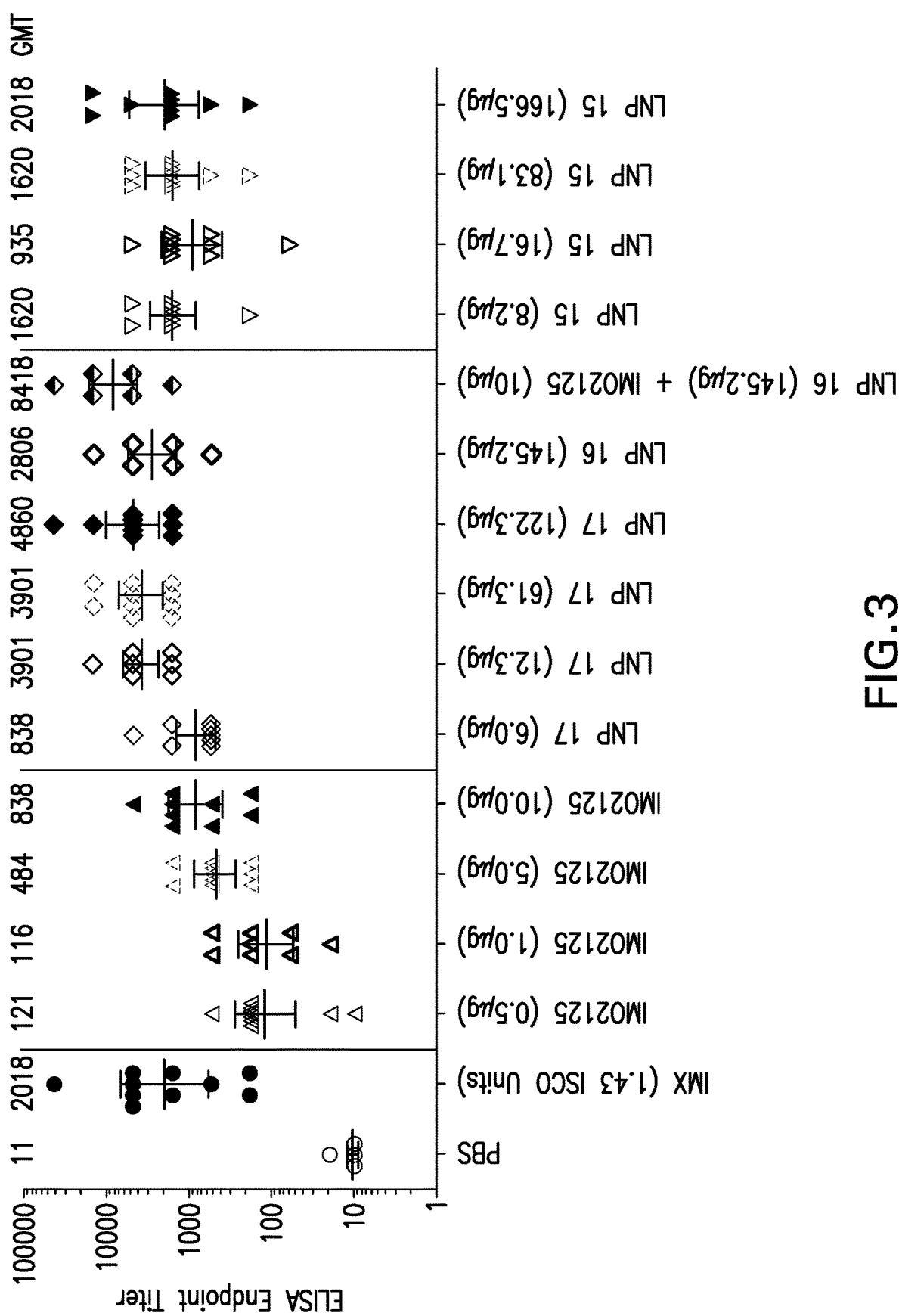
FIG. 3: IgG Endpoint ELISA Titers to HBsAg Measured 2 Weeks Post Dose 2.

IgG ELISA endpoint titers to HBsAg were determined 2 weeks after the final vaccine dose. ELISA titers measured in individual mice are summarized in FIG. 3. The data demonstrate very strong responses for both LNP/IMO formulations with the responses for the LNP 17 formulations trend slightly better than the LNP 15 formulations at comparable doses. All the groups receiving LNP 17 except the low dose group had geometric mean titers that were approximately 2 fold higher than the ISCOMATRIX™ adjuvanted group. The weakest responses were seen in the groups receiving IMO alone. It was also observed that the LNP 16 formulation (no IMO) elicited strong ELISA titers comparable to the LNP 17 formulation at the same total lipid dose. The highest titers were observed in the group that received LNP 16 mixed with IMO prior to injection.

Figure 4:
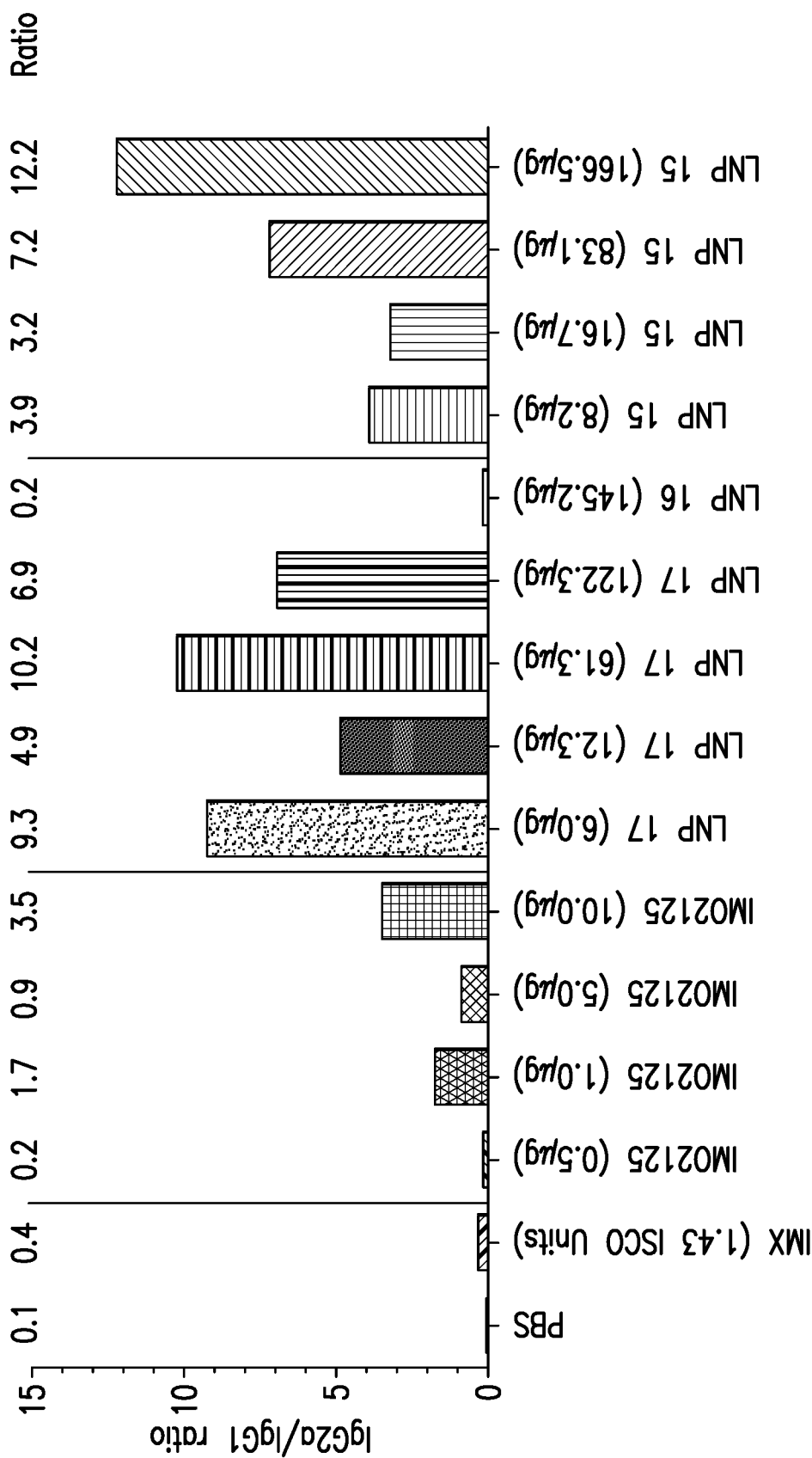
FIG. 4: IgG2a/IgG1 HBsAg ELISA Titer Ratios Measures in Pooled Serum 2 Weeks Post Dose 2.

The IgG isotype profiles were also evaluated to determine if the responses were Th1 or Th2 biased. Serum pools were generated for each group by combining an equal volume of serum from all mice in a group. IgG1 (Th2 biased) and IgG2a (Th1 biased) titers were then determined for the serum pools using an isotype specific ELISA. Ratios of the IgG2a/IgG1 ELISA titers are presented in FIG. 4. The LNP 15 and LNP 17 formulations elicited strong Th1 biased responses (ratio>2). The Th1 bias appears to be dependent on the presence of IMO2125 in the formulation as the responses in the mice receiving LNP 16 were skewed towards a Th2 response.

Figure 5:
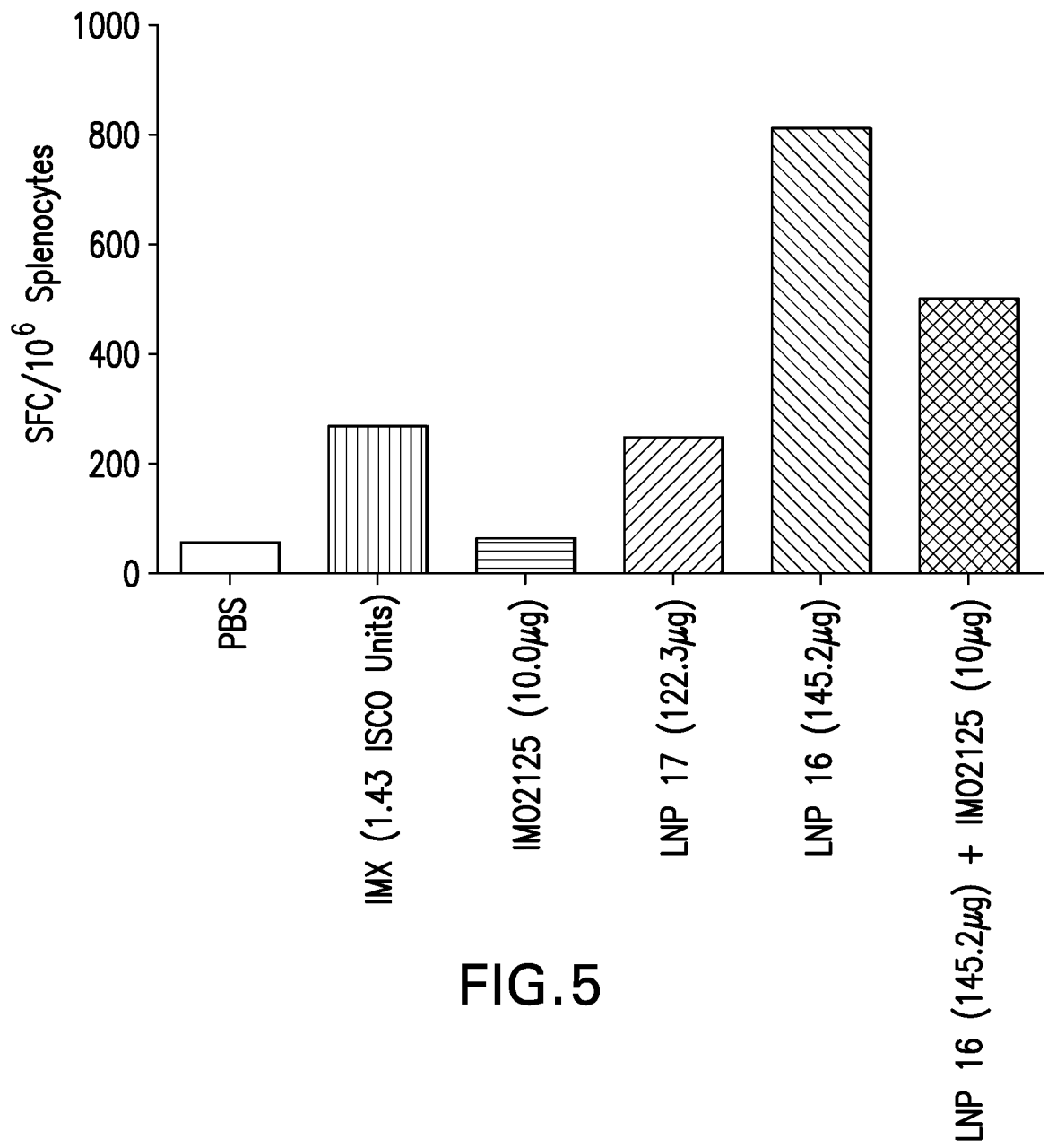
FIG. 5: Total T-cell γ-interferon ELISPOT Responses to HBsAg Measured 2 Weeks Post Dose 2.

The frequencies of HBsAg-specific T cells were also determined for select groups by ELISPOT assay with a peptide pool which encompassed the entire HBsAg sequence. See Casimiro et al., 2002, J. Virol. 76:185. For the assay spleens were pooled from 5 randomly selected mice per group. The total T-cell γ-interferon ELISPOT responses are presented in FIG. 5. The data demonstrate that the LNP 17, LNP 16 and LNP 16 mixed with IMO, formulations elicit strong γ-interferon ELISPOT responses compared to the PBS control and IMO only groups.

Example 6: Testing Lipid Nanoparticles as Adjuvants with Hepatitis B Surface Antigen (HBsAg) in Balb/c Mice The objective of this mouse immunogenicity study was to evaluate the ability of LNPs, to adjuvant HBsAg and compare the responses to other adjuvants. For the study a dose titration of the LNP 16 formulation (1, 5, 25 or 125 µg) was evaluated. The dose corresponds to the combined dose of all LNP components in the formulation. The LNP's were compared to groups receiving, 1) no adjuvant, 2) amorphous aluminum hydroxylphosphate sulfate (AAHS), 3) ISCO-MATRIX™ adjuvant (IMX); 4) TLR9 agonist IMO2125 (IMO), 5) Monophosphoyl Lipid A (MPL), 6) a combination of MPL and AAHS, 7) LNP 16 mixed with IMO2125 and 8) LNP 16 mixed with MPL.

The candidate vaccine formulations described above were administered as outlined in Table 8. The HBsAg and adjuvants were field mixed to produce the final vaccine formulations just prior to administration. Each vaccine or control formulation was administered to healthy 8-9 week old female Balb/c mice (n=10/group) in 100 µl total volume by intramuscular (IM) inoculation (50 µl per quadracept). Two doses of vaccine were administered 2 weeks apart.

TABLE 8

Schedule and Formulations Used in Balb/c Immunogenicity Study

| Group | Mice per group | Antigen dose | Adjuvant dose* | Route | Schedule (Weeks) |
|---|---|---|---|---|---|
| 1 | 10 | 0.2 µg HBsAg | PBS | IM | 0, 2 |
| 2 | 10 | 0.2 µg HBsAg | AAHS (45.0 µg) | IM | 0, 2 |
| 3 | 10 | 0.2 µg HBsAg | TMX (1.43 ISCO units) | IM | 0, 2 |
| 4 | 10 | 0.2 µg HBsAg | IMO2125 (5.0 µg) | IM | 0, 2 |
| 5 | 10 | 0.2 µg HBsAg | MPL (5.0 µg) | IM | 0, 2 |
| 6 | 10 | 0.2 µg HBsAg | AAHS (45.0 µg) + MPL (5.0 µg) | IM | 0, 2 |
| 7 | 10 | 0.2 µg HBsAg | LNP 16 (1.0 µg) | IM | 0, 2 |
| 8 | 10 | 0.2 µg HBsAg | LNP 16 (5.0 µg) | IM | 0, 2 |
| 9 | 10 | 0.2 µg HBsAg | LNP 16 (25 µg) | IM | 0, 2 |
| 10 | 10 | 0.2 µg HBsAg | LNP 16 (125 µg) | IM | 0, 2 |
| 11 | 10 | 0.2 µg HBsAg | LNP 16 (25 µg) + IMO2125 (5.0 µg) | IM | 0, 2 |
| 12 | 10 | 0.2 µg HBsAg | LNP 16 (25 µg) + MPL (5.0 µg) | IM | 0, 2 |

Figure 6:
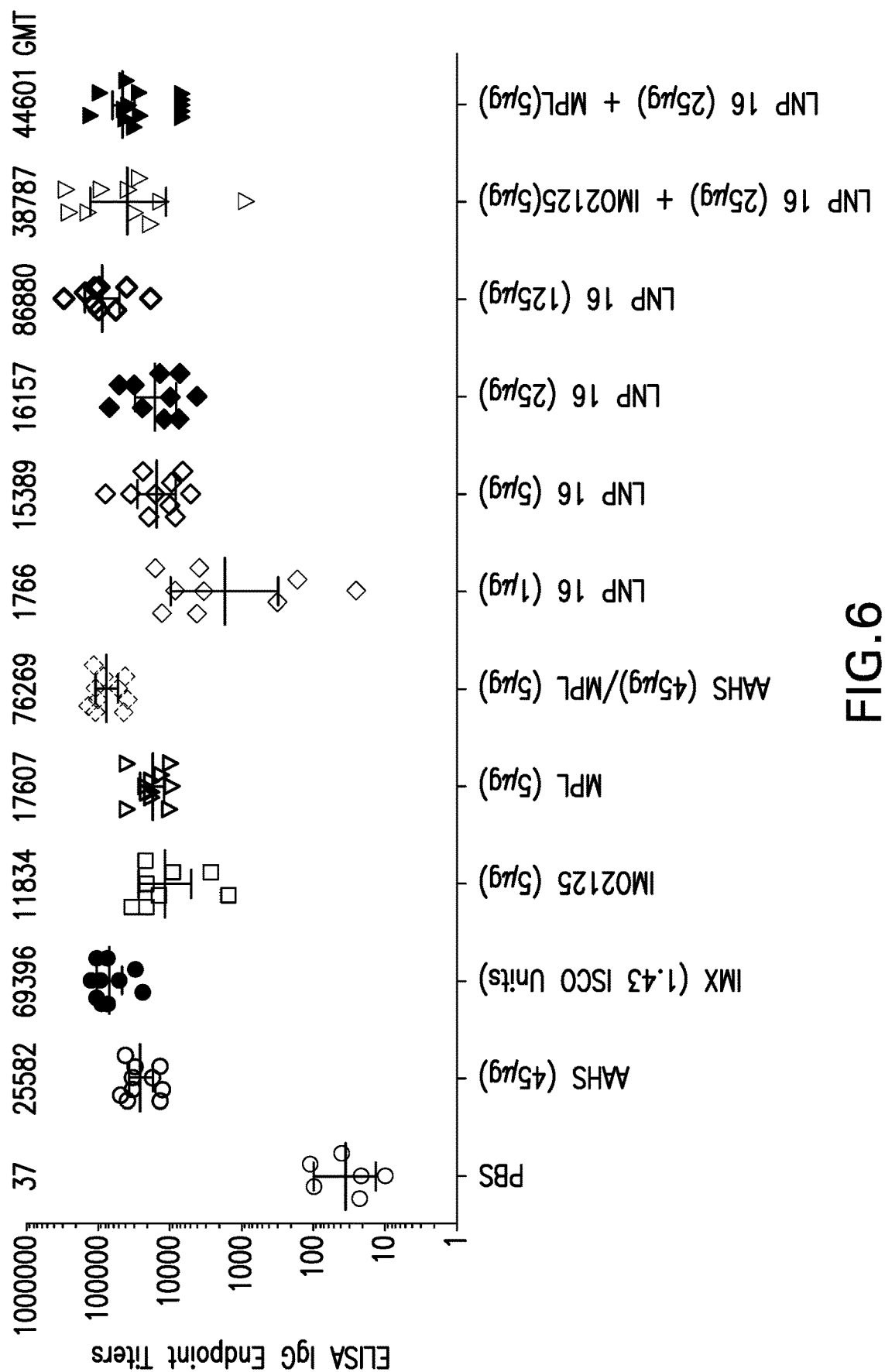
FIG. 6: IgG Endpoint ELISA Titers to HBsAg Measured 2 Weeks Post Dose 2.

IgG ELISA endpoint titers to HBsAg were determined 2 weeks after the final vaccine dose. ELISA titers measured in individual mice are summarized in FIG. 6. The data demonstrate a dose dependent response for the LNP 16 formulation. The high dose of LNP 16 (125 µg) resulted in a group geometric mean titer that was higher than any other adjuvant tested. Combining LNP 16 with either IMO2125 or MPL resulted in a 2.5 and 3 fold increase in the GMT respectively, compared to the same dose of LNP 16 alone.

Figure 7:
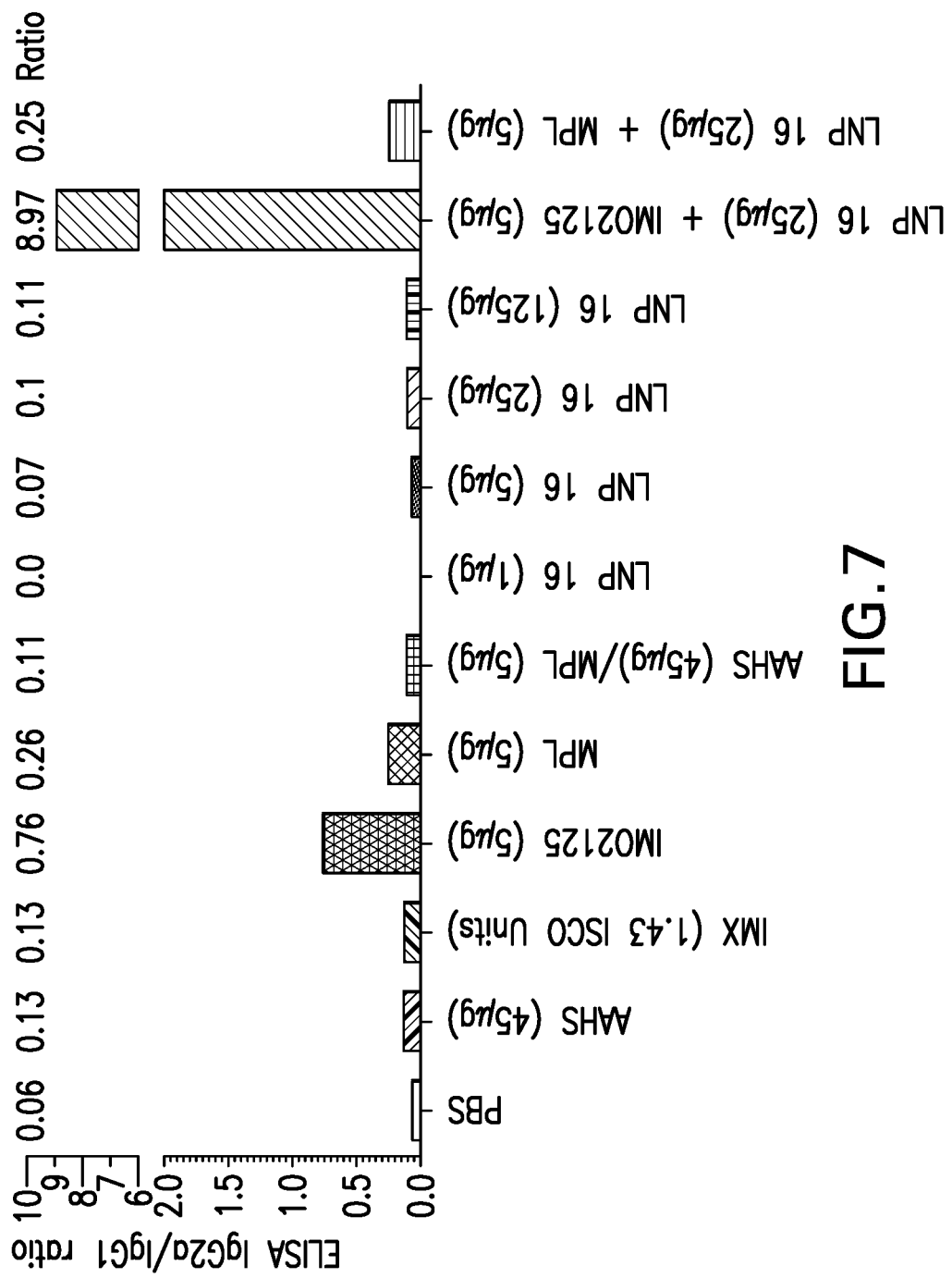
FIG. 7: IgG2a/IgG1 HBsAg ELISA Titer Ratios Measures in Pooled Serum 2 Weeks Post Dose 2.

The IgG isotype profiles were also evaluated to determine if the responses were Th1 or Th2 biased. Serum pools were generated for each group by combining an equal volume of serum from all mice in a group. IgG1 (Th2 biased) and IgG2a (Th1 biased) titers were then determined for the serum pools. Ratios of the IgG2a/IgG1 titers are presented in FIG. 7. The responses elicited by the LNP 16 formulation were Th2 biased (ratio<0.5) but could be shifted to a Th1 response (ratio>2) by mixing LNP 16 with IMO2125.

Figure 8:
FIG. 8: Total, CD4 and CD8 T-cell γ-interferon ELISPOT Responses to HBsAg Measured 2 Weeks Post Dose 2. *Not mock subtracted; all mock responses are <50 sfc/10^6 Splenocytes

The frequencies of HBsAg-specific T cells were also determined by ELISPOT assay with a peptide pool which encompassed the entire HBsAg sequence. Total T-cell, as well as CD4 and CD8 γ-interferon ELISPOT responses to HBsAg were also measured and are presented in FIG. 8. The data demonstrate a dose dependent T cell response for the LNP 16 formulation with T-cell responses significantly stronger than those elicited by any other adjuvant tested. The data also shows that the LNP 16 formulation elicits both strong CD4 and CD8 responses.

Example 7: Evaluating the Impact of Lipid Manoparticles Size on the Ability to Adjuvant Responses to Hepatitis B Surface Antigen (HBsAg) in Balb/C Mice The objective of this mouse immunogenicity study was to, 1) evaluate the ability of LNP 14, to adjuvant HBsAg, 2) to evaluate the impact of LNP size on adjuvant properties and 3) to evaluate the impact of % PEG content in the LNP on adjuvanticity. For the evaluation of the LNP 14 formulation, a dose titration based on total lipid content (1, 5, 25 or 125 µg) was evaluated. The relationship between LNP size and adjuvant properties was evaluated by studying four different size LNPs (LNP 25, 60 nm; LNP 16, 89 nm; LNP 26, 156 nm; and LNP 27, 239 nm). The relationship between LNP PEG content and adjuvant properties was evaluated by studying LNPs with either 1% (LNP 19) or 2% PEG (LNP 16).

The candidate vaccine formulations described above were administered as outlined in Table 9. The HBsAg and adjuvants were field mixed to produce the final vaccine formulations just prior to administration. Each vaccine or control formulation was administered to healthy 8-9 week old female Balb/c mice (n=10/group) in 100 µl total volume by intramuscular inoculation (50 µl per quadracept). Two doses of vaccine were administered 2 weeks apart.

TABLE 9

Schedule and Formulations Used in Balb/c Immunogenicity Study

| Group | Mice per group | Antigen dose | Adjuvant dose* | Route | Schedule (Weeks) |
|---|---|---|---|---|---|
| 1 | 10 | 0.2 µg HBsAg | PBS | IM | 0, 2 |
| 2 | 10 | 0.2 µg HBsAg | AAHS (45.0 µg) | IM | 0, 2 |
| 3 | 10 | 0.2 µg HBsAg | LNP 14 (1.0 µg) | IM | 0, 2 |

TABLE 9-continued

Schedule and Formulations Used in Balb/c Immunogenicity Study

| Group | Mice per group | Antigen dose | Adjuvant dose* | Route | Schedule (Weeks) |
|---|---|---|---|---|---|
| 4 | 10 | 0.2 µg HBsAg | LNP 14 (5.0 µg) | IM | 0, 2 |
| 5 | 10 | 0.2 µg HBsAg | LNP 14 (25 µg) | IM | 0, 2 |
| 6 | 10 | 0.2 µg HBsAg | LNP 14 (125 µg) | IM | 0, 2 |
| 7 | 10 | 0.2 µg HBsAg | LNP 25 (60 nm) (1.0 µg) | IM | 0, 2 |
| 8 | 10 | 0.2 µg HBsAg | LNP 25 (60 nm) (5.0 µg) | IM | 0, 2 |
| 9 | 10 | 0.2 µg HBsAg | LNP 16 (89 nm) (1.0 µg) | IM | 0, 2 |
| 10 | 10 | 0.2 µg HBsAg | LNP 16 (89 nm) (5.0 µg) | IM | 0, 2 |
| 11 | 10 | 0.2 µg HBsAg | LNP 26 (156 nm) (1.0 µg) | IM | 0, 2 |
| 12 | 10 | 0.2 µg HBsAg | LNP 26 (156 nm) (5.0 µg) | IM | 0, 2 |
| 13 | 10 | 0.2 µg HBsAg | LNP 27 (239 nm) (1.0 µg) | IM | 0, 2 |
| 14 | 10 | 0.2 µg HBsAg | LNP 27 (239 nm) (5.0 µg) | IM | 0, 2 |
| 15 | 10 | 0.2 µg HBsAg | LNP 19 (1.0 µg) | IM | 0, 2 |
| 16 | 10 | 0.2 µg HBsAg | LNP 19 (5.0 µg) | IM | 0, 2 |

Figure 9:
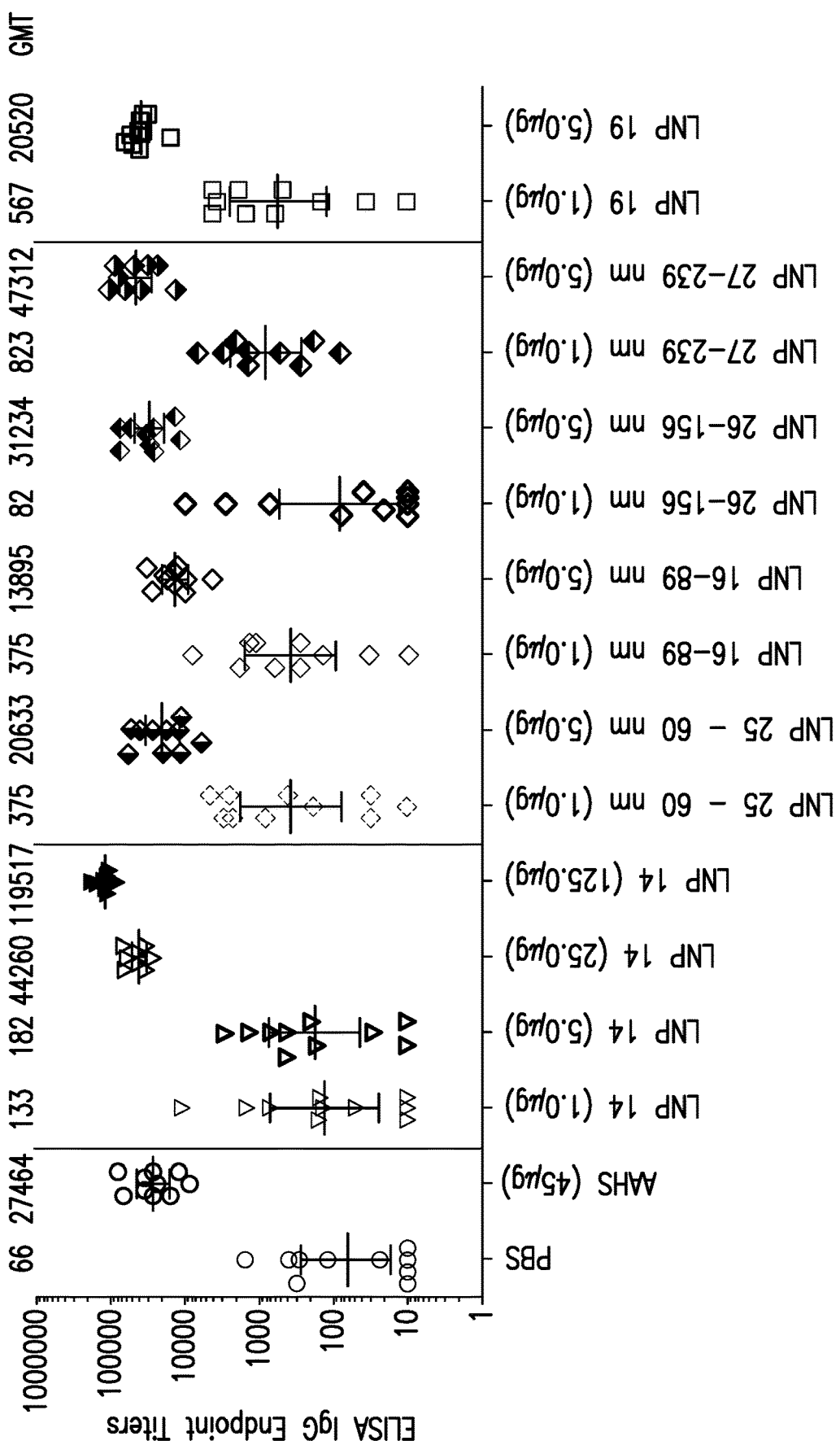
FIG. 9: IgG Endpoint ELISA Titers to HBsAg Measured 2 Weeks Post Dose 2.

IgG ELISA endpoint titers to HBsAg were determined 2 weeks after the final vaccine dose. ELISA titers measured in individual mice are summarized in FIG. 9. The data demonstrate a dose dependent response for the LNP 14 formulation. The high dose of LNP 14 (125 µg) resulted in a group geometric mean titer that was 4 fold higher than the AAHS control group. The data also indicate that neither LNP size nor PEG concentration strongly impact the adjuvant properties of the LNPs over the ranges tested.

Figure 10:
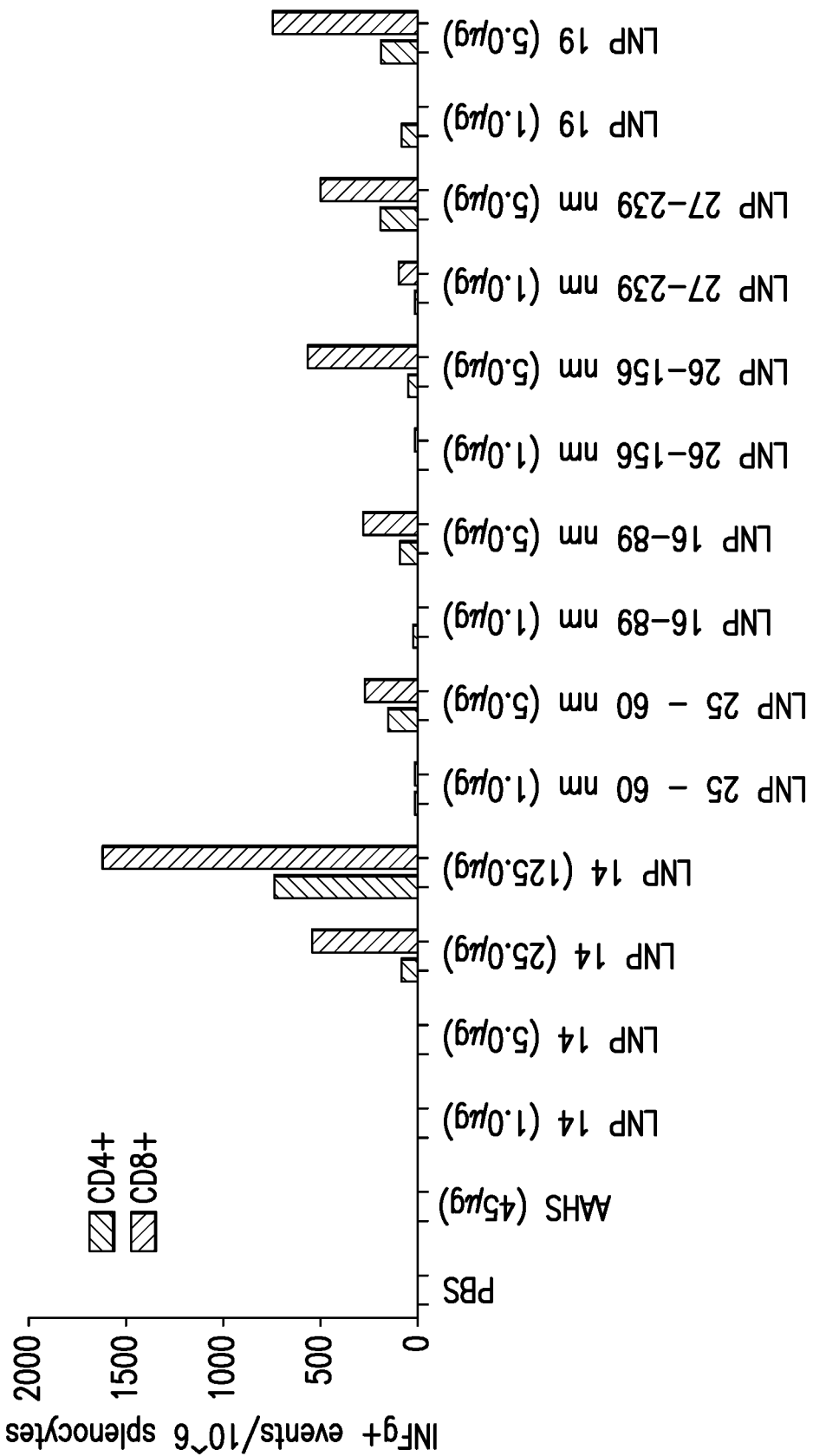
FIG. 10: CD4 and CD8 T-cell γ-interferon ELISPOT Responses to HBsAg Measured 2 Weeks Post Dose 2. *Responses are mock subtracted

CD4 and CD8 γ-interferon ELISPOT responses to HBsAg were also measured by flow cytometry and are presented in FIG. 10. The data demonstrate a dose dependent T cell response for the LNP 14 formulation with T-cell responses significantly higher than those elicited by AAHS. The data also shows that the LNP 14 formulation elicits both strong CD4 and CD8 responses. The data also indicate the neither LNP size or PEG concentration strongly impact the ability of the LNP's to elicit a strong CD4 and CD8 T cell response.

Example 8: Testing Lipid Nanoparticles Alone or Lipid Nanoparticles Containing or Mixed with TLR9 Agonist IMO2125 as Adjuvants with Hepatitis B Surface Antigen (HBsAg) in Balb/c Mice A mouse immunogenicity study was performed to compare the adjuvant properties of LNPs alone (LNP 16), LNPs formulated to contain TLR9 agonist IMO2125 (IMO) (LNP 17) and LNP's mixed with the same dose of IMO prior to injection (LNP16+ IMO). For the study, HBsAg was used as a model antigen. A dose titration of LNP 16, LNP 17 and LNP16 + IMO prior to injection were evaluated. The doses evaluated in the LNP 16+ IMO mixtures were selected to match the dose of each adjuvant component in the LNP 17 formulations. The study also included five additional groups: 1) a no adjuvant control group; 2) a group receiving amorphous aluminum hydroxylphosphate sulfate (AAHS); 3) a group receiving ISCOMATRIX™ adjuvant (IMX); 4) a group receiving low dose IMO; and 5) a group receiving high dose IMO.

The candidate vaccine formulations described above were administered as outlined in Table 10. HBsAg and adjuvants were field mixed to produce the final vaccine formulations just prior to administration. Each vaccine or control formulation was administered to healthy 8-9 week old female Balb/c mice (n=10/group) in 100 µl total volume by intramuscular inoculation (50 µl per quadricep). Two doses of vaccine were administered 2 weeks apart.

TABLE 10

Schedule and Formulations Used in Balb/c Immunogenicity Study

| Group | Mice per group | Antigen dose | Adjuvant dose | Route | Schedule (Weeks) |
|---|---|---|---|---|---|
| 1 | 10 | 0.2 µg HBsAg | PBS | IM | 0, 2 |
| 2 | 10 | 0.2 µg HBsAg | AAHS (45 µg) | IM | 0, 2 |
| 3 | 10 | 0.2 µg HBsAg | TMX (1.43 ISCO units) | IM | 0, 2 |
| 4 | 10 | 0.2 µg HBsAg | IMO2125 (2.0 µg) | IM | 0, 2 |
| 5 | 10 | 0.2 µg HBsAg | IMO2125 (10.0 µg) | IM | 0, 2 |
| 6 | 10 | 0.2 µg HBsAg | LNP 16 (1.0 µg) | IM | 0, 2 |
| 7 | 10 | 0.2 µg HBsAg | LNP 16 (5.0 µg) | IM | 0, 2 |
| 8 | 10 | 0.2 µg HBsAg | LNP 16 (25.0 µg) | IM | 0, 2 |
| 9 | 10 | 0.2 µg HBsAg | LNP 16 (125.0 µg) | IM | 0, 2 |
| 10 | 10 | 0.2 µg HBsAg | LNP 17 (1.08 µg) | IM | 0, 2 |
| 11 | 10 | 0.2 µg HBsAg | LNP 17 (5.38 µg) | IM | 0, 2 |
| 12 | 10 | 0.2 µg HBsAg | LNP 17 (26.9 µg) | IM | 0, 2 |
| 13 | 10 | 0.2 µg HBsAg | LNP 17 (134.4 µg) | IM | 0, 2 |
| 14 | 10 | 0.2 µg HBsAg | LNP 16 (1.0 µg) + IMO2125 (0.08 µg) | IM | 0, 2 |
| 15 | 10 | 0.2 µg HBsAg | LNP 16 (5.0 µg) + IMO2125 (0.38 µg) | IM | 0, 2 |
| 16 | 10 | 0.2 µg HBsAg | LNP 16 (25.0 µg) + IMO2125 (1.9 µg) | IM | 0, 2 |
| 17 | 10 | 0.2 µg HBsAg | LNP 16 (125.0 µg) + IMO2125 (9.4 µg) | IM | 0, 2 |

Figure 11:
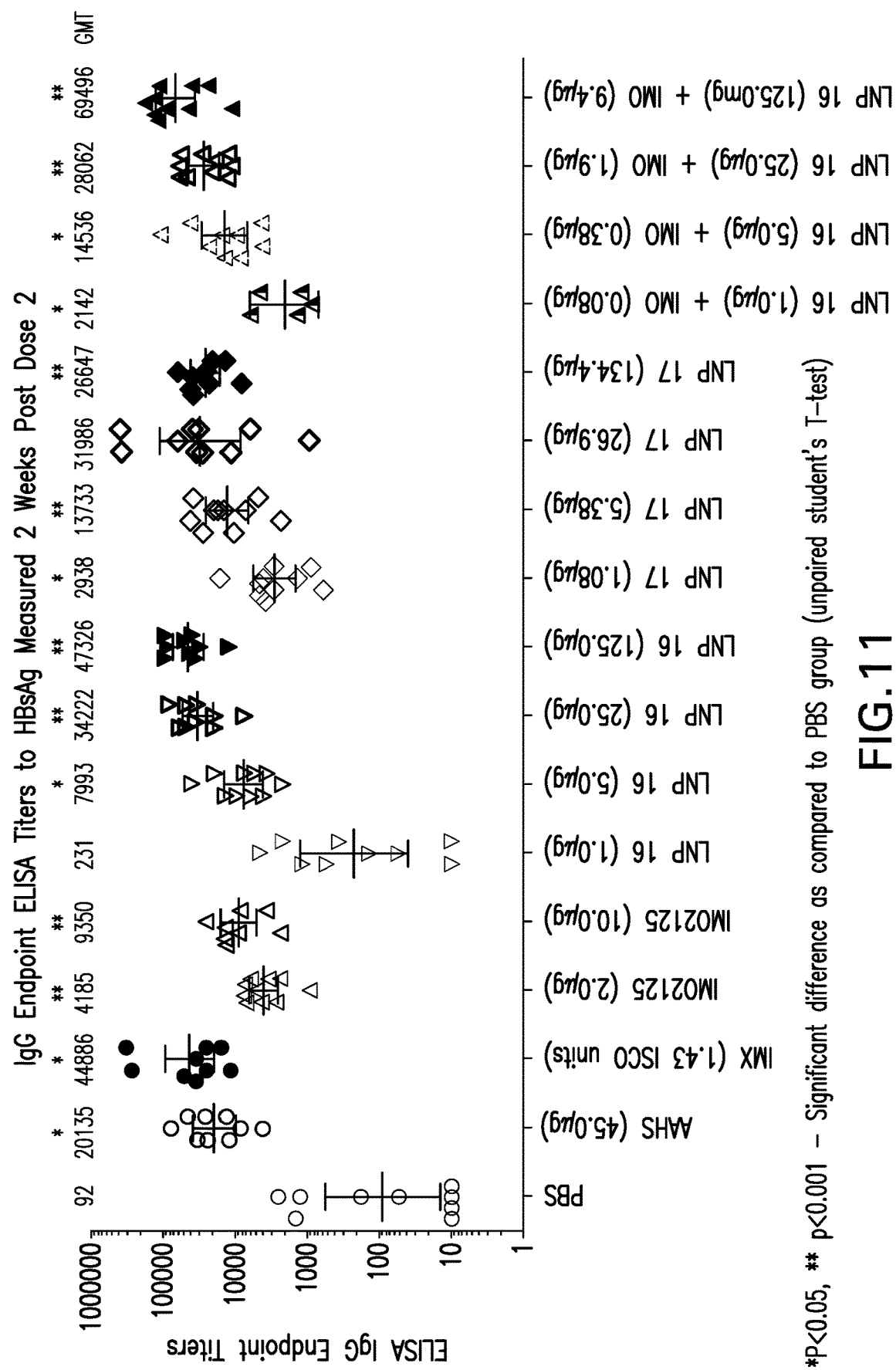
FIG. 11: IgG Endpoint ELISA Titers to HBsAg Measured 2 Weeks Post Dose 2.

IgG ELISA endpoint titers to HBsAg were determined 2 weeks after the final vaccine dose. ELISA titers measured in individual mice are summarized in FIG. 11. A statistically significant, dose-dependent, increase in total IgG responses to HBsAg was observed in almost all groups that received an adjuvant in comparison to the PBS control group. The data demonstrate very strong and comparable responses from LNPs formulated to contain IMO (LNP 17) and LNP's mixed with IMO (LNP16+ IMO) at the various dose levels evaluated. The responses measured in the groups receiving LNP alone (LNP 16) were also comparable to the groups receiving the combination of LNP and IMO (LNP 17 or LNP16+ IMO) at the higher total lipid doses of LNP evaluated, but the inclusion of IMO seemed to improve the consistency of the response in the low dose (1.0 µg LNP) group. The weakest responses were seen in the groups receiving IMO alone. As observed in previous studies, the responses measured in the groups that received the higher LNP doses were comparable to those measures in the group that received ISCOMATRIX™ and AAHS, an aluminum based adjuvant.

Figure 12:
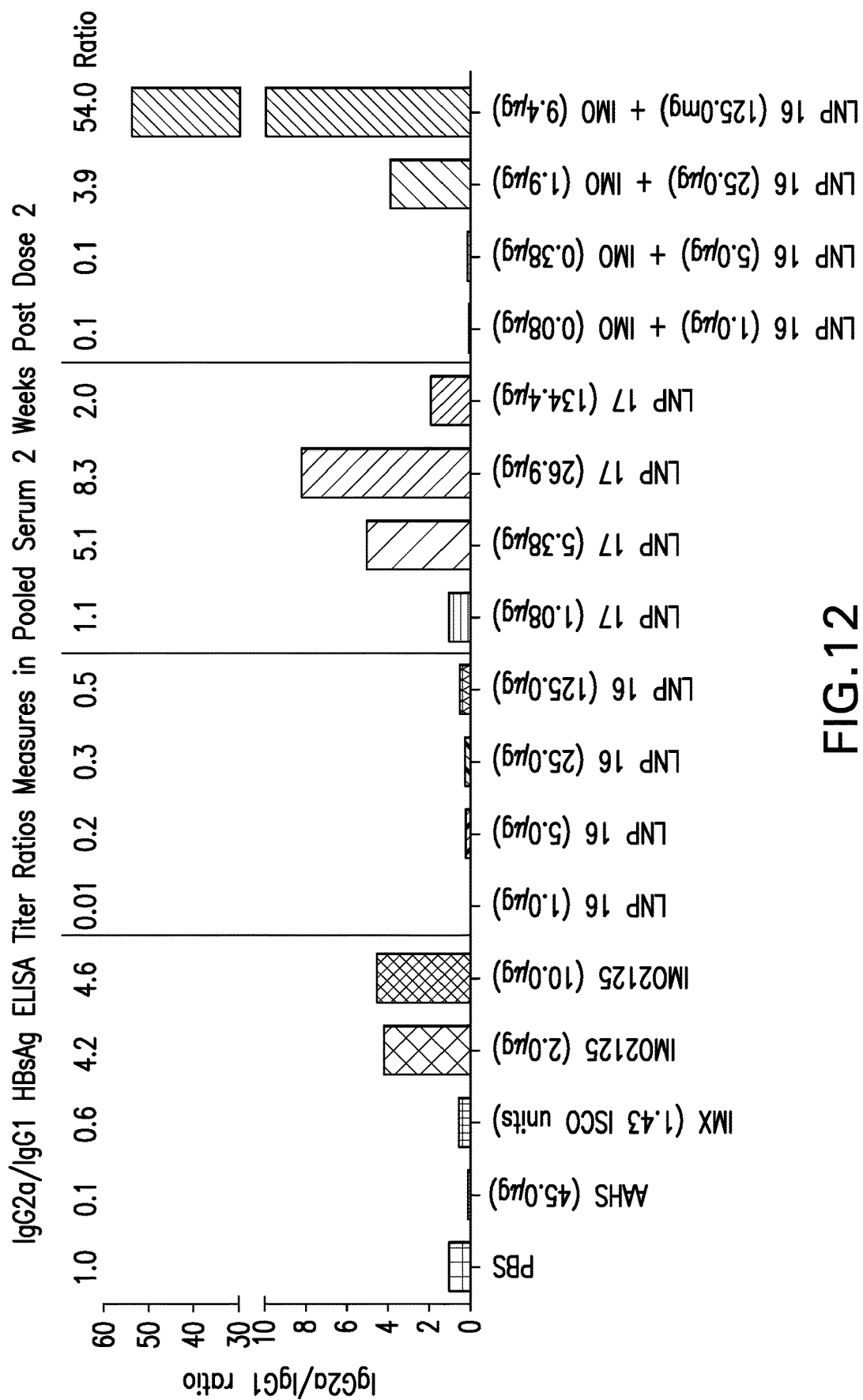
FIG. 12: IgG2a/IgG1 HBsAg ELISA Titer Ratios Measures in Pooled Serum 2 Weeks Post Dose 2.

The IgG isotype profiles were also evaluated to determine if the responses were Th1 or Th2 biased. Serum pools were generated for each group by combining an equal volume of serum from all mice in a group. HBsAg specific IgG1 (Th2 biased) and IgG2a (Th1 biased) titers were then determined for the serum pools. Ratios of the IgG2a/IgG1 ELISA titers are shown in FIG. 12. As seen in previous studies, LNP 17 and LNP 16+ IMO formulations can elicit strong Th1 biased responses (ratio>2) depending on the dose of IMO2125 present in the formulation. LNP 17 doses containing less than 0.38 µg of IMO and LNP 16+ IMO doses containing less than 1.9 µg of IMO did not result in Th1 biased responses. As seen previously all dose levels of LNP 16 were skewed towards a Th2 response. These results suggest that in spite of a comparable boost in total IgG responses to HBsAg by LNP16, LNP17 and LNP16+ IMO formulations, only the encapsulation or combination of LNP with IMO resulted in a Th1-type class switch in IgG responses.

Figure 13A:
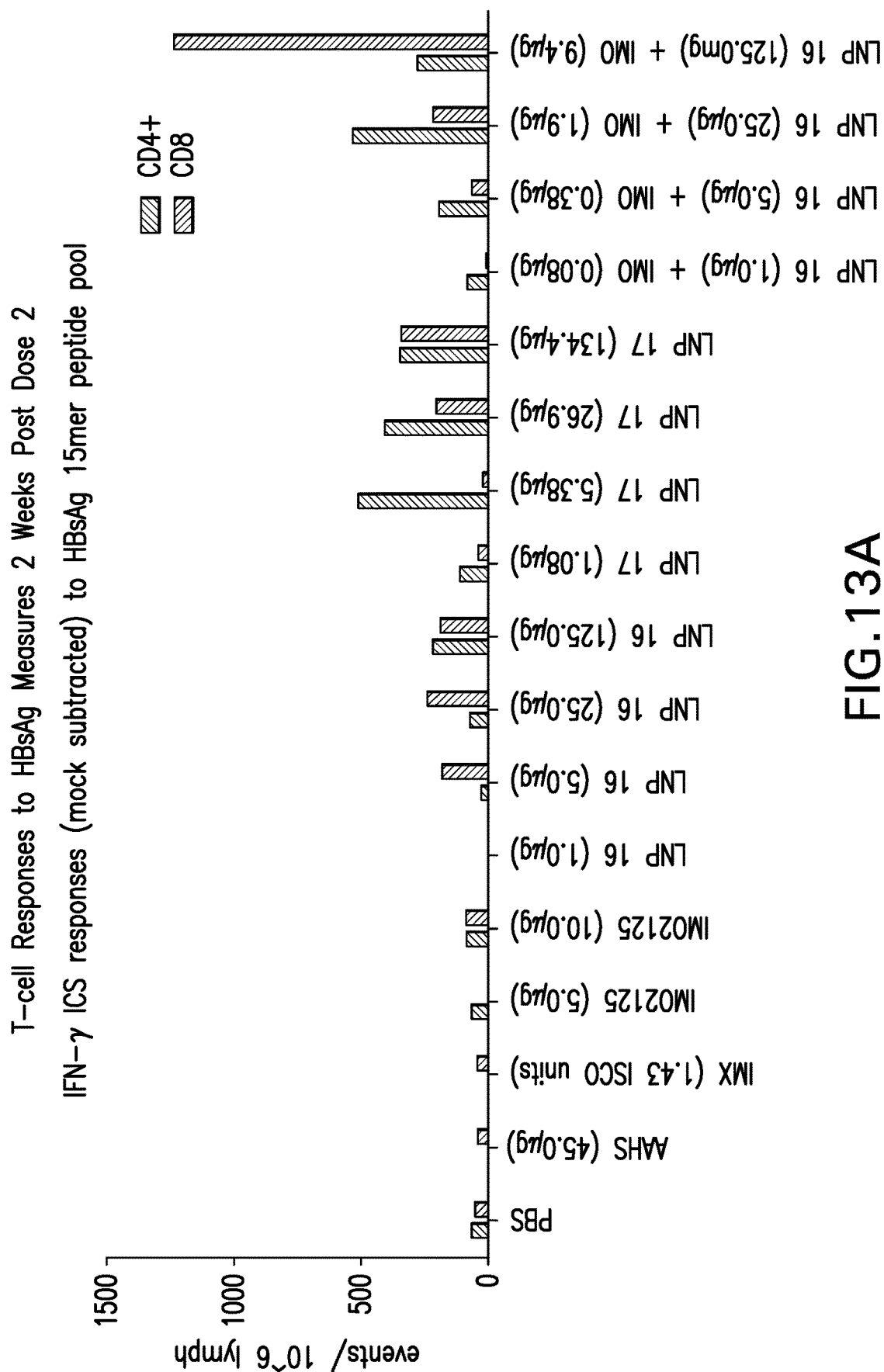
FIG. 13A-C: T-cell Responses to HBsAg Measured 2 Weeks Post Dose 2. A: IFN-γ ICS responses (mock subtracted) to HBsAg 15 mer peptide pool; B: TNF-α ICS responses (mock subtracted) to HBsAg 15 mer peptide pool; C: IL-10 ICS responses (mock subtracted) to HBsAg 15 mer peptide pool.
Figure 13B:
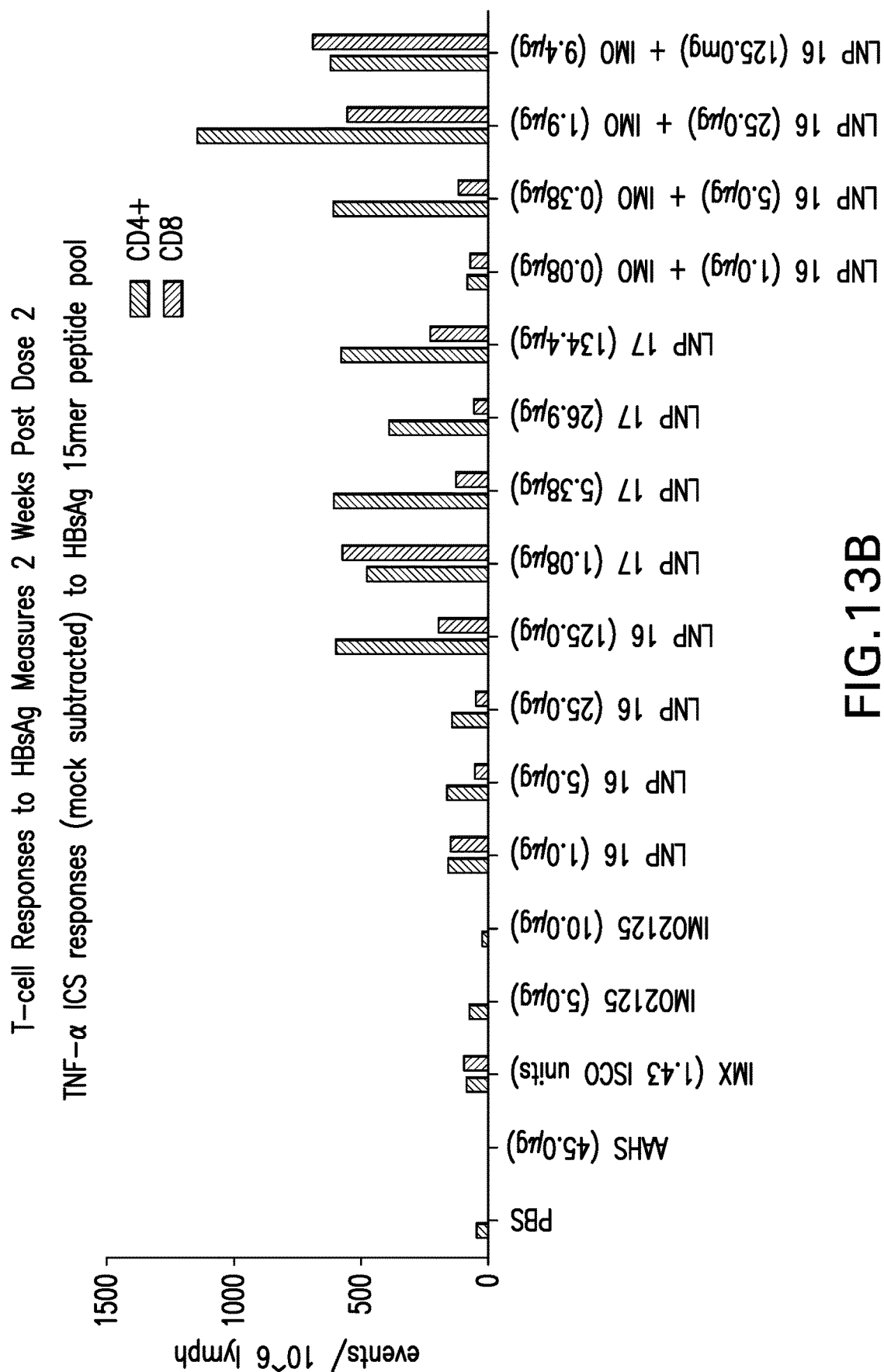
Figure 13C:
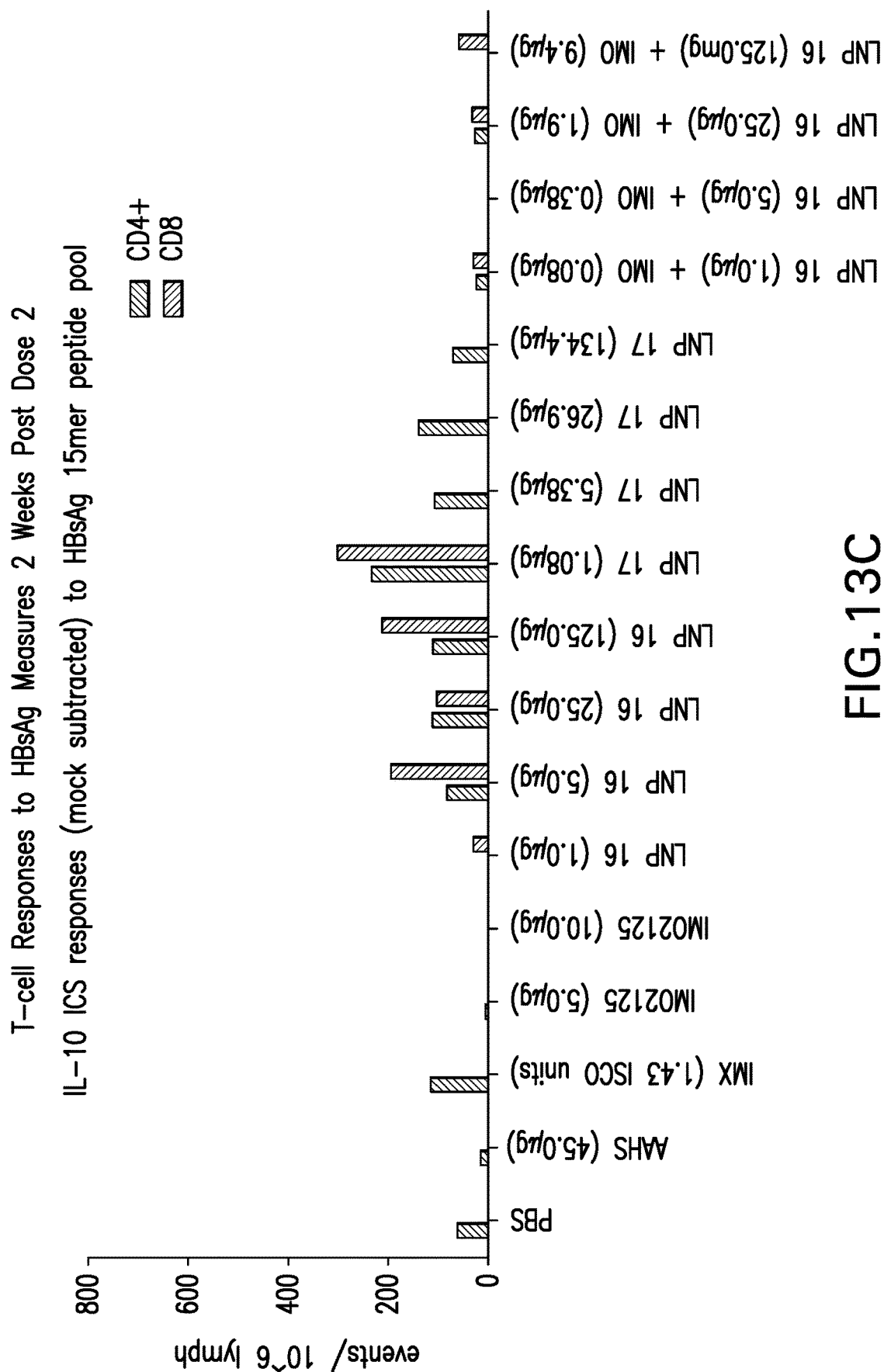
Figure 14:
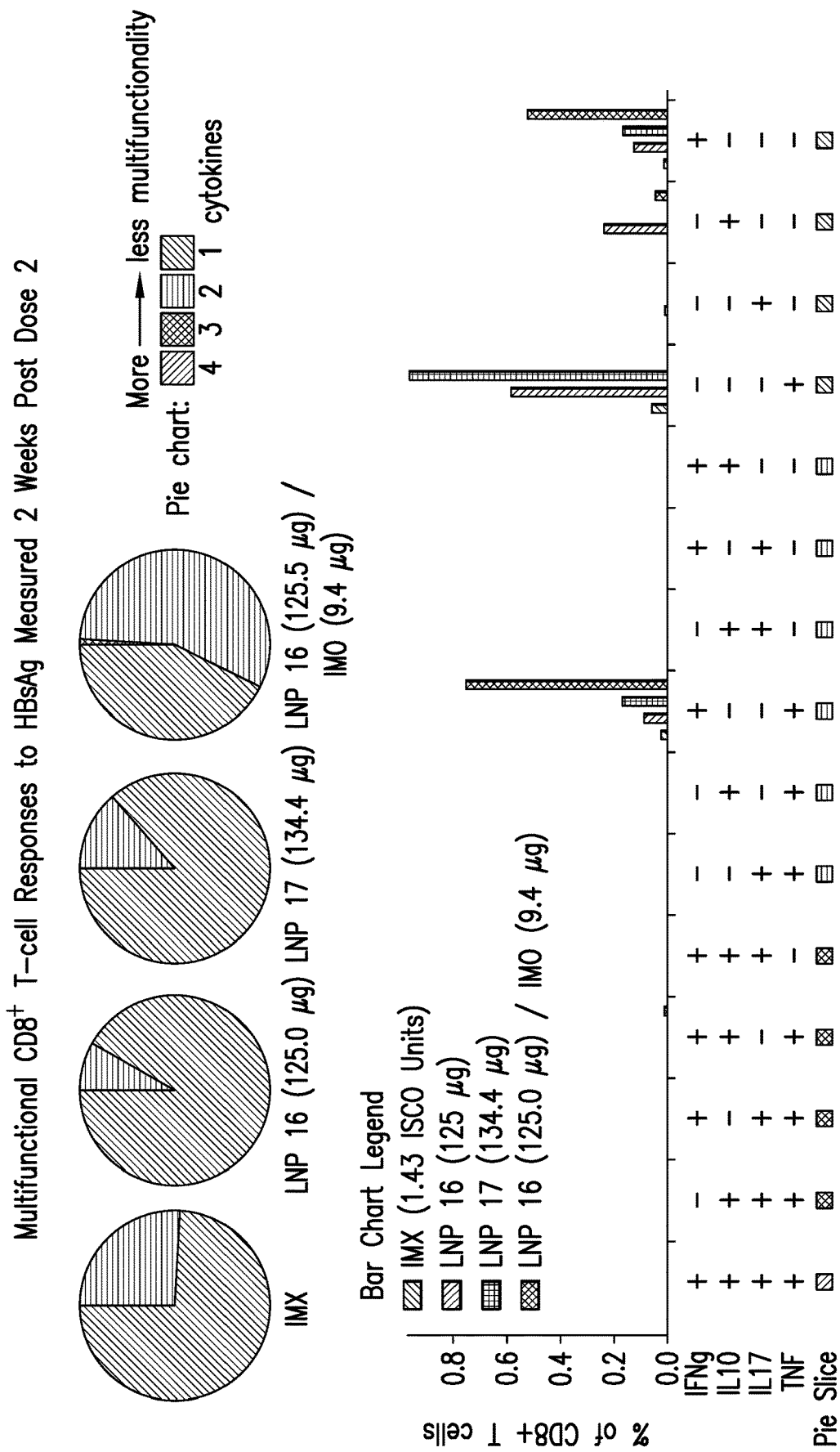
FIG. 14: Multifunctional CD8+ T-cell Responses to HBsAg Measured 2 Weeks Post Dose 2.

Cell-mediated immune responses to HBsAg were evaluated in mice from the aforementioned immunization groups. For this assay spleens were pooled from 5 randomly selected mice per group. Processed splenocytes were stimulated with a pool of peptides covering the whole amino acid sequence for HBsAg. Then, spleens were stained for intracellular expression of IFN-γ, TNF-α, IL-10, and IL-17 and assessed by flow cytometry. The results for CD4$^+$ and CD8$^+$ T cells expressing IFN-γ, TNF-α and IL-10, are shown in FIG. 13. Formulations containing LNPs either with or without IMO increased T cell responses as compared to AAHS, IMX or IMO alone. Although not dose dependent, CD4$^+$ T cell responses to HBsAg were higher in the LNP 17 and LNP 16+ IMO groups as compared to LNP 16 alone. While the frequency of HBsAg specific IFN-γ expressing CD8$^+$ T cells were modestly increased in LNP 16 alone group, the encapsulation or addition of IMO (LNP 17/LNP 16+ IMO), led to much greater boost in the frequency of these cells. In addition, the frequency of TNF-α expressing CD4$^+$ and CD8$^+$ T cells were much higher in LNP 17 or LNP 16+ IMO groups than for LNP alone. In contrast, more IL-10 was induced by LNP alone (LNP 16) than with the LNP/IMO coformulations. No significant staining was seen for IL-17. The percent of multifunctional CD8$^+$ T cells for the IMX and high dose LNP 16, LNP 17 and LNP 16+ IMO groups is summarized in FIG. 14. Overall, these results demonstrate that groups that received LNP 17 and LNP 16+ IMO induced higher rates of multifunctional CD8$^+$ T cells of the IFN-γ$^+$, TNF-α$^+$ phenotype than the LNP16 group. But, all groups that received LNP formulations (LNP 16, LNP 17 & LNP 16+ IMO) showed a definite increase in HBsAg specific CD8$^+$ T cells responses compared to groups receiving AAHS, IMX or IMO alone.

In conclusion, these studies pertaining to HBsAg strongly suggest that LNP alone or LNP/IMO formulations confer potent adjuvant properties in enhancing both B and T cell immune responses. Furthermore, the encapsulation or formulation of IMO with LNP increases the quality of immune responses by inducing a more Th1-type B-cell responses and by boosting the frequency of multi-functional CD8$^+$ T cell responses to HBsAg.

What is claimed is:

1. A composition comprising:
   a) a lipid nanoparticles ("LNP") adjuvant comprising (13Z,16Z)-N,N-dimethyl-3-nonyldocosa-13,16-dien-1-amine, wherein the LNP adjuvant comprises 34-59 mole % (13Z,16Z)-N,N-dimethyl-3-nonyldocosa-13,16-dien-1-amine, 30-48 mole % cholesterol, 10-24% DSPC and 1-2 mole % PEG-DMG; and
   b) one or more antigens;
   wherein the composition provides an increased CD4+T-cell response to the one or more antigens compared to a CD4+ T-cell response to the one or more antigens provided by the composition in the absence of the LNP adjuvant.

2. The composition of claim 1, further comprising one or more agonists selected from Toll-like receptors (TLR) agonists and Stimulator of Interferon Gene (STING) agonists.

3. The composition of claim 1, further comprising an immunostimulatory agent selected from saponin, squalene, aluminum phosphate and aluminum hydroxide.

4. The composition of claim 1, wherein the composition is in the form of an aerosol, dispersion, solution, or suspension.

5. A method of immunizing a subject comprising administering to the subject an effective amount of the composition of claim 1.

6. A composition comprising:
   a) a lipid nanoparticles ("LNP") adjuvant comprising (13Z,16Z)-N,N-dimethyl-3-nonyldocosa-13,16-dien-1-amine, wherein the LNP adjuvant comprises 34-59 mole % (13Z,16Z)-N,N-dimethyl-3-nonyldocosa-13,16-dien-1-amine, 30-48 mole % cholesterol, 10-24% DSPC and 1-2 mole % PEG-DMG; and
   b) one or more antigens;
   wherein the composition provides an enhanced antibody response to the one or more antigens compared to an antibody response to the one or more antigens provided by the composition in the absence of the LNP adjuvant.

7. The composition of claim 6, further comprising one or more agonists selected from Toll-like receptors (TLR) agonists and Stimulator of Interferon Gene (STING) agonists.

8. The composition of claim 6, further comprising an immunostimulatory agent selected from saponin, squalene, aluminum phosphate and aluminum hydroxide.

9. The composition of claim 6, wherein the composition is in the form of an aerosol, dispersion, solution, or suspension.

10. A method of immunizing a subject comprising administering to the subject an effective amount of the composition of claim 6.

11. A method of enhancing an immune response in a subject comprising administering to the subject an effective amount of a composition comprising:
    a) a lipid nanoparticle ("LNP") adjuvant comprising 34-59 mole % (13Z, 16Z)-N,N-dimethyl-3-nonyldocosa-13, 16-dien-1-amine, 30-48 mole % cholesterol, 10-24 mole % distearoylphosphatidylcholine (DSPC) and 1-2 mole % polyethylene glycol-dimyristoylglycerol (PEG-DMG); and
    b) one or more antigens;
    wherein the composition provides an increased γ-interferon response the one or more antigens compared to a γ-interferon response to the one or more antigens provided by the composition in the absence of the LNP adjuvant.

12. A method of enhancing an immune response in a subject comprising administering to the subject an effective amount of a composition comprising:
   a) a lipid nanoparticle ("LNP") adjuvant comprising 34-59 mole % (13Z, 16Z)-N,N-dimethyl-3-nonyldocosa-13, 16-dien-1-amine, 30-48 mole % cholesterol, 10-24 mole % distearoylphosphatidylcholine (DSPC) and 1-2 mole % polyethylene glycol-dimyristoylglycerol (PEG-DMG); and
   b) one or more antigens;

wherein the composition provides an increased amount of antibody titers to the one or more antigens compared to an amount of antibody titers to the one or more antigens provided by the composition in the absence of the LNP adjuvant.

13. A method of enhancing an immune response in a subject comprising administering to the subject an effective amount of a composition comprising:
   a) a lipid nanoparticle ("LNP") adjuvant comprising 34-59 mole % (13Z, 16Z)-N,N-dimethyl-3-nonyldocosa-13, 16-dien-1-amine, 30-48 mole % cholesterol, 10-24 mole % distearoylphosphatidylcholine (DSPC) and 1-2 mole % polyethylene glycol-dimyristoylglycerol (PEG-DMG); and
   b) one or more antigens;

wherein the composition provides an enhanced antibody response to the one or more antigens compared to an antibody response to the one or more antigens provided by the composition in the absence of the LNP adjuvant.

14. The method of claim 13, wherein the composition further comprises an immunostimulatory agent selected from the group consisting of: saponin, squalene, aluminum phosphate and aluminum hydroxide.

15. The method of claim 13, wherein the composition further comprises one or more agonists selected from the group consisting of: Toll-like receptors (TLR) agonists and Stimulator of Interferon Gene (STING) agonists.

16. The method of claim 13, wherein the composition further provides an increased amount of antibody titers to the one or more antigens compared to an amount of antibody titers to the one or more antigens provided by the composition in the absence of the LNP adjuvant.

17. The method of claim 13, wherein the composition further provides an increased y-interferon response the one or more antigens compared to a y-interferon response to the one or more antigens provided by the composition in the absence of the LNP adjuvant.

18. The method of claim 13, wherein the composition further provides an increased B-cell response to the one or more antigens compared to a B-cell response to the one or more antigens provided by the composition in the absence of the LNP adjuvant.

* * * * *